United States Patent
Benghezal et al.

(10) Patent No.: US 9,555,104 B2
(45) Date of Patent: Jan. 31, 2017

(54) IMMUNOTHERAPY COMPOSITION AND USE THEREOF

(71) Applicant: Ondek Pty Ltd, Rushcutters Bay, New South Wales (AU)

(72) Inventors: Mohammed Benghezal, Scarborough (AU); Barry Marshall, Shenton Park (AU); Alma Fulurija, White Gum Valley (AU); Senta Walton, Yokine (AU)

(73) Assignee: Ondek Pty Ltd, Rushcutters Bay (AU)

( * ) Notice: Subject to any disclaimer, the term of this patent is extended or adjusted under 35 U.S.C. 154(b) by 0 days.

(21) Appl. No.: 14/897,575

(22) PCT Filed: Jun. 20, 2014

(86) PCT No.: PCT/AU2014/050087
§ 371 (c)(1),
(2) Date: Dec. 10, 2015

(87) PCT Pub. No.: WO2014/201525
PCT Pub. Date: Dec. 24, 2014

(65) Prior Publication Data
US 2016/0175429 A1    Jun. 23, 2016

(30) Foreign Application Priority Data

Jun. 21, 2013  (AU) ................................ 2013902262
Jun. 21, 2013  (AU) ................................ 2013902268
Oct. 11, 2013  (AU) ................................ 2013903925
Dec. 20, 2013  (AU) ................................ 2013905007

(51) Int. Cl.
*A61K 35/74*    (2015.01)
*A61K 39/35*    (2006.01)
*A61K 39/02*    (2006.01)
*A61K 9/00*     (2006.01)
*A61K 39/00*    (2006.01)

(52) U.S. Cl.
CPC .............. *A61K 39/35* (2013.01); *A23L 33/135* (2016.08); *A23L 33/40* (2016.08); *A61K 9/0053* (2013.01); *A61K 9/0073* (2013.01); *A61K 35/74* (2013.01); *A61K 39/105* (2013.01); *A23V 2002/00* (2013.01); *A61K 2039/521* (2013.01); *A61K 2039/523* (2013.01); *A61K 2039/542* (2013.01); *A61K 2039/544* (2013.01); *A61K 2039/545* (2013.01); *A61K 2039/58* (2013.01)

(58) Field of Classification Search
None
See application file for complete search history.

(56) References Cited

FOREIGN PATENT DOCUMENTS

| | | |
|---|---|---|
| CA | 2837348 | 9/2012 |
| WO | 2006/015445 | 2/2006 |
| WO | 2006/133879 | 12/2006 |
| WO | 2010/041143 | 4/2010 |

OTHER PUBLICATIONS

Dunkley et al. (1994) "A role for CD4+ T cells from orally immunized rats in enhanced clearance of Pseudomonas aeruginosa from the lung," Immunology, 83:362-369.

*Primary Examiner* — Brian J Gangle
(74) *Attorney, Agent, or Firm* — Carol L. Francis; Bozicevic, Field & Francis LLP

(57) ABSTRACT

The present invention relates to the field of preventing or reducing incidence or severity of an allergic immune response, and compositions for preventing or reducing incidence or severity of an allergic immune response. For example, the present invention provides compositions comprising inactivated and/or killed cells of *Helicobacter pylori* or a cell lysate thereof, and methods and/or uses thereof for delaying or preventing or interrupting or slowing onset of one or more allergic conditions in a subject.

12 Claims, 23 Drawing Sheets

A

B

A

B

SEQUENCE LISTING

```
<160> NUMBER OF SEQ ID NOS: 4

<210> SEQ ID NO 1
<211> LENGTH: 18
<212> TYPE: DNA
<213> ORGANISM: artificial sequence
<220> FEATURE:
<223> OTHER INFORMATION: Forward primer for H. pylori

<400> SEQUENCE: 1
ttggagggct tagtctct                                                   18

<210> SEQ ID NO 2
<211> LENGTH: 20
<212> TYPE: DNA
<213> ORGANISM: artificial sequence
<220> FEATURE:
<223> OTHER INFORMATION: Reverse primer for H. pylori

<400> SEQUENCE: 2
aagattggct ccacttcaca                                                 20

<210> SEQ ID NO 3
<211> LENGTH: 10
<212> TYPE: DNA
<213> ORGANISM: artificial sequence
<220> FEATURE:
<223> OTHER INFORMATION: Primer 1254

<400> SEQUENCE: 3
ccgcagccaa                                                            10

<210> SEQ ID NO 4
<211> LENGTH: 10
<212> TYPE: DNA
<213> ORGANISM: artificial sequence
```

```
<220> FEATURE:
<223> OTHER INFORMATION: Primer 1281

<400> SEQUENCE: 4
aacgcgcaac                                                          10
```

IMMUNOTHERAPY COMPOSITION AND USE THEREOF

FIELD OF THE INVENTION

The present invention relates to the field of preventing or reducing incidence or severity of an allergic immune response, and compositions for preventing or reducing incidence or severity of an allergic immune response.

BACKGROUND TO THE INVENTION

Allergic reactions are generally immune reactions that are initiated by IgE-dependent stimulation of tissue mast cells and related effector molecules (e.g., basophils). Binding events between cell surface bound IgE molecules and antigen results in rapid release of biological response modifiers which bring about increased vascular permeability, vasodilation, smooth muscle contraction and local inflammation. This sequence of events is termed immediate hypersensitivity and begins rapidly, usually within minutes of exposure in a sensitised individual. In its most severe systemic form, anaphylaxis, such immediate hypersensitivity can bring about asphyxiation, produce cardiovascular collapse, and even result in death. Individuals that are prone to strong immediate hypersensitivity responses are referred to as "atopic". Clinical manifestations of allergy or atopy include hay fever (rhinitis), asthma, urticaria (hives), skin irritation (e.g., eczema such as chronic eczema), anaphylaxis, and related conditions.

The prevalence of atopy has increased in the developed world since the beginning of the 20$^{th}$ century when allergy prevalence was estimated to be less than 0.1% in Europe, UK and US (Schadewaldt H, 1980, Geschichte der Allergies in vier Dustri-Verlag; as cited by Matthias Wjst, 2009, *Allergy, Asthma & Clinical Immunology.* 5:8). About 30-40% of the world population is now affected by one or more allergic conditions. Asthma, rhinitis, and eczema are now prevalent in developed countries, with allergic disorders being the most common chronic diseases among children in developed countries. For example, more than 25% of infants in Australia today present with eczema, more than 20% of one-year olds are food-sensitised, more than 25% of children have asthma, and more than 40% of adults have a history of allergic rhinitis (Pawnkar R, Walter Canonica G, Holgate S T, Lockey R F, 2001, World Allergy Organization (WAO) White Book on Allergy). Allergies also affect about 20% of all individuals in the United States. Atopy is predicted to increase to about 26 of the Australian population by 2050.

Although childhood asthma often improves during childhood, asthma and rhinitis persist throughout adulthood, with substantial increase in asthma associated mortality for those aged more than 60 years (Martin P E et al., 2011, *J. Allergy Clin. Immunol.* 127:1473-1479).

There is a significant economic burden associated with allergic conditions. For example, in 2007 the associated economic cost in Australia was estimated to be $9.4 billion with an additional $21.3 billion from lost wellbeing (e.g., disability and premature death). In the UK, the total annual expenditure for atopic eczema has been estimated at £465 million (€ 521 m). In Germany, the total average costs for an atopic eczema patient have been estimated to be about € 4400. In the US, the direct and indirect costs of asthma to the US economy were projected to have reached US$20.7 billion in 2010, and the direct cost of treating childhood asthma alone exceeds US$1,100 per patient per annum. The cost of treating incidence of eczema alone in patients aged 0 to 5 years is approximately US$360 per patient per annum with an annual cost of over $400,000 in Australia, € 5 million in Western Europe and US$3 million in the US.

Several studies have documented temporal changes in allergy patterns in developed countries, from a prevalence of allergic asthma and hay fever in children (Mullins R J, 2007, *Med J Aust.* 186: 618-621) toward increasing eczema and food allergies during the last 10 years. In this second wave of the allergy epidemic, 10% of children have some form of food allergy (Osborne N J et al., 2011, *J. Clin. Immunol.* 127:668-676; Prescott S and Allen K J, 2011, *Pediatr. Allergy Immunol.* 22:155-160). This changing epidemiology for allergic disorders remains largely unexplained.

As illustrated in panel (A) of FIG. 1 hereof, infants who have moderate to severe eczema are at higher risk of developing food allergies and/or allergic asthma later in life e.g., during childhood, and a significant proportion of these individuals will have atopic or respiratory allergies as adults. This is the so-called "atopic march" or "allergic march" (Martin P E et al., 2011, *J. Allergy Clin. Immunol.* 127:1473-1479). The current generation with food allergies appear to present with symptoms earlier in life than previous generations having respiratory allergies, and appear less likely to outgrow their allergy during early adulthood (Prescott S and Allen K J, 2011, *Pediatr. Allergy Immunol.* 22:155-160).

The so-called "hygiene hypothesis" attributes the increase in atopy in developed countries to an increase in the use of antibiotics to treat microbial infections in infancy and/or childhood (Strachan D P, 1989, *BMJ,* 299:1259-1260; Strachan D P, Harkins L S, Golding J, 1997, *Clin. Exp. Allergy.* 27:151-155; Renz H and Herz U, 2002, *Eur. Respir. J.* 19:158-171). According to the hygiene hypothesis, changes in the biodiversity of the microbial environment, human microbiome, and reduced exposure to microbes that regulate the host immune system cause childhood allergy leading to the atopic march e.g., because antibiotics reduce the incidence of microorganisms that are beneficial for a balanced immune system development in addition to reducing the incidence of pathogens (Guarner F et al., 2006, *Nat. clin. Pract. Gastroenterol. Hepatol.* 3: 275-284).

Selection of an appropriate T-cell population occurs during the early stages of immune responses in naive unsensitised hosts such as neonates and new borns and infants having an undeveloped immune system. If selection favours priming the host immune system toward the induction of allergen-specific TH1 cells, then IgG and IgA responses may ensue. TH1 cells seem to play a role in defense against various microbial antigens including bacterial, viral and fungal infections, and uncontrolled TH1 responses are involved in organ-specific autoimmunity e.g., in rheumatoid arthritis, multiple sclerosis, thyroiditis, Crohn's disease, systemic lupus erythematosus, experimental autoimmune uveoretinitis (Dubey et al., 1991, *Eur. Cytokine Network,* 2:147-152), experimental autoimmune encephalitis (EAE) (Beraud et al., 1991, *Cell Immunol.* 133:379-389), insulin-dependent diabetes mellitus (Hahn et al., 1987, *Eur. J Immunol.* 18:2037-2042), contact dermatitis (Kapsenberg et al., *Immunol Today,* 12:392-395), and in some chronic inflammatory disorders. The principal inflammatory cytokine produced by TH1 cells is IFN-γ (See, for example, Romragnani, ed, TH1 and TH2 Cells in Health and Disease. Chem. Immunol., Karger, Basel, 63, pp. 158-170 and 187-203 (1996)).

On the other hand, the emergence of TH2 cells can lead to IgE production and eosinophilia and ultimately atopic disease. See e.g., WO2005/030249. Allergy, asthma, eczema, psoriasis, allergic rhinitis, hay fever and atopic dermatitis are each associated with a profound immunological deregulation characterized by over production of TH2 cells (Romragnani, supra; van der Heijden et al., 1991; *J Invest Derm.* 97:389-394; Walker et al., 1992, *Am. Rev. Resp. Dis.* 148:109-115; and Renz H and Herz U, 2002, supra), and uncontrolled TH2 type responses are responsible for triggering allergic disorders against environmental allergens and chemical allergens. TH2 type responses are also preferentially induced in certain primary immune deficiencies such as hyper-IgE syndrome (Del Prete et al., 1989, *J. Clin. Invest.* 84:1830-1835) and Omenn's syndrome (Schandene et al., 1993, *Eur. J. Immunol.* 23:56-60).

TH2 effector functions may be negatively regulated by TH1 cells. The hygiene hypothesis suggests that a reduced frequency of microbial infections, less severe infection, and prevention of infection e.g., by frequent use of antibiotics may prevent maturation of TH1 immunity, and give rise to allergen-specific TH-2 immune responses following subsequent exposure to allergens (Renz H and Herz U, 2002, supra).

There is currently no cure, and only limited treatment, for severe atopy. Treatment options are generally restricted to use of steroids, anti-histamines, immune modulation drugs and administration of adrenalin. At best these treatment regimens provide temporary relief and are generally not suitable for sustained use. Accordingly, there remains an unmet need in the art for compositions and methods for prevention of allergic disorders.

*H. pylori* is a gastric bacterial pathogen that chronically infects more than half of the world's human population. Infection with *H. pylori* is usually acquired early in childhood and, if left untreated, can last for a life time with the majority of infected individuals remaining asymptomatic. On the other hand, *H. pylori* infection is the main cause of peptic ulcer disease, which is manifested in more than 10% of infected subjects (Kuipers et al., 1995. *Aliment Pharmacol Ther,* 9 Suppl 2: 59-69). *H. pylori* infection is also associated with an increased risk of non-cardiac gastric adenocarcinoma which is one of the most frequently lethal malignancies, and with gastric mucosa-associated lymphoid tissue (MALT) lymphoma (Suerbaum & Michetti, 2002, *N Engl J Med,* 347: 1175-1186; Atherton (2006), *Annu Rev Pathol.* 1:63-96), as well as chronic urticaria (hives).

Epidemiological population studies suggest that prevalence of live *H. pylori* in the gastric mucosa is inversely-proportional to the incidence of allergy in developed countries. See e.g., Zevit et al., (2011), *Helicobacter,* 17: 30-35; Shiotani et al., (2008), *BMJ,* 320: 412-7; Chen & Blaser (2007), *Arch Intern Med,* 167: 281-7; McCune et al., (2003), *Eur J Gastroenterol Hepatol,* 15: 637-40; Reibman et al., (2008), *PLoS ONE,* 3: e4060; Konturek et al., (2008), *Med Sci Monit,* 14:CR453-8. However, a number of other studies have suggested that the correlation between falling *H. pylori* infection rates and raising allergy rates might not be correct. See, e.g., Zevit et al., (2011) supra; Raj et al. (2009), *J Infect Dis,* 199:914-5. These conflicting reports suggest uncertainty as to whether or not reduced colonization of the gastric mucosa by *H. pylori* is directly involved in the atopic march.

SUMMARY OF THE INVENTION

1. General

In work leading to the present invention, the inventors sought to identify and/or prepare composition(s) for improving tolerance of the immune system of a mammalian subject to allergy e.g., by preventing or delaying the development of atopy or the atopic march in a subject. In particular, the inventors sought to identify and/or prepare composition(s) capable of preventing or reducing severity or incidence of allergic immune response(s) to an allergen in a mammalian subject, or capable of preventing or attenuating severity of allergic disease such as airway hyper-responsiveness in a mammalian subject following exposure of the subject to an allergen. The inventors also sought to identify and/or prepare composition(s) capable of preventing or interrupting or limiting the atopic march and progression of an allergic disease such as eczema in children e.g., neonates and juveniles to food allergy and/or severe asthma later in life for example during adolescence and/or adulthood.

The inventors reasoned that an optimally-balanced immune system develops in the early post-natal period and, as a consequence, administration of a medicament to prevent the atopic march in a subject and development of allergy in adolescents and adults is optimally deliverable to neonates or during early childhood.

As exemplified herein, the present inventors have shown that an oral composition comprising inactivated and/or killed *H. pylori* administered to neonates or adults in a murine model of allergy reduced the incidence or severity of an allergic response to antigenic challenge e.g., as determined by measurement of airway or lung resistance. Thus, administration of an inactivated and/or killed *H. pylori* e.g., wherein the inactivated *H pylori* does not have the same capacity of a live *H. pylori* to colonize the mucosa of a mammal to which it is administered or wherein the inactivated or killed *H. pylori* is incapable of colonizing the mucosa of a mammal to which it is administered, or a *H. pylori* cell lysate, appears to interrupt or slow or arrest or prevent atopic march or further atopic march in the subject e.g., by delaying or preventing or interrupting or slowing the onset of one or more allergic conditions such as allergic eczema, urticaria, hives, rhinitis, wheezing, airway resistance, airway restriction, or airway hyper-responsiveness or hyper-reactivity, food allergy, asthma etc.

The present invention therefore provides for a general reduction in hyper-responsiveness of an individual to one or more allergens thereby delaying or preventing or interrupting or slowing the onset of one or more allergic conditions. The reduced hypersensitivity may be demonstrated by reduced sensitivity of a subject to a specific allergen e.g., an accepted model allergen of hypersensitivity e.g., ovalbumin and/or ragweed administered as a challenge to murine animals e.g., BALB/c or C57/BL/6 or SJL/J mice, in an aerosolized form or by gavage. See e.g., Renz et al., *J. Allergy Clin. Immunol.* 89:1127-1138 (1992); Renz et al., *J. Immunol.* 151:1907-1917 (1993); Saloga et al., *J. Clin. Invest.* 91:133-140 (1993); Larsen et al., *J. Clin. Invest.* 89:747-752 (1992); Oshiba et al., *J. Clin, Invest.* 97: 1938-1408 (1996).

For example, by administering inactivated and/or killed *H. pylori* e.g., isolated inactivated and/or killed *H. pylori*, to a subject that is asymptomatic for eczema, or asymptomatic for allergy e.g., characterized by rhinitis or wheezing or airway resistance or restriction or airway hyper-responsiveness, or asymptomatic for asthma, a subsequent onset of eczema and/or allergy and/or asthma may be prevented. In one specific example, inactivated and/or killed *H. pylori* is administered to a juvenile subject such as a neonate or infant to prevent eczema in the infant or a subsequent onset of allergy or asthma in later life e.g., in adolescence or adulthood. In another example, inactivated and/or or killed *H. pylori* e.g., isolated inactivated and/or killed *H. pylori*, is administered to an adolescent or adult subject to prevent eczema in the subject or a subsequent onset of allergy or asthma, such as in later life. This is in a background in which allergic eczema, allergy or asthma is inducible at any stage of life by exposure of a subject to one or more challenge allergens, including one or more environmental allergens e.g., pollen allergen, dust mite allergen, animal allergen, chemical allergen etc.

Alternatively, by administering inactivated and/or killed *H. pylori* e.g., isolated inactivated and/or killed *H. pylori*, to a subject that has suffered previously from one or more incidences of allergic eczema, allergy e.g., characterized by rhinitis or wheezing or airway resistance or restriction, or asthma, a subsequent attack may be prevented or the severity of a subsequent attack may be reduced. In one specific example, inactivated and/or killed *H. pylori* e.g., isolated inactivated and/or killed *H. pylori* is administered to a juvenile subject that has suffered from allergic eczema to prevent a subsequent attack or reduce severity of a subsequent attack, optionally to prevent or slow further atopic march in the subject. In another example, inactivated and/or killed *H. pylori* e.g., isolated inactivated and/or killed *H. pylori* is administered to an adolescent or adult subject that has suffered previously from allergic eczema and/or allergy and/or asthma, to prevent a subsequent attack or reduce severity of a subsequent attack, optionally to prevent or slow further atopic march in the subject.

In an epidemiological context, the administration of inactivated and/or killed *H. pylori* e.g., isolated inactivated and/or killed *H. pylori* to a subject reduces the incidence of allergic immune responses in the population, and especially reduces the incidence of allergic immune responses in adolescent and/or adult members of the population treated when they were juveniles.

The demonstration that inactivated and/or killed *H. pylori* bacteria protect subjects in a mouse model of allergic airway disease provides the significant advantage of avoiding health risks associated with the use of live *H. pylori* cells, such as induction of peptic ulcers and/or gastric cancer. In other words, inactivated and/or killed *H. pylori* or a lysate of *H. pylori* offers a safe and controlled approach for positively-influencing the developing immune system, and preventing or reducing an allergic response to an allergen. Similarly, inactivated and/or killed *H. pylori* or a lysate of *H. pylori* offers a safe and controlled approach to delaying or preventing the atopic march by targeting events in early in life e.g., in children such as neonates and/or juveniles.

The present invention thus provides for administration, for example repeated administration, of inactivated and/or killed *H. pylori* bacteria and/or a lysate thereof e.g., to children or infants such as at 0 to 5 years of age, to thereby promote balanced immune development for reducing the severity or incidence of allergy e.g., as allergic eczema and/or a life-long food allergy and/or allergic asthma. The inactivated and/or killed *H. pylori* bacteria and/or a lysate thereof is also useful for modulating the immune system of a mammalian subject and/or for improving the immune system's tolerance to allergy.

As disclosed herein, the inactivated and/or killed *H. pylori* bacteria and/or a lysate thereof are formulated and/or used as a food ingredient or a food product such as medical food e.g., diary or non-dairy and/or dietary supplement(s) and/or as tablet(s) and/or as capsules. Such formulations are preferably mucosal compositions for improving immune system's tolerance to allergens and/or preventing or reducing allergy symptoms for example in adults and/or adolescents. The formulations are preferably for repeated administration, e.g., daily, to children and/or infants, e.g., aged 0 to 5 years, suffering from eczema and/or food allergy or susceptible to development of eczema or food allergy. In this respect, a subject may be susceptible to development of allergy at 0-5 years or 0-4 years or 0-3 year or 0-2 years or 0.5-5 years or 0.5-4 years or 0.5-3 years or 0.5-2 years or 0.5-1 years or 1-2 years or 1-3 years or 1-4 years or 1-5 years or 2-3 years or 2-4 years or 2-5 years or 3-4 years or 3-5 years of age. For example, to prevent or limit the atopic march in a subject, such as progression to food allergy and/or allergic asthma later in life, the subject is administered a plurality of doses of a formulation comprising the inactivated *H. pylori* or cell extract or lysate thereof, wherein the first does is administered at a time infra where the subject is susceptible to development of allergy. For example, the subject may be taking antibiotic therapy or prescribed antibiotic therapy, especially in the case of an infant or child that is susceptible to development of allergy.

Without being bound by theory or specific mode of action, the inventors postulated that the inactivated and/or killed *H. pylori* of the present invention retain and/or form a cell structure scaffold and/or a conglomerate or aggregate of cell structure scaffold. Without being bound by theory or specific mode of action, the inventors also postulated that this scaffold and/or conglomerate or aggregate may be important for facilitating immune modulation in a subject towards a balanced immune response to an allergen e.g., balanced Th1/Th2 immune response in a subject and/or to interrupt or slow or arrest or prevent atopic march or further atopic march in the subject e.g., by delaying or preventing or interrupting or slowing the onset of one or more allergic conditions described herein.

SPECIFIC EXAMPLES OF THE INVENTION

The scope of the invention will be apparent from the claims as filed with the application that follow the examples. The claims as filed with the application are hereby incorporated into the description. The scope of the invention will also be apparent from the following description of specific embodiments and/or detailed description of preferred embodiments.

Accordingly, in one example, the invention provides a composition comprising an *H. pylori* cell, a cell lysate thereof or combination thereof and a pharmaceutically accepted carrier, wherein said *H. pylori* cell is inactivated e.g., by virtue of having reduced capacity to colonize the mucosa of a mammal relative to a live *H. pylori* cell such as a live *H. pylori* cell having the same genotype as the inactivated cell, or by virtue of being incapable of colonizing the mucosa of said mammal, and preferably wherein the *H. pylori* is killed e.g., by heat treatment.

In some embodiments, the composition of the present invention consists essentially of an *H. pylori* cell and/or a cell lysate thereof together with a pharmaceutically acceptable carrier, wherein said *H. pylori* cell is inactivated e.g., by virtue of having reduced capacity to colonize the mucosa of a mammal relative to a live *H. pylori* cell for example having the same genotype as the inactivated cell, or by virtue of being incapable of colonizing the mucosa of said mammal, and preferably wherein the *H. pylori* is killed e.g., by heat treatment.

It will be appreciated by those skilled in the art that any *H. pylori* strain is used; however, in some examples the *H. pylori* strain is cagA minus (cagA$^-$). In some examples, the *H. pylori* strain is cagA$^-$ and is also positive for the toxigenic s1 and m1 alleles of the vacA gene.

In some examples, the present invention provides strains of *H. pylori* having the characteristics of a strain selected from the group consisting of OND737, as deposited in the National Measurement Institute under Accession No. V09/009101; OND738, as deposited in the National Measurement Institute under Accession No. V09/009102; OND739, as deposited in the National Measurement Institute under Accession No. V09/009103; OND248, as deposited in the National Measurement Institute under Accession No. V10/014059; OND256 as deposited in the National Measurement Institute under Accession No. V10/014060; OND740, as deposited in the National Measurement Institute under Accession No. V09/009104; OND79, as deposited in the National Measurement Institute under Accession No. V13/023374, and/or OND86, as deposited in the National Measurement Institute under Accession No. V14/013016, or a passaged strain, a mutant or a derivative thereof.

In some examples, the *H. pylori* strain of the present invention has been passaged through an animal host such as a human host. For example, the *H. pylori* strain of the present invention is derived from the *H. pylori* strain OND79 after passage of the OND79 strain in a human subject e.g., following infection and/or colonization of the gastric mucosa of a human subject with *H. pylori* OND79 strain. In one such example, the *H. pylori* strain of the present invention is OND86.

While the *H. pylori* strain used in the present invention is typically a non-genetically modified bacterium, in some examples the *H. pylori* strain is genetically modified to comprise one or more nucleic acid molecule(s) encoding at least one heterologous antigen or a functional fragment thereof.

In some examples the nucleic acid molecule resides extra-chromosomally on, for example, a plasmid vector such as a shuttle vector. Preferably, the plasmid vector would comprise (a) a nucleic acid sequence encoding the heterologous antigen and (b) a control or regulatory sequence operatively linked thereto which is capable of controlling the expression of the nucleic acid when the vector is transformed into a *H. pylori* strain. In other examples, the nucleic acid molecule inserts into the *H. pylori* chromosome upon transformation into the *H. pylori*.

Suitable antigens will be known to the person skilled in the art. Preferably the antigen is an environmental antigen, and may be used either singly or as a combination of two or more such antigens.

In some examples, the composition of the present invention will comprise an adjuvant. The adjuvant may be any adjuvant known in the art; however, preferably, the adjuvant is selected from the group consisting of alum, petiussis toxin, lacto fucopentaose III, phosphopolymer, complete Freund's adjuvant, monophosphoryl lipid A, 3-de-O-acylated monophosphoryl lipid A (3D-MPL), aluminium salt, CpG-containing oligonucleotides, immunostimulatory DNA sequences, saponin, MONTANIDE® 1SA 720, SAF, ISCOM.S, MF-59®, SBAS-3, SBAS-4, Detox, RC-529, aminoalkyl glucosaminide 4-phosphate, and LbeiF4A or combinations thereof. Alternatively, in other examples, the mucosal composition of the present invention does not comprise an adjuvant and/or is administered in the absence of an adjuvant.

The invention is useful in preventing and/or treating allergy in a mammal at risk of developing an allergy or having an allergy. In some examples, the allergy is selected from the group consisting of contact dermatitis, chronic inflammatory disorders, allergic atopic disorders, allergic asthma, atopic dermatitis, hyper-IgE syndrome, Omenn's syndrome, psoriasis, hay fever, allergic rhinitis, urticaria, eczema and food allergies.

Accordingly, in a further example the present invention provides a composition for use in preventing or treating allergy in a mammal comprising an *H. pylori* cell such as an isolated *H. pylori* cell, a cell lysate thereof or combination thereof and a pharmaceutically accepted carrier, wherein said *H. pylori* cell is either killed or incapable of colonizing the mucosa of said mammal. Optionally, the cell lysate is a whole cell lysate (WCL) of the inactivated *H. pylori* cell.

In a further example, the present invention provides a composition comprising an *H. pylori* cell such as an isolated *H. pylori* cell, or a cell lysate thereof or combination thereof and a pharmaceutically acceptable carrier, wherein said *H. pylori* cell is inactivated e.g., by virtue of having reduced capacity to colonize the mucosa of a mammal relative to a live *H. pylori* cell for example having the same genotype as the inactivated cell or by virtue of being incapable of colonizing the mucosa of a mammal. Preferably, the composition is for mucosal delivery. Optionally, the cell lysate is a whole cell lysate (WCL) of the inactivated *H. pylori* cell.

In another example, the present invention provides a composition comprising inactivated and/or killed *H. pylori* cells, such as isolated inactivated and/or killed *H. pylori* cells, or a cell lysate thereof, wherein said composition is formulated to be administered mucosally to a subject for interrupting or slowing or arresting or preventing an atopic march or progression of an atopic march in the subject. For example, the cell lysate is a WCL. In one such example, interrupting or slowing or arresting or preventing an atopic march or progression of an atopic march in the subject comprises delaying or preventing or interrupting or slowing the onset of one or more allergic conditions in the subject.

For example, an allergic condition may comprise allergic eczema, urticaria, hives, rhinitis, wheezing, airway resistance, airway restriction, lung inflammation, food allergy, or asthma. Preferably, an allergic condition comprises airway resistance or airway hyperresponsiveness or hyperreactivity in response to an allergen and wherein the composition is for reducing said airway resistance. Alternatively, or in addition, an allergic condition comprises lung inflammation in response to an allergen and wherein the composition is for reducing said lung inflammation e.g., as characterized by a reduced level of cell infiltrate in lung. Alternatively, or in addition, an allergic condition is characterized by an elevated serum level of allergen-specific IgE antibody and/or an elevated level of one or more inflammatory cytokines in bronchioalveolar lavage (BAL) and/or an elevated level of cell infiltrate in lung. For example, the composition reduces a serum level of allergen-specific IgE antibody and/or a level of one or more inflammatory cytokines in bronchioalveolar lavage (BAL) and/or a level of cell infiltrate in lung relative to a level thereof in a subject exposed to an allergen and not administered said composition. Alternatively, the composition prevents or delays an increase in a serum level of allergen-specific IgE antibody and/or prevents or delays an increase in a level of one or more inflammatory cytokines in bronchioalveolar lavage (BAL) and/or prevents or delays an increase in a level of cell infiltrate in lung in a subject exposed to an allergen.

Preferably, the composition as described according to any example hereof comprises *H pylori* cells or strains which have reduced capability in colonizing the mucosa of a subject relative to live *H pylori* cells or strains or are incapable of colonizing the mucosa of a subject. Alternatively, or in addition, the composition according to any example described hereof comprises *H pylori* cells or strains which are inactivated e.g., by irradiation such as gamma irradiation and/or ultraviolet irradiation and/or heat treatment and/or chemical means and/or by exposure to acid and/or by exposure to a base and/or by physical means such as pressure and/or by lyophilisation and/or by freeze-thawing. Alternatively, or in addition, the composition according to any example hereof comprises *H. pylori* cells or strains which are killed e.g., by heat treatment such that the cells are rendered irreversibly metabolically inactive. In another example, the composition according to any example hereof comprises *H pylori* cells or strains that have been subjected to a process for inactivating *H. pylori* cells and a process for killing the *H. pylori* cells. In one particular example, the inactivated *H. pylori* cells or strains described according to any example hereof are killed.

Alternatively, or in addition, the composition described according to any example hereof comprises a lysate e.g., WCL of *H. pylori* cells wherein the cells have been subjected to a process for inactivating *H. pylori* cells and/or a process for killing the *H. pylori* cells.

For example, inactivated *H. pylori* as described according to any example hereof is prepared by exposing live *H. pylori* cells or strains to irradiation such as gamma irradiation and/or ultraviolet irradiation and/or by exposure to visible light such as wavelengths ranging from about 375 nm to about 500 nm or in a range from about 400 nm to about 420 nm e.g., 405 nm violet light. In one example, inactivated *H. pylori* as described according to any example hereof is prepared by a process comprising exposing live *H. pylori* cells or strains to ultraviolet C (UVC) irradiation such as wavelength in a range from about 100 nm to about 280 nm such as about 257.3 nm and/or to ultraviolet B (UVB) irradiation such as wavelength in a range from about 280 nm to about 315 nm and/or to ultraviolet A (UVA) irradiation such as wavelength in a range from about 315 nm to about 400 nm. Preferably, the live *H. pylori* is exposed to UVC light in a range from about 100 nm to about 280 nm such as about 257.3 nm and/or the live *H. pylori* is exposed to about 405 nm violet light.

Alternatively, or in addition, inactivated *H. pylori* as described according to any example hereof is prepared by exposing live *H. pylori* cells or strains to one or more chemical agents such as formaldehyde and/or β-propiolactone and/or ethyleneimine and/or binary ethyleneimine and/or thimerosal and/or polyethyleneimine functionalized zinc oxide nanoparticles, or derivatives thereof. For example, live *H. pylori* cells or strains may be inactivated by exposure to formaldehyde at a concentration from about 0.01% to about 1% (w/w) or from about 0.01% to about 0.1% (w/w) or between about 0.025% and about 0.1% (w/w).

Alternatively, or in addition, inactivated *H. pylori* as described according to any example hereof is prepared by exposing live *H. pylori* cells or strains to heat treatment such as at temperatures in the range between about 40° C. to about 70° C. or more. Alternatively, or in addition, inactivated *H. pylori* as described according to any example hereof is prepared by exposing live *H. pylori* cells or strains to one or more acid(s) or to a low pH environment such as pH 3.0 or lower and/or to one or more base(s) or to high pH environment such as pH 9.0 or higher.

Alternatively, or in addition, inactivated *H. pylori* as described according to any example hereof is prepared by exposing live *H. pylori* cells or strains to one or more reducing agent(s) such as sodium bisulfite and/or one or more oxidative agents such as hydrogen peroxide.

Alternatively, or in addition, inactivated *H. pylori* as described according to any example hereof is prepared by exposing live *H. pylori* cells or strains to bile salts.

Alternatively, or in addition, inactivated *H. pylori* as described according to any example hereof is prepared by mutagenesis of live *H pylori* cells or strains.

Alternatively, or in addition, inactivated *H. pylori* as described according to any example hereof is prepared by lyophilizing or freeze-drying live *H. pylori* cells or strains. Alternatively, or in addition, inactivated *H pylori* as described according to any example hereof is prepared by performing one or cycles of freezing and thawing live *H. pylori* cells or strains.

For example, killed *H. pylori* as described according to any example hereof is prepared by exposing live and/or inactivated *H. pylori* cells or strains to heat treatment such as by exposure to temperature of about 60° C. or more for at least about 60 seconds, preferably at a temperature of about 60° C. or about 70° C. or about 80° C. or about 90° C. or about 100° C. or about 110° C. or about 120° C. or about 130° C. or about 140° C. or about 150° C., said temperature exposure being for a period of at least 2 minutes or at least 3 minutes or at least 4 minutes or at least 5 minutes or at least 6 minutes or at least 7 minutes or at least 8 minutes or at least 9 minutes or at least 10 minutes or at least 20 minutes or at least 30 minutes or at least 40 minutes or at least 50 minutes or at least 1 hour or at least 2 hours or at least 3 hours or at least 4 hours or at least 5 hours or at least 6 hours or at least 7 hours or at least 8 hours or at least 9 hours or at least 10 hours or at least 11 hours or at least 12 hours or at least 13 hours or at least 14 hours or at least 15 hours or at least 16 hours or at least 17 hours or at least 18 hours or at least 19 hours or at least 20 hours or at least 21 hours or at least 22 hours or at least 23 hours or at least 1 day or at least 2 days or at least 3 days or at least 5 days or at least 5 days or at least 6 days or at least 7 days. In one preferred example, live and/or inactivated *H. pylori* is killed by exposure to a single such elevated temperature or by exposure to at least two different elevated temperatures such as by exposure to a first temperature of about 70° C. followed exposure to a second temperature of about 90° C. or about 95° C. In one such preferred example, the live and/or inactivated *H pylori* is killed by exposure to temperature of about 70° C. for about 10 minutes followed by exposure to temperature of about 90° C. or about 95° C. for about 5 minutes.

Alternatively, or in addition, killed *H. pylori* as described according to any example hereof is prepared by exposing live and/or inactivated *H. pylori* cells or strains to elevated temperatures in the presence of steam and elevated pressure, such as by autoclaving live and/or inactivated *H. pylori* cells or strains. For example, live and/or inactivated *H. pylori* is killed by autoclaving the bacterial cells or strains for about 15 minutes at about 121° C. and about 15 psi, or for about 3 minutes at about at 132° C. and about 30 psi.

Alternatively, or in addition, killed *H. pylori* as described according to any example hereof is prepared by exposing live and/or inactivated *H. pylori* cells or strains to one or more bactericidal agent(s). For example, live and/or inactivated *H. pylori* can be subjected to treatment with one or more antibiotics selected from rifampin, amoxicillin, clarithromycin, rifamycin, rifaximin, the rifamycin derivative 3'-hydroxy-5'-(4-isobutyl-1-piperazinyl)benzoxazinorifamycin syn. KRM-1648 and/or the rifamycin derivative 3'-hydroxy-5'-(4-propyl-1-piperazinyl)benzoxazinorifamycin syn. KRM-1657.

Alternatively, or in addition, killed *H. pylori* as described according to any example hereof is prepared by exposing live and/or inactivated *H. pylori* cells or strains to irradiation such as gamma irradiation and/or ultraviolet irradiation and/or by exposure to visible light such as wavelengths ranging from about 375 nm to about 500 nm or in a range from about 400 nm to about 420 nm. For example, killed *H. pylori* is prepared by a process comprising exposing live and/or inactivated *H. pylori* cells or strains to ultraviolet C (UVC) irradiation such as wavelength in a range from about 100 nm to about 280 nm such as about 257.3 nm and/or to ultraviolet B (UVB) irradiation such as wavelength in a range from about 280 nm to about 315 nm and/or to ultraviolet A (UVA) irradiation such as wavelength in a range from about 315 nm to about 400 nm. Preferably, the live and/or inactivated *H. pylori* is exposed to UVC light in a range from about 100 nm to about 280 nm such as about 257.3 nm and/or the live and/or inactivated *H. pylori* is exposed to about 405 nm violet light.

Alternatively, or in addition, killed *H. pylori* as described according to any example hereof is prepared by sonication e.g., at ultrasonic frequencies such as about 20 kHz or more.

Alternatively, or in addition, killed *H. pylori* as described according to any example hereof is prepared by mutagenesis of live and/or inactivated *H. pylori* cells or strains.

Preferably, the killed *H. pylori* as described according to any example hereof is prepared by first by exposing live *H. pylori* cells or strains to irradiation such as gamma irradiation and/or ultraviolet irradiation such as UVC light and/or by exposure to visible light such as wavelengths ranging from about 375 nm to about 500 nm or in a range from about 400 nm to about 420 nm, to thereby inactivate *H. pylori* and then exposing the inactivated *H. pylori* cells or strains to heat treatment as described according to any example hereof to thereby kill the inactivated *H. pylori* or render the inactivated *H. pylori* irreversibly metabolically inactive.

For example, the inactivated *H. pylori* is exposed to temperature of about 60° C. or more for at least about 60 seconds, preferably at a temperature of about 60° C. or about 70° C. or about 80° C. or about 90° C. or about 100° C. or about 110° C. or about 120° C. or about 130° C. or about 140° C. or about 150° C., said temperature exposure being for a period of at least 2 minutes or at least 3 minutes or at least 4 minutes or at least 5 minutes or at least 6 minutes or at least 7 minutes or at least 8 minutes or at least 9 minutes or at least 10 minutes or at least 20 minutes or at least 30 minutes or at least 40 minutes or at least 50 minutes or at least 1 hour or at least 2 hours or at least 3 hours or at least 4 hours or at least 5 hours or at least 6 hours or at least 7 hours or at least 8 hours or at least 9 hours or at least 10 hours or at least 11 hours or at least 12 hours or at least 13 hours or at least 14 hours or at least 15 hours or at least 16 hours or at least 17 hours or at least 18 hours or at least 19 hours or at least 20 hours or at least 21 hours or at least 22 hours or at least 23 hours or at least 1 day or at least 2 days or at least 3 days or at least 5 days or at least 5 days or at least 6 days or at least 7 days. In one such example, the inactivated *H. pylori* is exposed to a single such elevated temperature or to at least two different elevated temperatures such as by exposure to a first temperature of about 70° C. e.g., for about 10 minutes, followed by exposure to a second temperature of about 90° C. or about 95° C. e.g., for about 5 minutes.

In one preferred example, the killed *H. pylori* as described according to any example hereof is prepared by first by exposing live *H. pylori* cells or strains to ultraviolet irradiation such as UVC light e.g., at about as 257.3 nm to thereby inactivate *H. pylori* and then exposing the inactivated *H. pylori* cells or strains to heat treatment as described according to any example hereof to thereby kill the inactivated *H. pylori* or render the inactivated *H. pylori* irreversibly metabolically inactive.

Accordingly, in one preferred example, the composition according to any example hereof comprises *H. pylori* that has been subjected to a process for inactivating *H. pylori* by irradiation and a process for the killing the inactivated *H. pylori* by heat treatment.

Alternatively, or in addition, *H. pylori* as described according to any example hereof is inactivated and/or killed by exposing live or inactivated *H. pylori* to anaerobic conditions e.g., by changing the atmosphere in which *H. pylori* is cultured from microaerobic to anaerobic environment for example to mimic the in vivo atmospheric conditions during the washout of *H. pylori* from the stomach to the lower gut (e.g., small and/or large intestine). For example, live (such as freshly grown) *H. pylori* is inactivated by exposing (e.g., by growing or incubating) the bacterial cells to anaerobic conditions for about 1 day to about 5 days or more, including for at least about 24 hours, or for at least about 48 hours or at least about 72 hours or at least about 96 hours or at least about 120 hours. In one such example, the live *H. pylori* cells are inactivated by exposing the cells to anaerobic conditions and by heat treatment of the cells.

In another example, live or inactivated *H. pylori* as described according to any example hereof is killed by exposing (e.g., by incubation) the live or inactivated bacterial cells to anaerobic conditions for about 1 day to about 5 days or more, including for at least about 24 hours, or for at least about 48 hours or at least about 73 hours or at least about 96 hours or at least about 120 hours.

In one preferred example, the composition according to any example hereof comprises *H. pylori* that has been subjected to a process for inactivating *H. pylori* by exposing (e.g., by growing or incubating) the bacterial cells to anaerobic conditions for about 1 day to about 5 days or more, including for at least about 24 hours, or for at least about 48 hours or at least about 73 hours or at least about 96 hours or at least about 120 hours, and a process for the killing the inactivated *H. pylori* by heat treatment of the cells.

In a further example, the composition according to any example described hereof comprises a pharmaceutically acceptable carrier. In one preferred example, the composition does not include an adjuvant.

In a further example, the composition according to any example described hereof is an oral formulation formulated for ingestion. Alternatively, the composition according to any example described hereof is formulated for inhalation. For example, the composition according to any example described hereof is formulated as a foodstuff or dietary supplement. In one such example, the composition comprises or formulated as an infant formula and/or a protein supplement. In one example, the composition is a dairy food product or a non-dairy food product. In one example, the composition is formulated as a tablet e.g., for ingestion. Alternatively, the composition is in a powder form e.g., for ingestion and/or inhalation. Alternatively, the composition is in liquid form. In one example, the composition does not include an adjuvant.

In one example, the composition according to any example described hereof is formulated for administration (e.g., by consumption) to infants, such as to infants who do not have developed lymphoid structures. For example, the composition according to any example described hereof is formulated for administration to infants aged between 0 to about 5 years, or between 0 to about 4 years, or between 0 to about 3 years, or between 0 to about 2 years, or between 0 to about 1 year. In one example the composition according to any example described hereof is formulated for administration (e.g., by consumption) to infants aged between 0 to about 2 years. In another example, the composition is formulated for administration to infants of an age between about 4 months and about 12 months or between about 4 months and about 18 months or about 4 months and about 24 months. In another example, the composition is formulated for administration (e.g., by consumption) to infants less than about 6 months of age.

In another example, the composition according to any example described hereof is formulated for administration (e.g., by consumption) to children older than about 5 years of age and/or to adolescents and/or to adults.

In another example, the composition according to any example described hereof is formulated for repeated administration, or is administered repeatedly, for example, once per week, or twice per week, or three times per week, or 4 times per week, or 5 times per week, or 6 times per week, or 7 times per week, or more than 7 times per week, or more than twice per day.

In one example, the composition according to any example described hereof is formulated or administered as a multi-dosage unit composition. For example, each dosage of the composition comprises an amount of the $H.$ $pylori$ bacteria or a lysate thereof in a range corresponding to between about $10^2$ cells to about $10^{14}$ cells, or about $10^3$ cells to about $10^{13}$ cells, or about $10^4$ cells to about $10^{13}$ cells, or about $10^5$ cells to about $10^{13}$ cells, or about $10^6$ cells to about $10^{13}$ cells, or about $10^6$ cells to about $10^{12}$ cells, or about $10^7$ cells to about $10^{11}$ cells, or about $10^8$ cells to about $10^{10}$ cells, or about $10^9$ cells to about $10^{10}$ cells. For example, each dosage of the composition comprises an amount of the $H.$ $pylori$ bacteria or a lysate thereof corresponding to about $10^8$ cells, or about $10^9$ cells, or about $10^{10}$ cells. In one example, the composition according to any example described hereof is formulated for administration daily, or is administered daily, wherein a daily dosage of said composition comprises an amount of the $H.$ $pylori$ bacteria or a lysate thereof in a range corresponding to between about $10^2$ cells to about $10^{14}$ cells, or about $10^3$ cells to about $10^{13}$ cells, or about $10^4$ cells to about $10^{13}$ cells, or about $10^5$ cells to about $10^{13}$ cells, or about $10^6$ cells to about $10^{13}$ cells, or about $10^6$ cells to about $10^{12}$ cells, or about $10^7$ cells to about $10^{11}$ cells, or about $10^8$ cells to about $10^{10}$ cells, or about $10^9$ cells to about $10^{10}$ cells. For example, each daily dosage of the composition comprises an amount of the $H.$ $pylori$ bacteria or a lysate thereof corresponding to about $10^8$ cells, or about $10^9$ cells, or about $10^{10}$ cells.

In one example, the composition according to any example described hereof is formulated for administration, or is administered, over a period of at least about 2 weeks or at least about 4 weeks or at least about 6 weeks or at least about 8 weeks or at least about 10 weeks or at least about 11 weeks or at least about 12 weeks or at least about 13 weeks at least about 14 weeks or at least about 15 weeks or at least about 16 weeks or at least about 17 weeks or at least about 18 weeks or at least about 19 weeks or at least about 20 weeks or at least about 21 weeks or at least about 22 weeks or at least about 23 weeks or at least about 24 weeks or at least about 25 weeks, or at least about 6 months, or at least about one year or more than one year. Preferably, the composition according to any example described hereof is formulated for administration, or is administered, over a period of at least about 13 weeks or at least about 3 months.

In one example, the composition according to any example described hereof is formulated for administration, or is administered, in absence of an adjuvant and/or wherein said composition does not comprise an adjuvant.

In another example, the composition or a dosage (e.g., daily dosage) of the composition according to any example described hereof promotes a balanced development of an immune system in a juvenile subject. In another example, the composition or a dosage (e.g., daily dosage) of the composition according to any example described hereof promotes acquisition of adaptive immunity and/or innate immunity in a subject. In another example, the composition or a dosage (e.g., daily dosage) of the composition according to any example described hereof promotes or enhances CD1d receptor activation and/or CD4-negative and CD8-negative natural killer (NK) cells in a subject.

In another example, the composition or a dosage (e.g., daily dosage) of the composition according to any example described hereof promotes or enhances γδ T-cell activation. In another example, the composition or a dosage (e.g., daily dosage) of the composition according to any example described hereof promotes or enhances mucosal immunity involving immune recognition and presentation to antigen-presenting cells (APCs). In another example, the composition or a dosage (e.g., daily dosage) of the composition according to any example described hereof promotes a balanced Th1/Th2 immune response to one or more allergens.

In another example, the composition according to any example described hereof comprises an amount of killed $H.$ $pylori$ cells and/or inactivated $H.$ $pylori$ cells and/or a cell lysate of said killed or inactivated cells.

The present invention clearly extends to the manufacture of a composition for use in preventing or treating allergy in a mammal, said manufacture comprising use of an isolated $H.$ $pylori$ cell, a cell lysate thereof, wherein said $H.$ $pylori$ cell is either killed or incapable of colonizing the mucosa of said mammal.

In one example, the present invention relates to use of an $H.$ $pylori$ cell such as an isolated $H.$ $pylori$ cell, and/or a cell lysate thereof or a combination thereof, wherein said $H.$ $pylori$ cell is inactivated or killed in the preparation of a composition for preventing or treating allergy in a mammal e.g., wherein the inactivated $H.$ $pylori$ cell does not have the same capacity of a live $H.$ $pylori$ cell having the same genotype to colonize the mucosa of a mammal to which it is administered or wherein the inactivated or killed $H.$ $pylori$ is incapable of colonizing the mucosa of a mammal to which it is administered. Optionally, wherein the cell lysate is a whole cell lysate (WCL) of the inactivated or killed $H.$ $pylori$ cell.

In another example, the present invention relates to use of an inactivated and/or killed $H.$ $pylori$, such as an isolated and inactivated and/or killed $H$ $pylori$, or a cell lysate thereof or a combination thereof in the preparation of a composition according to any example described hereof for interrupting or slowing or arresting or preventing an atopic march or progression of an atopic march in the subject. Optionally, wherein the cell lysate is a whole cell lysate (WCL) of the inactivated and/or $H.$ $pylori$.

In another example, the present invention relates to use of an inactivated and/or killed $H.$ $pylori$, such as an isolated and inactivated and/or killed $H.$ $pylori$, or a cell lysate thereof or a combination thereof in the preparation of a composition according to any example described hereof for delaying or preventing or interrupting or slowing the onset of one or more allergic conditions in the subject. Optionally, wherein the cell lysate is a whole cell lysate (WCL) of the inactivated and/or killed *H pylori*.

In another example, the present invention relates to use of an inactivated and/or killed *H. pylori*, such as an isolated and inactivated and/or killed *H. pylori*, or a cell lysate thereof or a combination thereof in the preparation of a composition according to any example described hereof for delaying or preventing or interrupting or slowing the onset of one or more of allergic eczema, urticaria, hives, rhinitis, wheezing, airway resistance, airway restriction, lung inflammation, food allergy, or asthma. Optionally, wherein the cell lysate is a whole cell lysate (WCL) of the inactivated and/or killed *H. pylori* cell.

In another example, the present invention relates to use of an inactivated and/or killed *H. pylori*, such as an isolated and inactivated and/or killed *H pylori*, or a cell lysate thereof or a combination thereof in the preparation of a composition according to any example described hereof for delaying or preventing or interrupting or slowing the onset of airway resistance in response to an allergen. Optionally, wherein the cell lysate is a whole cell lysate (WCL) of the inactivated and/or killed *H. pylori*.

In another example, the present invention relates to use of an inactivated and/or killed *H. pylori*, such as an isolated and inactivated and/or killed *H. pylori*, or a cell lysate thereof or a combination thereof in the preparation of a composition according to any example described hereof for delaying or preventing or interrupting or slowing the onset of lung inflammation in response to an allergen. Optionally, wherein the cell lysate is a whole cell lysate (WCL) of the inactivated and/or killed *H. pylori*.

In another example, the present invention relates to use of an inactivated and/or killed *H. pylori*, such as an isolated and inactivated and/or killed *H. pylori*, or a cell lysate thereof or a combination thereof in the preparation of a composition according to any example described hereof for delaying or preventing or interrupting or slowing the cell infiltration into lung e.g., in response to an antigen. Optionally, wherein the cell lysate is a whole cell lysate (WCL) of the inactivated and/or killed *H. pylori*.

In another example, the present invention relates to use of an inactivated and/or killed *H. pylori*, such as an isolated and inactivated and/or killed *H. pylori*, or a cell lysate thereof or a combination thereof in the preparation of a composition according to any example described hereof for delaying or preventing or interrupting or slowing the onset of an allergic condition characterized by an elevated serum level of allergen-specific IgE antibody and/or an elevated level of one or more inflammatory cytokines in bronchioalveolar lavage (BAL) and/or an elevated level of cell infiltrate in lung. Optionally, wherein the cell lysate is a whole cell lysate (WCL) of the inactivated and/or killed *H. pylori*.

Preferably, in the use according to any example described hereof, the composition is formulated for administration in absence of an adjuvant and does not include an adjuvant.

In one example, in the use according to any example described hereof, the composition is formulated for administration (e.g., by consumption) to infants, such as to infants who do not have developed lymphoid structures and/or infants aged 0 to about 5 years. For example, wherein the infants are aged between 0 to about 5 years, or between 0 to about 4 years, or between 0 to about 3 years, or between 0 to about 2 years, or between 0 to about 1 year. In one example, the infants are aged between 0 to about 2 years. In another example, the infants are aged between about 4 months and about 12 months or between about 4 months and about 18 months or about 4 months and about 24 months. In another example, the infants are less than about 6 months of age.

In one example, in the use according to any example described hereof example, the composition is formulated for administration (e.g., by consumption) to a child older than about 5 years of age and/or to adolescents and/or to adults.

In one example, in the use according to any example described hereof example, the composition is formulated for repeated administration, for example, once per week, or twice per week, or three times per week, or 4 times per week, or 5 times per week, or 6 times per week, or 7 times per week, or more than 7 times per week, or more than twice per day. In one such example, the composition is formulated as a multi-dosage unit composition. For example, each dosage of the composition comprises an amount of the *H. pylori* bacteria or a lysate thereof in a range corresponding to between about $10^2$ cells to about $10^{14}$ cells, or about $10^3$ cells to about $10^{13}$ cells, or about $10^4$ cells to about $10^{13}$ cells, or about $10^5$ cells to about $10^{13}$ cells, or about $10^6$ cells to about $10^{13}$ cells, or about $10^6$ cells to about $10^{12}$ cells, or about $10^7$ cells to about $10^{11}$ cells, or about $10^8$ cells to about $10^{10}$ cells, or about $10^9$ cells to about $10^{10}$ cells. For example, each dosage of the composition comprises an amount of the *H. pylori* bacteria or a lysate thereof corresponding to about $10^8$ cells, or about $10^9$ cells, or about $10^{10}$ cells.

In one such example, the composition is formulated for administration daily, wherein a daily dosage of said composition comprises an amount of the *H. pylori* bacteria or a lysate thereof in a range corresponding to between about $10^2$ cells to about $10^{14}$ cells, or about $10^3$ cells to about $10^{13}$ cells, or about $10^4$ cells to about $10^{13}$ cells, or about $10^5$ cells to about $10^{13}$ cells, or about $10^6$ cells to about $10^{13}$ cells, or about $10^6$ cells to about $10^{12}$ cells, or about $10^7$ cells to about $10^{11}$ cells, or about $10^8$ cells to about $10^{10}$ cells, or about $10^9$ cells to about $10^{10}$ cells. For example, each daily dosage of the composition comprises an amount of the *H. pylori* bacteria or a lysate thereof corresponding to about $10^8$ cells, or about $10^9$ cells, or about $10^{10}$ cells.

In one example, in the use according to any example described hereof example, the dosage e.g., daily dosage of the composition is to be administrated to a subject (e.g., by consumption) over a period of at least about 2 weeks or at least about 4 weeks or at least about 6 weeks or at least about 8 weeks or at least about 10 weeks or at least about 11 weeks or at least about 12 weeks or at least about 13 weeks at least about 14 weeks or at least about 15 weeks or at least about 16 weeks or at least about 17 weeks or at least about 18 weeks or at least about 19 weeks or at least about 20 weeks or at least about 21 weeks or at least about 22 weeks or at least about 23 weeks or at least about 24 weeks or at least about 25 weeks, or at least about 6 months, or at least about one year or more than one year, preferably over a period of at least about 13 weeks or at least about 3 months.

In one example, in the use according to any example described hereof, the composition or a dosage (e.g., daily dosage) of the composition promotes a balanced development of an immune system in a juvenile subject. In one example, in the use according to any example described hereof, the composition or a dosage (e.g., daily dosage) of the composition promotes acquisition of adaptive immunity and/or innate immunity in a subject. In one example, in the use according to any example described hereof, the composition or a dosage (e.g., daily dosage) of the composition promotes or enhances CD1d receptor activation and/or CD4-negative and CD8-negative natural killer (NK) cells in a subject. In one example, in the use according to any example described hereof, the composition or a dosage (e.g., daily dosage) of the composition promotes or enhances γδ T-cell activation. In one example, in the use according to any example described hereof, the composition or a dosage (e.g., daily dosage) of the composition promotes or enhances mucosal immunity involving immune recognition and presentation to antigen-presenting cells (APCs). In one example, in the use according to any example described hereof, the composition or a dosage (e.g., daily dosage) of the composition promotes a balanced Th1/Th2 immune response to one or more allergens.

In one example, in the use according to any example described hereof, the composition comprises an amount of killed *H. pylori* cells and/or inactivated *H. pylori* cells and/or a cell lysate of said killed or inactivated cells.

The present invention also clearly extends to use of the composition according to any example described hereof or to use of isolated *H. pylori* cell, a cell lysate thereof, wherein said *H. pylori* cell is either killed or incapable of colonizing the mucosa of said mammal.

In one example, the present invention provides use of the composition as described according to any example hereof in preventing or treating allergy in a subject.

In another example, the present invention provides use of the composition according to any example described hereof in interrupting or slowing or arresting or preventing an atopic march or progression of an atopic march in a subject.

In another example, the present invention provides use of the composition according to any example described hereof in delaying or preventing or interrupting or slowing the onset of one or more allergic conditions in a subject.

In another example, the present invention provides use of the composition according to any example described hereof in delaying or preventing or interrupting or slowing the onset of one or more of allergic eczema, urticaria, hives, rhinitis, wheezing, airway resistance, airway restriction, lung inflammation, food allergy, or asthma.

In another example, the present invention provides use of the composition according to any example described hereof in delaying or preventing or interrupting or slowing the onset of airway resistance in response to an allergen.

In another example, the present invention provides use of the composition according to any example described hereof in delaying or preventing or interrupting or slowing the onset of lung inflammation in response to an allergen.

In another example, the present invention provides use of the composition according to any example described hereof in delaying or preventing or interrupting or slowing cell infiltration into lung.

In another example, the present invention provides use of the composition according to any example described hereof in delaying or preventing or interrupting or slowing the onset of an allergic condition characterized by an elevated serum level of allergen-specific IgE antibody and/or an elevated level of one or more inflammatory cytokines in bronchoalveolar lavage (BAL) and/or an elevated level of cell infiltrate in lung.

In another example, the present invention provides use of a therapeutically effective amount of killed and/or inactivated *H. pylori* cells, or a cell lysate thereof or a combination thereof, in preventing or attenuating allergic airway hyper-responsiveness in lungs of a subject following exposure of the subject to an allergen. Preferably, wherein said use comprises use of a therapeutically effective amount of killed and/or inactivated *H. pylori* cells.

In another example, the present invention provides use of a therapeutically effective amount of killed and/or inactivated *H. pylori* cells, or a cell lysate thereof or a combination thereof, in preventing or attenuating allergic airway hyper-responsiveness in lungs of a subject following exposure of the subject to an allergen. Preferably, wherein said use comprises use of a therapeutically effective amount of killed and/or inactivated *H. pylori* cells.

In another example, the present invention provides use of a therapeutically effective amount of killed and/or inactivated *H. pylori* cells, or a cell lysate thereof or a combination thereof, in preventing or alleviating airway resistance in lungs of an asthmatic subject following exposure of said subject to an allergen. Preferably, wherein said use comprises use of a therapeutically effective amount of killed and/or inactivated *H. pylori* cells.

In another example, the present invention provides use of a therapeutically effective amount of killed and/or inactivated *H. pylori* cells, or a cell lysate thereof or a combination thereof, in preventing an allergic immune response to an allergen in a subject or reducing severity or incidence of an allergic immune response to an allergen in a subject. Preferably, wherein said use comprises use of a therapeutically effective amount of killed and/or inactivated *H. pylori* cells.

Preferably, in the use according to any example described hereof, the *H. pylori* or the lysate or the composition is used in absence of an adjuvant.

In yet another example, the present invention provides a method of preventing allergy in a mammal at risk of developing said allergy comprising the step of administering to said mammal an effective amount of a composition comprising an isolated *H. pylori* cell, a cell lysate thereof or combination thereof and a pharmaceutically accepted carrier, wherein said *H. pylori* cell is either killed or incapable of colonizing the mucosa of said mammal, wherein said composition, upon administration, provides protective immunity against said allergy.

Accordingly in one example, the present invention provides a method of treating or preventing allergy in a mammalian subject, said method comprising administering the composition according to any example described hereof to a subject in need thereof.

In another example, the present invention provides a method of preventing or attenuating allergic airway hyper-responsiveness in lungs of a subject following exposure of the subject to an allergen, said method comprising administering to the subject a therapeutically effective amount of killed and/or inactivated *H. pylori* cells, or a cell lysate thereof or a combination thereof, sufficient to prevent airway hyper-responsiveness in a subject following exposure of said subject to an allergen. Preferably, wherein said method comprises administering a therapeutically effective amount of killed and/or inactivated *H. pylori* cells.

In another example, the present invention provides a method of preventing or alleviating airway resistance in an asthmatic subject, said method comprising administering to a subject in need thereof a therapeutically effective amount of killed and/or inactivated *H. pylori* cells, or a cell lysate thereof or a combination thereof, sufficient to prevent airway hyper-responsiveness in lungs of the subject following exposure of said subject to an allergen. Preferably, wherein said method comprises administering a therapeutically effective amount of killed and/or inactivated *H. pylori* cells.

In another example, the present invention provides a method of preventing an allergic immune response to an allergen in a subject or reducing severity or incidence of an allergic immune response to an allergen in a subject, said method comprising administering to a subject in need thereof a therapeutically effective amount of killed and/or inactivated *H. pylori* cells, or a cell lysate thereof or a combination thereof. Preferably, wherein said method comprises administering of a therapeutically effective amount of killed and/or inactivated *H. pylori* cells.

In another example, the present invention provides a method of interrupting or slowing or arresting or preventing an atopic march or progression of an atopic march in a subject, the method comprising administering the composition according to any example described hereof to the subject.

In another example, the present invention provides a method of delaying or preventing or interrupting or slowing the onset of one or more allergic conditions in a subject, said method comprising administering the composition according to any example described hereof to the subject.

In another example, the present invention provides a method of delaying or preventing or interrupting or slowing the onset of one or more of allergic eczema, urticaria, hives, rhinitis, wheezing, airway resistance, airway restriction, lung inflammation, food allergy, or asthma in a subject, the method comprising administering the composition according to any example described hereof to the subject.

In another example, the present invention provides a method of delaying or preventing or interrupting or slowing the onset of airway resistance in response to an allergen in a subject, the method comprising administering the composition according to any example described hereof to the subject.

In another example, the present invention provides a method of delaying or preventing or interrupting or slowing the onset of lung inflammation in response to an allergen in a subject, the method comprising administering the composition according to any example described hereof to the subject.

In another example, the present invention provides a method of delaying or preventing or interrupting or slowing cell infiltration into lung of a subject in response to an allergen, the method comprising administering the composition according to any example described hereof to the subject.

In another example, the present invention provides a method of delaying or preventing or interrupting or slowing the onset of an allergic condition in a subject, wherein said condition is characterized by an elevated serum level of allergen-specific IgE antibody and/or an elevated level of one or more inflammatory cytokines in bronchioalveolar lavage (BAL) and/or an elevated level of cell infiltrate in lung of the subject, and wherein the method comprising administering the composition according to any example described hereof to the subject.

Preferably, in the method described according to any example hereof, the *H. pylori* or the lysate or the composition is administered in absence of an adjuvant, and wherein the composition does not comprise an adjuvant.

In one example of the method according to any example described hereof, the composition or the inactivated or killed *H. pylori* cells and/or the lysate thereof is administered to the subject by the oral route (i.e., for ingestion by the subject) and/or by inhumation.

In one example of the method according to any described hereof, the composition or the inactivated or killed *H. pylori* cells and/or the lysate thereof is administered (e.g., by consumption) to infants, such as infants who do not have developed lymphoid structures and/or wherein the infant is aged 0 to about 5 years. For example, the infants are aged between 0 to about 5 years, or between 0 to about 4 years, or between 0 to about 3 years, or between 0 to about 2 years, or between 0 to about 1 year. In one example, the infants are aged between 0 to about 2 years. In another example, the infants are in the age between about 4 months and about 12 months or between about 4 months and about 18 months or about 4 months and about 24 months. In another example, the infants are less than about 6 months of age.

In another example, in the method according to any example described hereof the composition or the inactivated or killed *H. pylori* cells and/or the lysate thereof is administered (e.g., by consumption) to a children older than about 5 years of age and/or to adolescents and/or to adults.

In another example, the method according to any example described hereof comprises repeated administration of the composition or the inactivated or killed *H. pylori* cells and/or the lysate thereof to the subject. In one example, the composition or the inactivated or killed *H. pylori* cells and/or the lysate thereof is administered to the subject once per week, or twice per week, or three times per week, or 4 times per week, or 5 times per week, or 6 times per week, or 7 times per week, or more than 7 times per week, or more than twice per day.

In one such example, the method according to any example described hereof comprises administering a dosage of the composition comprising an amount of the *H. pylori* bacteria or a lysate thereof in a range corresponding to between about $10^2$ cells to about $10^{14}$ cells, or about $10^3$ cells to about $10^{13}$ cells, or about $10^4$ cells to about $10^{13}$ cells, or about $10^5$ cells to about $10^{13}$ cells, or about $10^6$ cells to about $10^{13}$ cells, or about $10^6$ cells to about $10^{12}$ cells, or about $10^7$ cells to about $10^{11}$ cells, or about $10^8$ cells to about $10^{10}$ cells, or about $10^9$ cells to about $10^{10}$ cells. For example, each dosage of the composition comprises an amount of the *H. pylori* bacteria or a lysate thereof corresponding to about $10^8$ cells, or about $10^9$ cells, or about $10^{10}$ cells. In one such example, the method according of the present invention according to any described hereof, comprises administering a daily dosage of the composition, wherein the wherein the daily dosage of the composition comprises an amount of the *H. pylori* bacteria or a lysate thereof in a range corresponding to between about $10^2$ cells to about $10^{14}$ cells, or about $10^3$ cells to about $10^{13}$ cells, or about $10^4$ cells to about $10^{13}$ cells, or about $10^5$ cells to about $10^{13}$ cells, or about $10^6$ cells to about $10^{13}$ cells, or about $10^6$ cells to about $10^{12}$ cells, or about $10^7$ cells to about $10^{11}$ cells, or about $10^8$ cells to about $10^{10}$ cells, or about $10^9$ cells to about $10^{10}$ cells. For example, each daily dosage of the composition comprises an amount of the *H. pylori* bacteria or a lysate thereof corresponding to about $10^8$ cells, or about $10^9$ cells, or about $10^{10}$ cells.

In another example, the method according to any example described hereof comprises administering a daily dosage of the *H. pylori* or the lysate or composition over a period of over a period of at least about 2 weeks or at least about 4 weeks or at least about 6 weeks or at least about 8 weeks or at least about 10 weeks or at least about 11 weeks or at least about 12 weeks or at least about 13 weeks at least about 14 weeks or at least about 15 weeks or at least about 16 weeks or at least about 17 weeks or at least about 18 weeks or at least about 19 weeks or at least about 20 weeks or at least about 21 weeks or at least about 22 weeks or at least about 23 weeks or at least about 24 weeks or at least about 25 weeks, or at least about 6 months, or at least about one year or more than one year, preferably over a period of at least about 13 weeks or at least about 3 months In another example of the method according of the present invention according to any example described hereof the administration or the *H. pylori* or the lysate or composition promotes development of a balanced development of an immune system in a juvenile subject.

In another example of the method according to any example described hereof the administration or the *H. pylori* or the lysate or composition promotes acquisition of adaptive immunity in a subject.

In another example of the method according to any described hereof, the administration or the *H. pylori* or the lysate or composition promotes acquisition of adaptive immunity in a subject.

In another example of the method according to any described hereof, the administration or the *H. pylori* or the lysate or composition promotes or enhances CD1d receptor activation and/or CD4-negative and CD8-negative natural killer (NK) cells.

In another example of the method according to any described hereof, the administration or the *H. pylori* or the lysate or composition promotes or enhances γδ T-cell activation.

In another example of the method according of the present invention according to any described hereof, the administration or the *H. pylori* or the lysate or composition promotes or enhances mucosal immunity involving immune recognition and presentation to antigen-presenting cells (APCs).

In another example of the method according to any example hereof, the administration or the *H. pylori* or the lysate or composition promotes a balanced Th1/Th2 immune response to one or more allergens.

In another example of the method according to any described hereof, the subject is asymptomatic for eczema, or asymptomatic for allergy, or asymptomatic for asthma, and wherein said method prevents a subsequent onset of eczema and/or allergy and/or asthma in the subject e.g., following exposure of the subject to an allergen. In one such example, the method comprises administering an isolated and inactivated *H. pylori* to a juvenile subject to prevent eczema in the infant or a subsequent onset of allergy or asthma in later life. Alternatively, the method comprises administering the isolated and inactivated *H. pylori* to an adolescent or adult subject to prevent eczema in the subject or a subsequent onset of allergy or asthma in later life in the subject. However, a subsequent onset of eczema and/or allergy and/or asthma may be induced in an untreated subject to whom the *H. pylori* or the composition has not been administered by exposure of the untreated subject to an allergen. For example, the allergen is an environmental allergen, pollen allergen, dust mite allergen, animal allergen, or chemical allergen.

In another example of the method according to any described hereof, the subject has suffered previously from one or more incidences of allergic eczema, allergy, or asthma, and wherein said method prevents a subsequent attack or reduces severity of a subsequent attack in the subject. In one such example, the method comprises administering the inactivated and/or killed *H. pylori*, such as isolated inactivated and/or killed *H. pylori*, or a cell lysate thereof or a combination thereof, to an adolescent or adult subject that has suffered previously from allergic eczema and/or allergy and/or asthma, to thereby prevent a subsequent attack or reduce severity of a subsequent attack, optionally to prevent or slow further atopic march in the subject. Alternatively, the method comprises administering the inactivated and/or killed *H. pylori* such as isolated inactivated and/or killed *H. pylori*, or a cell lysate thereof or a combination thereof, to an adolescent or adult subject that has suffered previously from allergic eczema and/or allergy and/or asthma, to thereby prevent a subsequent attack or reduce severity of a subsequent attack, optionally to prevent or slow further atopic march in the subject. However, a subsequent attack of eczema and/or allergy and/or asthma may be inducible in an untreated subject to whom the *H. pylori* or the composition has not been administered by exposure of the untreated subject to an allergen. For example, the allergen is an environmental allergen, pollen allergen, dust mite allergen, animal allergen, or chemical allergen.

In another example of the method according to any described hereof, administration of an inactivated and/or killed *H. pylori*, such as isolated inactivated and/or killed *H. pylori*, or a cell lysate thereof or a combination thereof, to a subject reduces the incidence of allergic immune responses in a population of subjects.

In another example of the method according to any described hereof, administration of an inactivated and/or killed *H. pylori*, such as isolated inactivated and/or killed *H. pylori*, or a cell lysate thereof or a combination thereof, to a subject reduces the incidence of allergic immune responses in adolescent and/or adult members of the population treated when they were juveniles.

In some embodiments, the mammal is a naive mammal. Thus, in a further example, the present invention provides a method of preventing allergy in an immunologically naive mammal at risk of developing said allergy, said method comprising the step of: (i) identifying a mammal at risk of developing an allergy; (ii) administering to said mammal a composition comprising an isolated *H. pylori* cell, a cell lysate thereof or combination thereof and a pharmaceutically accepted carrier, wherein said *H. pylori* cell is either killed or incapable of colonizing the mucosa of said mammal and (iii) allowing sufficient time to elapse to enable energy to develop.

In a further example, the present invention provides a method of treating allergy in a mammal comprising the step of administering to said mammal an effective amount of a composition comprising an isolated *H. pylori* cell, a cell lysate thereof or combination thereof and a pharmaceutically accepted carrier, wherein said *H. pylori* cell is either killed or incapable of colonizing the mucosa of said mammal, wherein said composition, upon administration, provides protective immunity against said allergy.

The mammal or subject includes a dog, a cat, a livestock animal, a primate or a horse. In some embodiment, the mammal or subject is a human subject. Preferably, the human subject is below the age of about 5. More preferably, the human subject is below the age of 2 years.

In one example, the present invention provides a kit for treating and/or preventing allergy in a mammal comprising (i) a composition according to any example hereof and (ii) instructions for use in a method according to any one of examples hereof.

The present invention also clearly extends to a kit for treating and/or preventing allergy in a subject, said kit comprising (i) the inactivated and/or killed *H. pylori* or the lysate or the composition as described according to any example hereof, and optionally (ii) instructions for use in a method or use according to any one of examples hereof. For example, the kit is for use in preventing or attenuating allergic airway hyper-responsiveness in lungs of a subject following exposure of the subject, such as an asthmatic subject, to an allergen. Alternatively, or in addition, the kit is for use in preventing or alleviating airway resistance or airway hyper-responsiveness in lungs of an asthmatic subject following exposure of said subject to an allergen. Alternatively, or in addition, the kit is for use in preventing an allergic immune response to an allergen in a subject or reducing severity or incidence of an allergic immune response to an allergen in a subject. Alternatively, or in addition, the kit is for use in interrupting or slowing or arresting or preventing an atopic march or progression of an atopic march in a subject. Alternatively, or in addition, the kit is for use in delaying or preventing or interrupting or slowing the onset of one or more allergic conditions in a subject, for example wherein the one or more condition(s) is/are characterized by an elevated serum level of allergen-specific IgE antibody and/or an elevated level of one or more inflammatory cytokines in bronchioalveolar lavage (BAL) and/or an elevated level of cell infiltrate in lung of the subject. Alternatively, or in addition, the kit is for use in delaying or preventing or interrupting or slowing the onset of one or more of allergic eczema, urticaria, hives, rhinitis, wheezing, airway resistance, airway restriction, lung inflammation, food allergy, or asthma in a subject. Alternatively, or in addition, the kit is for delaying or preventing or interrupting or slowing the onset of airway resistance and/or lung inflammation response to an allergen in a subject. Alternatively, or in addition, the kit is for delaying or preventing or interrupting or slowing cell infiltration into lung of a subject in response to an allergen.

In a further example, the present invention provides a method of generating a *H. pylori* strain that is able to provide protective immunity against allergy comprising the steps of:
(a) providing an isolated *H. pylori* cell that is;
    (i) incapable of colonizing the mucosa of a mammal and/or
    (ii) cagA minus (cagA) and optionally positive for the toxigenic s1 and m1 alleles of the vacA gene;
(b) optionally passaging said *H. pylori* cell through an animal host; and
(c) optionally inactivating or killing said *H. pylori* cell.

Unless the context requires otherwise or specifically stated to the contrary, integers, steps, or elements of the invention recited herein as singular integers, steps or elements clearly encompass both singular and plural forms of the recited integers, steps or elements.

As used herein the term "derived from" shall be taken to indicate that a specified integer may be obtained from a particular source albeit not necessarily directly from that source.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter. Accordingly, as used herein and in the appended claims, the singular forms "a," "an," and "the" include plural reference unless the context clearly dictates otherwise. For example, a reference to "a bacterium" includes a plurality of such bacteria, and a reference to "an allergen" is a reference to one or more allergens.

Each example described herein is to be applied *mutatis mutandis* to each and every other example unless specifically stated otherwise.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention is not to be limited in scope by the specific examples described herein, which are intended for the purpose of exemplification only. Functionally-equivalent products, compositions and methods are clearly within the scope of the invention, as described herein.

All publications, patents and patent applications cited herein, whether supra or infra, are hereby incorporated by reference in their entirety. However, publications mentioned herein are cited for the purpose of describing and disclosing the protocols, reagents and vectors which are reported in the publications and which might be used in connection with the invention. Nothing herein is to be construed as an admission that the invention is not entitled to antedate such disclosure by virtue of prior invention.

BRIEF DESCRIPTION OF THE DRAWINGS

FIG. 1, panel B, shows the gradient or relative distribution of *H. pylori* in the gastrointestinal tract. *H. pylori* bacterial is a mammalian gut commensal organism that may be present in the gut alongside many other bacteria. *H pylori* is generally acquired by the oral route and colonized the gut, and may be asymptomatic in over 80% if humans, although persistent colonization of the stomach is associated with higher risk of peptic ulcers, gastric cancers and other disorders such as chronic urticarial (hives). *H. pylori* is continuously shed in large amounts from the stomach into the lower intestines where it may be taken up by the Peyer's patches and may modulate the immune system via the Peyer's patches to establish persistent gastric infection (Geritz A T and Sitaraman S V, 2007, *Gastroenterology* 133: 1044-1045; Nagi S et al., 2007, *Proc Natl Acad Sci USA* 109: 8971-8976; Watanabe N et al., 2008, *Gastroenterology* 134: 642-643). Active colonization by *H. pylori* may modulate the host immune system towards immune tolerance of *H. pylori* to allow persistent colonization, and is associated with reduce risk of allergic conditions in the host (Amedei A et al., 2010, *J Asthma Allergy.* 3:139-147; Kosunen T U et al., 2002, *Clin Exp Allergy.* 32:373-378; Chen and Blaster M J, 2007, *Arch Intern Med.* 167:821-827).

FIG. 1, panel C, shows an acute allergic asthma model using an OVA sensitization/challenge in which untreated *H.* pylori (marked "live Hp") and treated *H. pylori* i.e., inactivated and/or killed *H. pylori* (marked "killed Hp") are each administered to a mouse model of allergy and challenged at the time points indicated.

Figure 1:
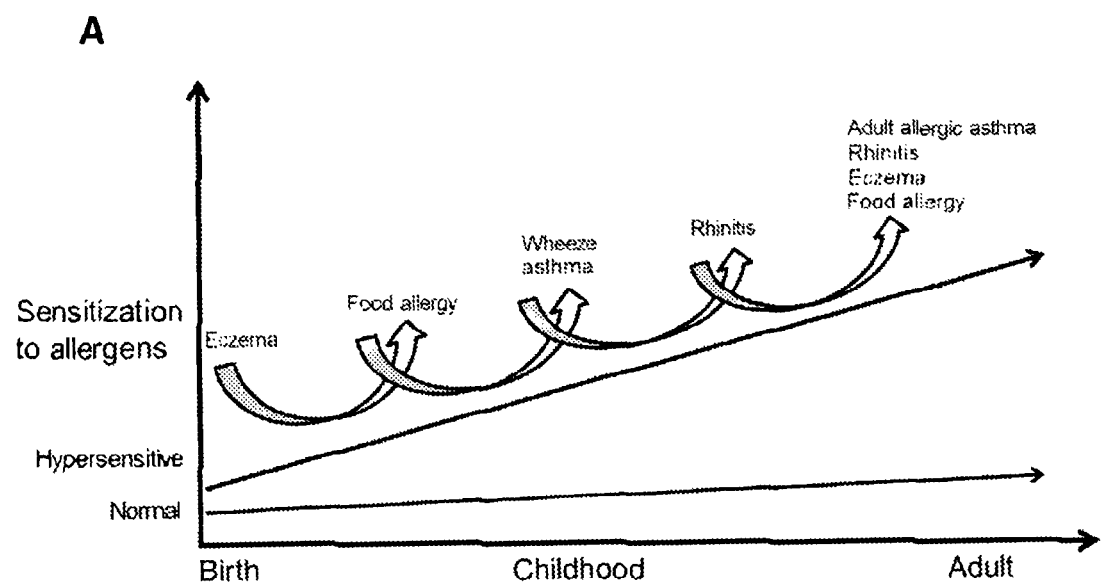
FIG. 1, panel A, shows the "allergic (or atopic) march" which refers to the typical progression of allergic diseases that often begin early in life and illustrates the relative prevalence of clinical symptoms and manifestations of allergic diseases according to age of individuals. The allergic diseases include atopic dermatitis (eczema), food allergy, allergic rhinitis (hay fever) and asthma. In general, no clinical symptoms are detectable at birth. A majority of children with eczema will progress to develop food allergies and/or allergic asthma, and a significant proportion of these individuals will have atopic or respiratory allergies as adults. Also, asthmatic wheezing may already be observed during early infancy and although the majority of early wheezers turn out to be transiently symptomatic, in some children wheezing may persist throughout school age and adolescence.
Figure 1:
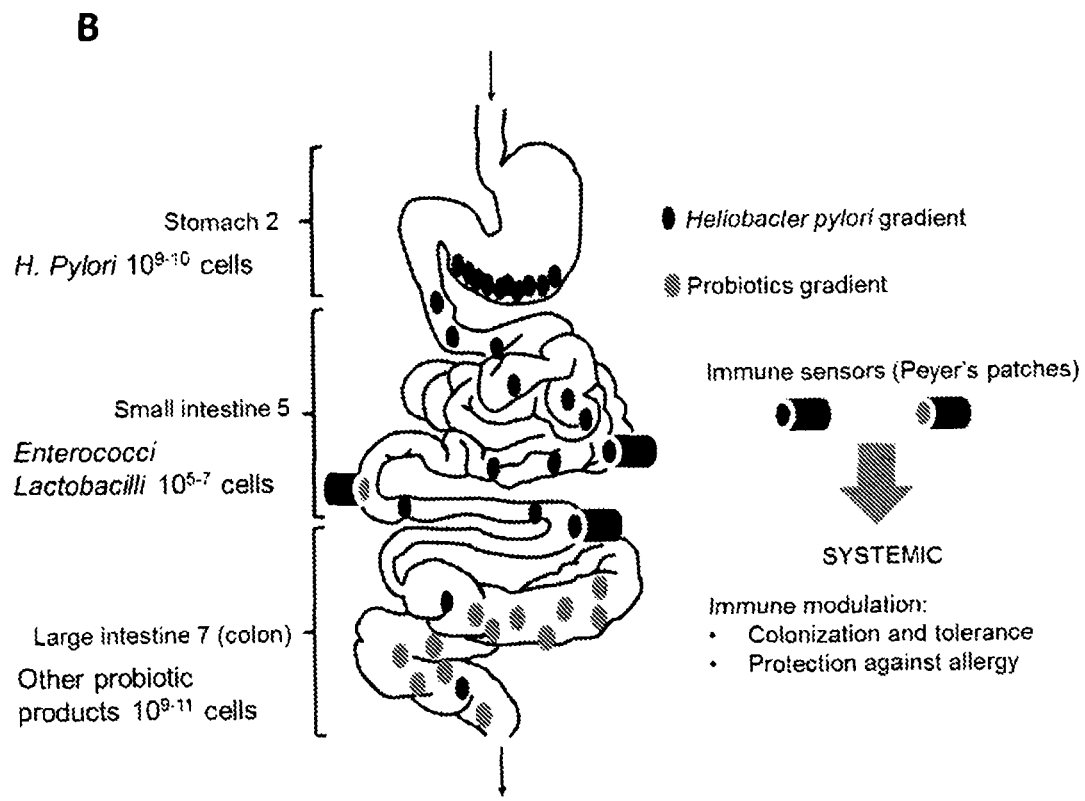
Figure 1:
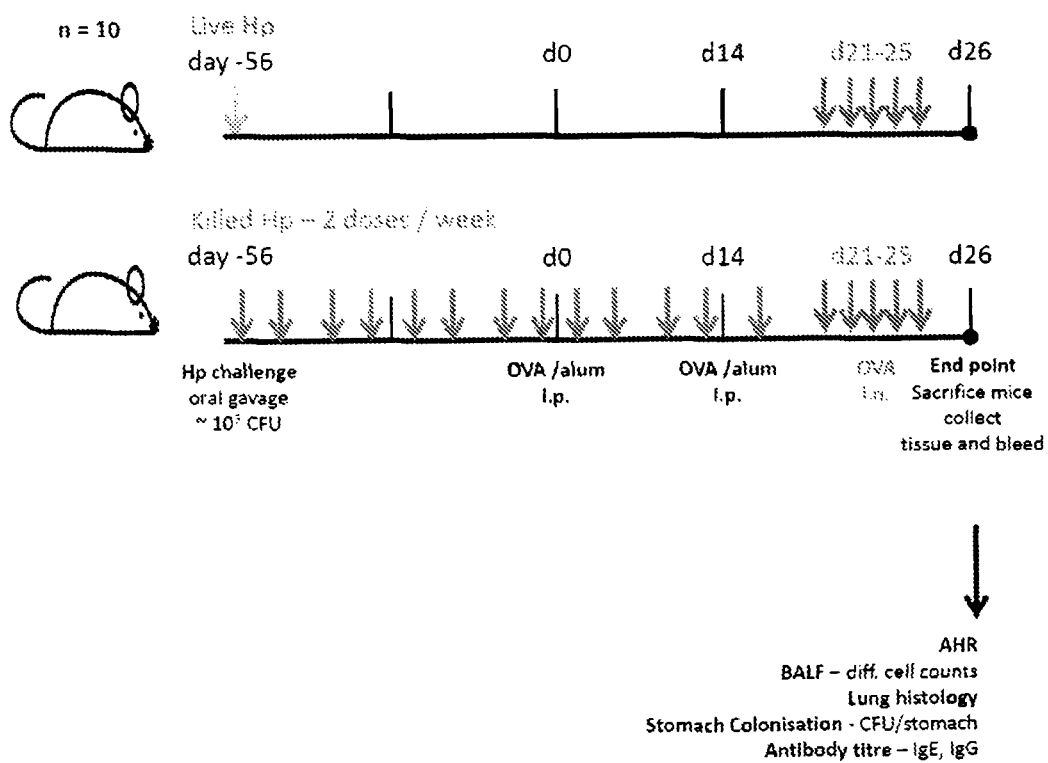
Figure 2:
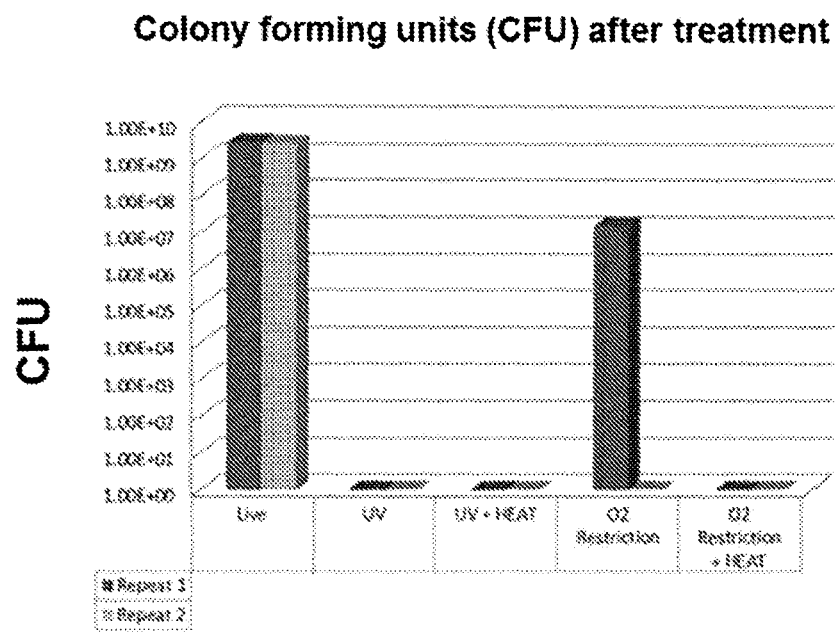

FIG. 2 shows replication efficacy of live untreated *H. pylori* OND86 control cells (marked "live") and treated *H. pylori* i.e., inactivated and/or killed *H. pylori* following treatment by UV-C irradiation (marked "UV") and optionally heat treatment (marked "UV+HEAT") or following incubation for 48 hours under anaerobic conditions (marked "$O_2$ Restriction") and optionally heat treatment (marked "$O_2$ Restriction+HEAT"). Replication efficacy of live and treated cells are determined by cells count i.e., colony forming units (CFU) measured on CBA plates after incubation of live and treated *H. pylori* i.e., inactivated and/or killed *H. pylori* for 3 days at 37° C. in a microaerobic environment containing 5% (v/v) $CO_2$ and less than 5% (v/v) $O_2$. Results obtained from two independent experiments are shown (marked "Repeat 1" and "Repeat 2").

Figure 3:
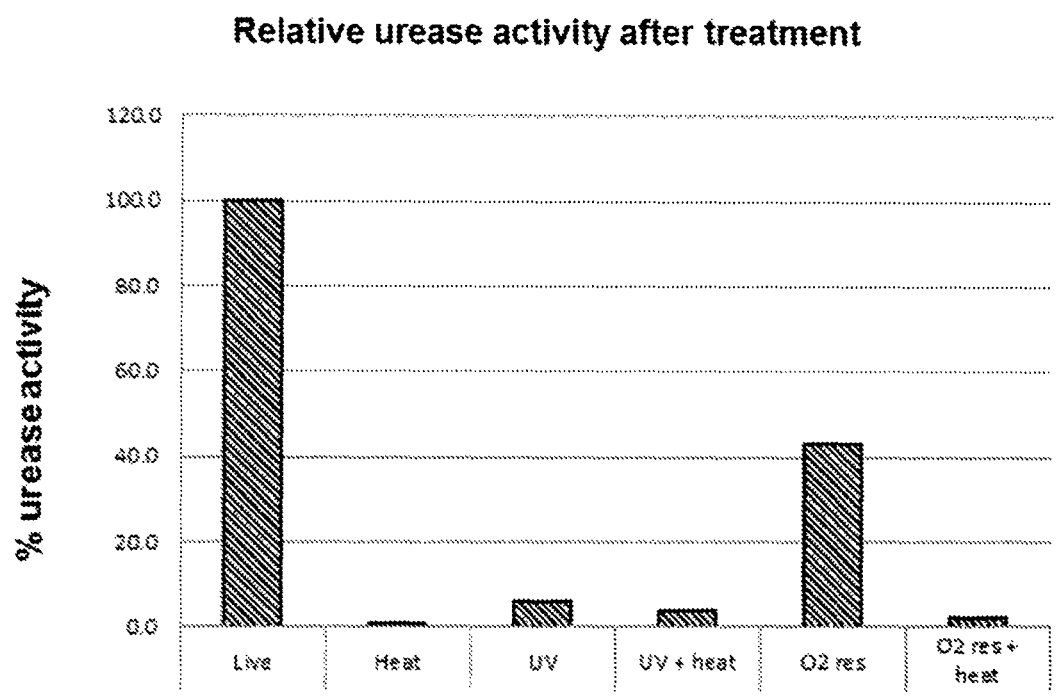

FIG. 3 shows percentage of urease activity in treated i.e., inactivated and/or killed *H pylori* following heat treatment (marked "Heat"), UV-C irradiation (marked "UV") and optionally heat treatment (marked "UV+HEAT") or following oxygen starvation (marked "$O_2$ Res") and optionally heat treatment (marked "$O_2$ Res+HEAT") relative to urease activity in untreated live *H. pylori* cells (marked "Live").

Figure 4:
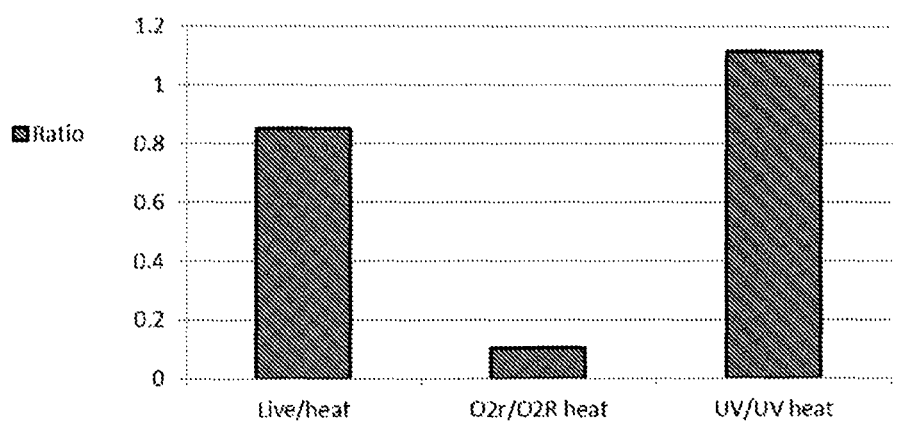

FIG. 4 shows membrane redox potential ratio of live *H pylori* cells (marked "Live") or *H. pylori* exposed to treatment by oxygen starvation (marked "O2r" or "O2R") UV-C irradiation (marked "UV") before and after heat treatment (marked "heat").

Figure 5:
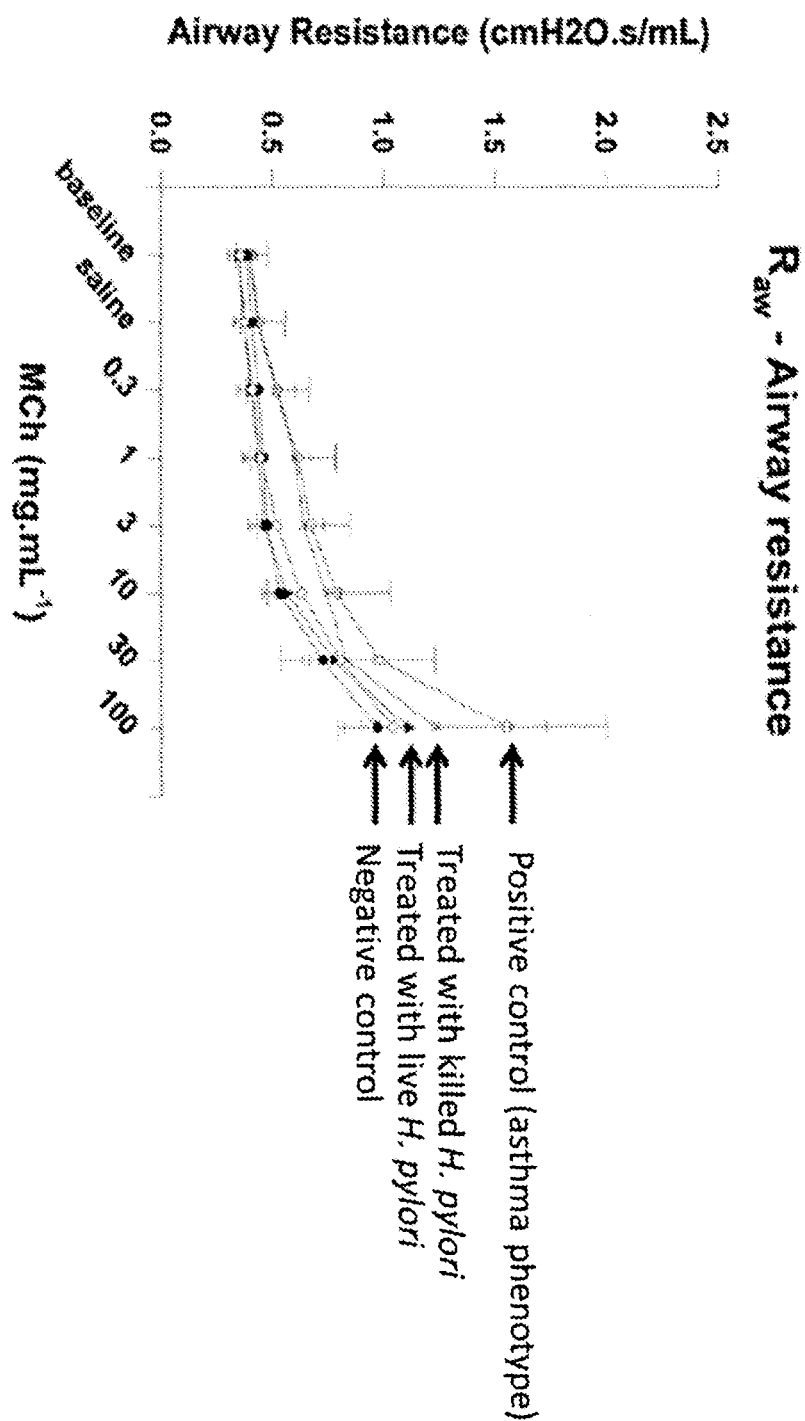

FIG. 5 shows that untreated *H pylori* (marked "live *H. pylori*") and treated *H. pylori* i.e., inactivated and/or killed *H pylori* (marked "killed *H. pylori*") each improve outcomes of allergic asthma in the OVA model of allergic airways disease.

Figure 6:
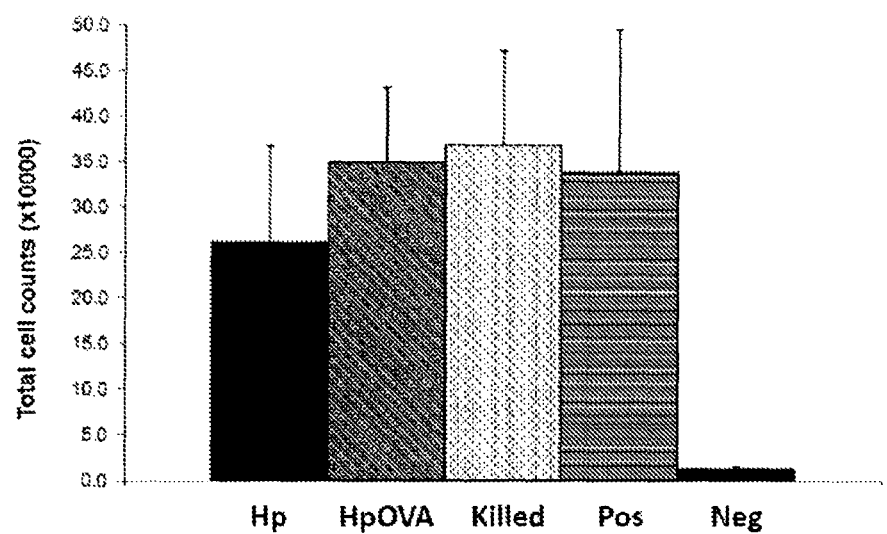
Figure 6:
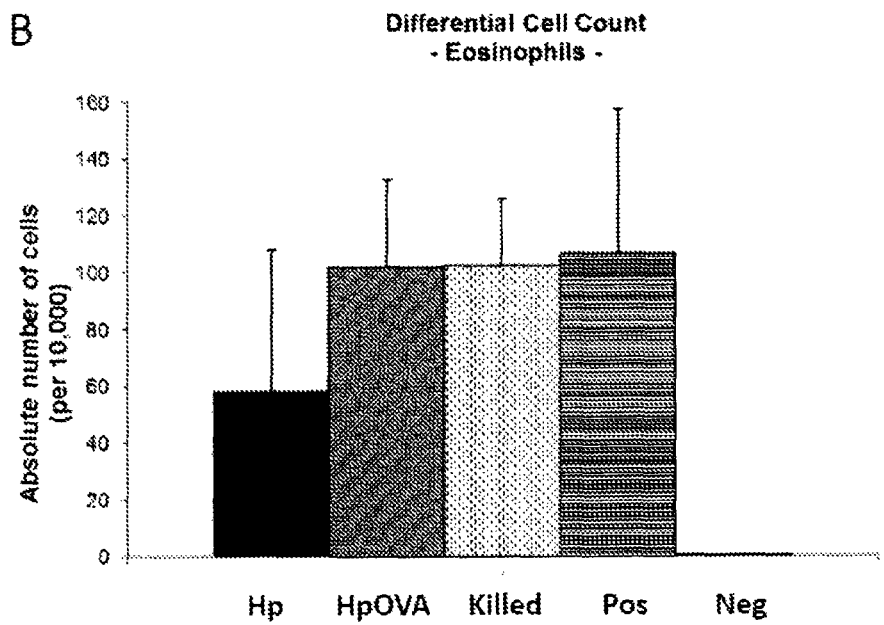

FIG. 6 shows that untreated *H. pylori* (marked "Hp") and treated *H. pylori* i.e., inactivated and/or killed *H. pylori* (marked "killed") each reduce total cell counts (panel A) and eosinophilia (panel B) in the OVA model of allergic airways disease.

Figure 7:
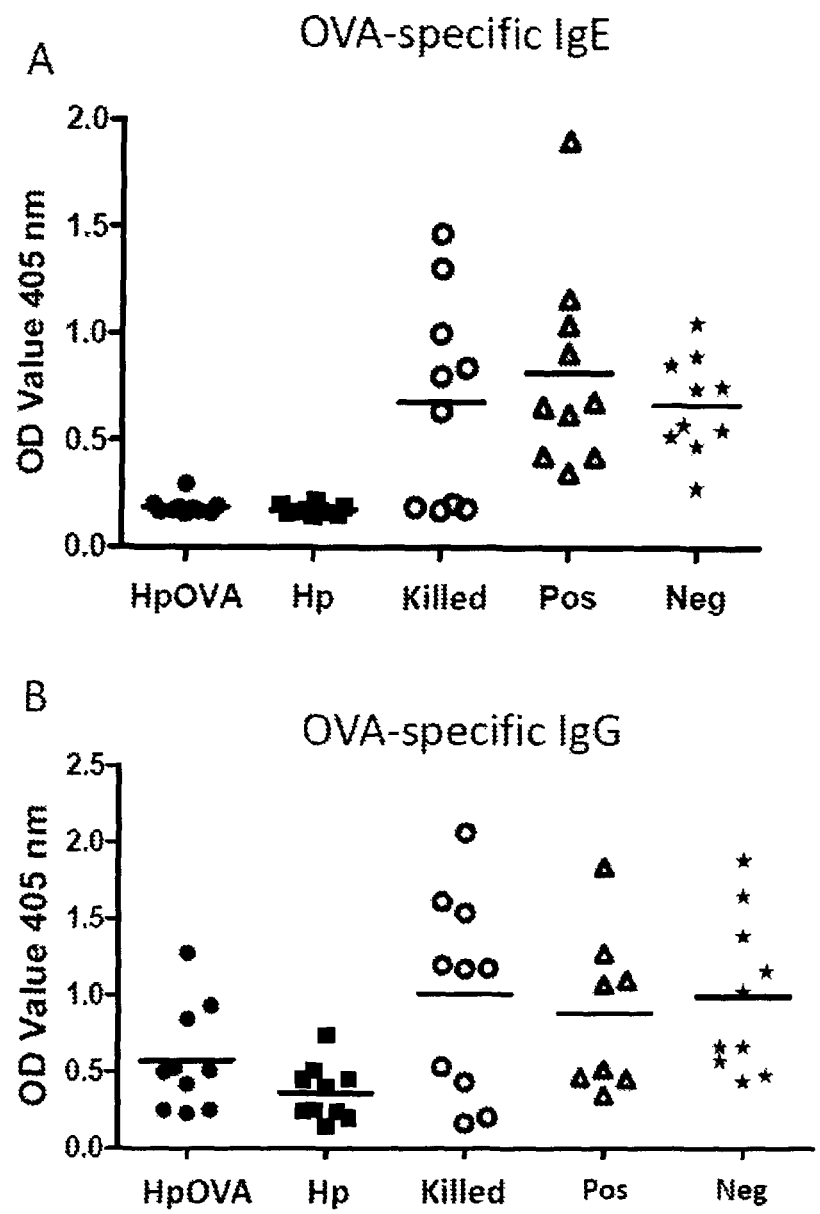

FIG. 7 shows a decreased OVA-specific IgE (panel A) and OVA-specific IgG (panel B) response in mice infected with either untreated *H. pylori* (marked "Hp") and treated *H. pylori* i.e., inactivated and/or killed *H pylori* (marked "killed") in the allergic asthma model.

Figure 8:
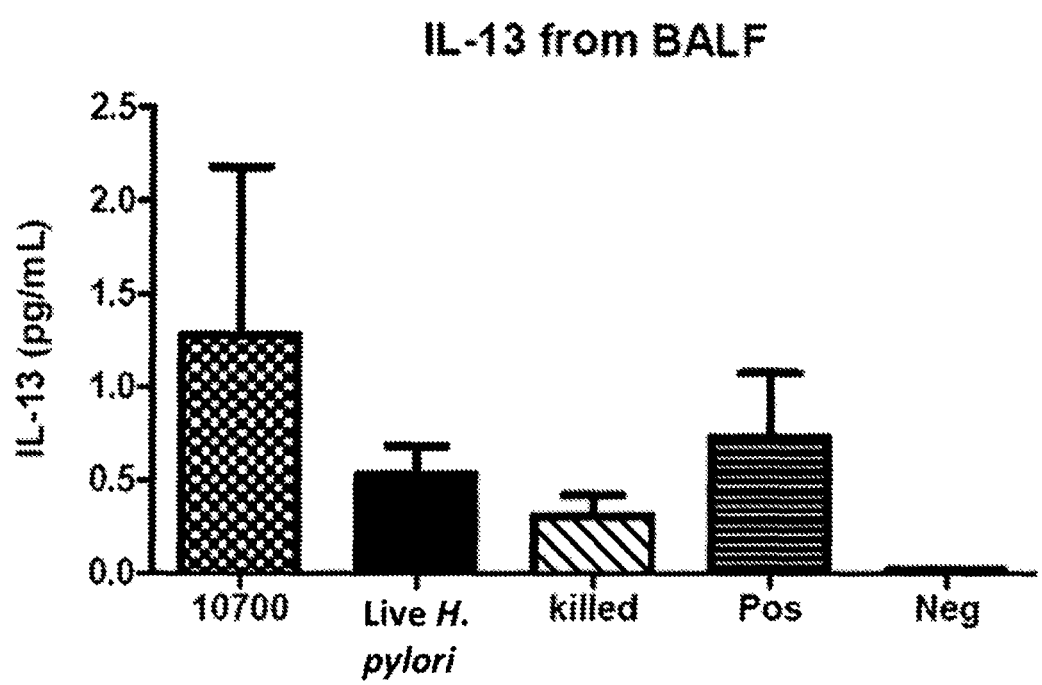

FIG. 8 shows that IL-13 is reduced in the lungs of mice infected with either untreated *H pylori* (marked "live *H pylori*") and treated *H pylori* i.e., inactivated and/or killed *H. pylori* (marked "killed") in the allergic asthma model.

Figure 9:
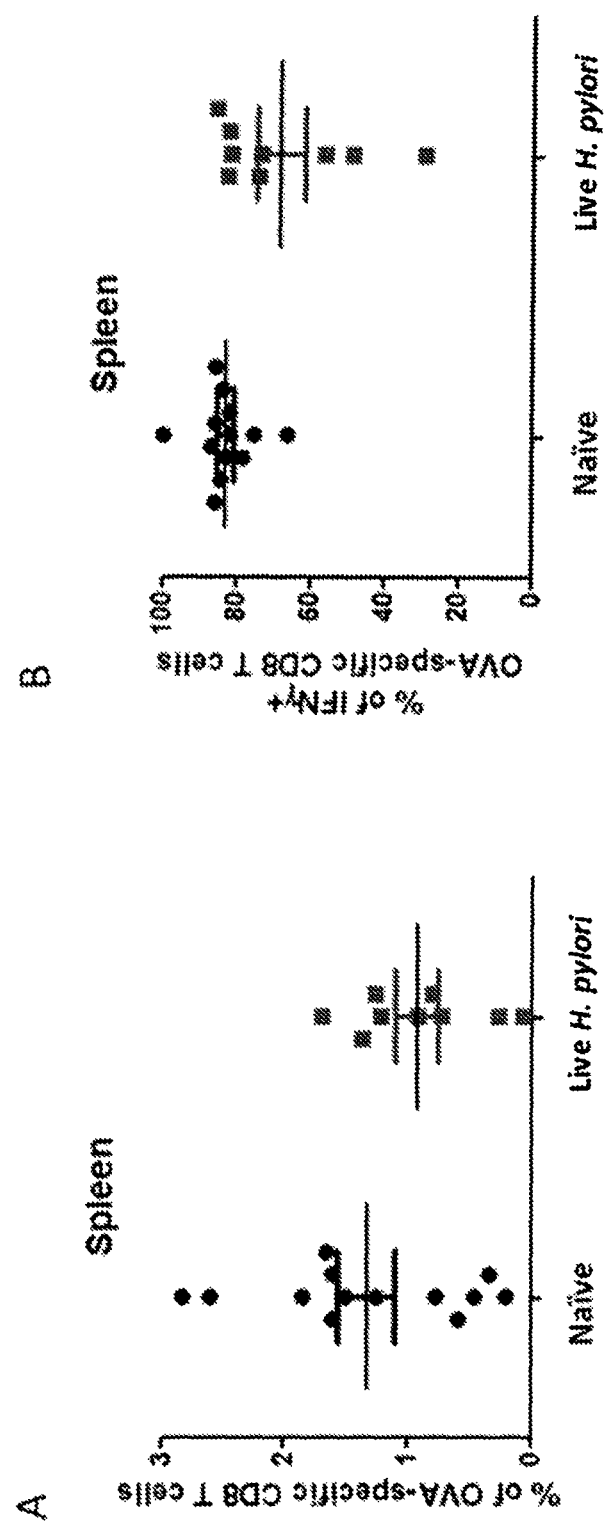

FIG. 9 shows the decreased number (panel A) and function (panel B) of OVA-specific CD8 T cells in *H. pylori* infected mice (marked "live *H. pylori*") compared to control mice (marked "naive") after OVA/alum challenge.

Figure 10:
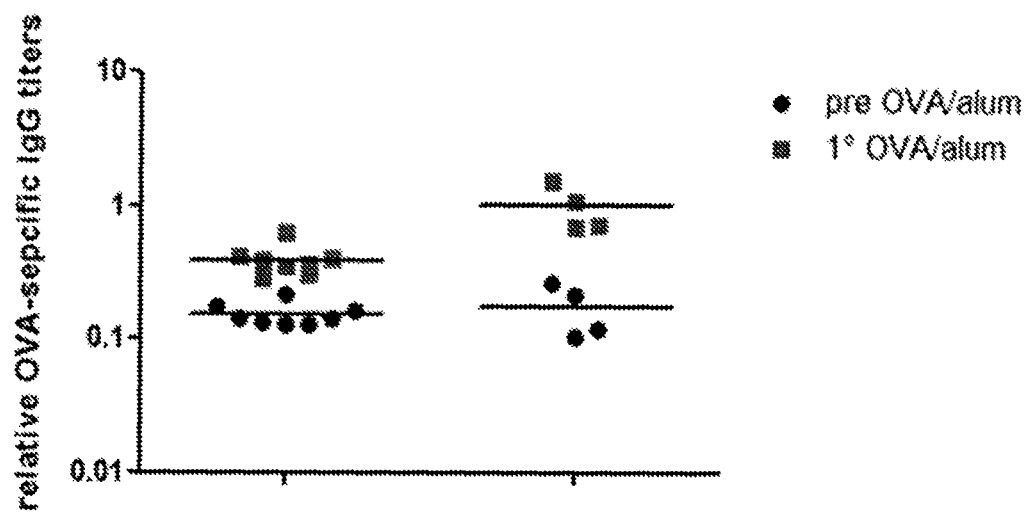
Figure 10:
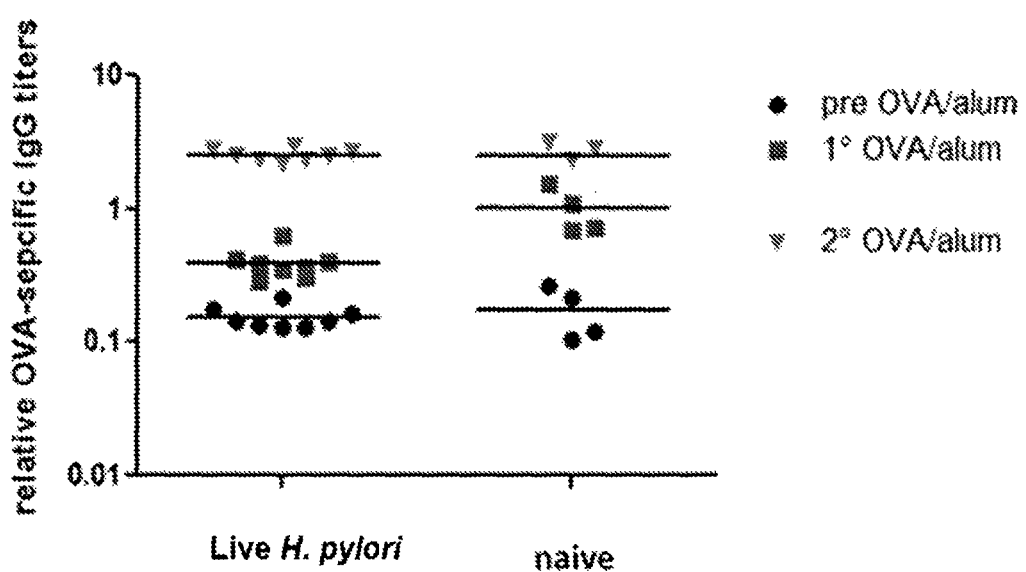

FIG. 10 shows decreased antigen-specific IgG in *H. pylori*-infected mice (marked "live *H. pylori*") compared to control mice (marked "naive"), after primary (panel A) and secondary (panel B) OVA/alum challenge.

Figure 11:
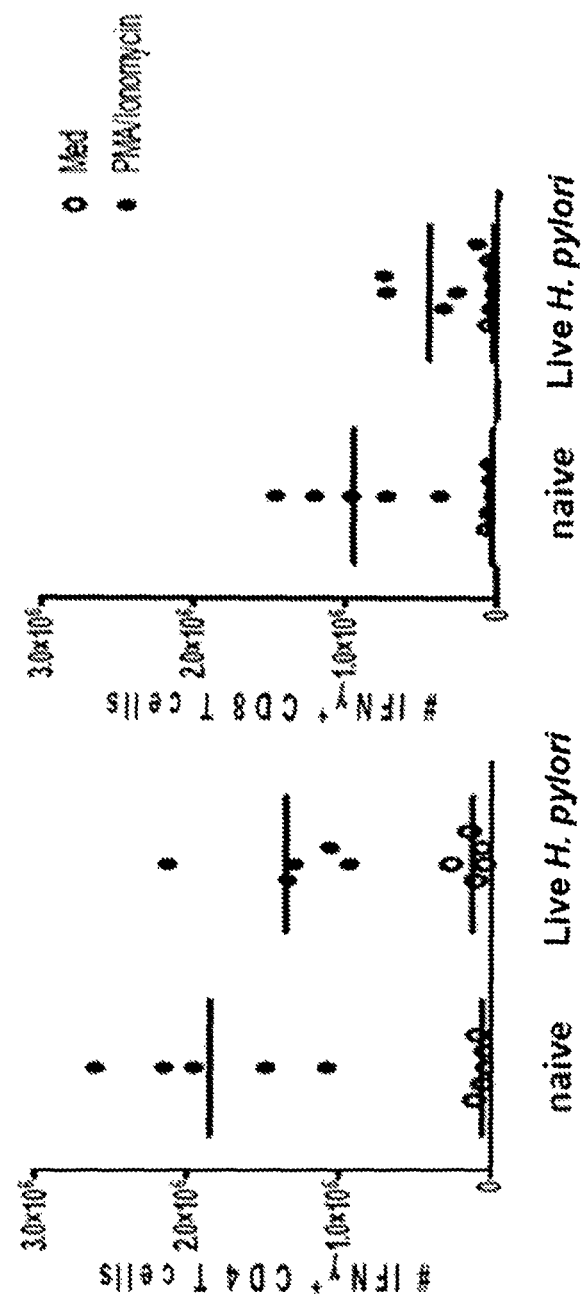

FIG. 11 shows the reduced responsiveness of CD4 (panel A) and CD8 T (panel B) cells from *H. pylori* infected mice (marked "live *H. pylori*") compared to control mice (marked "naive") in response to a non-specific stimulus.

Figure 12:
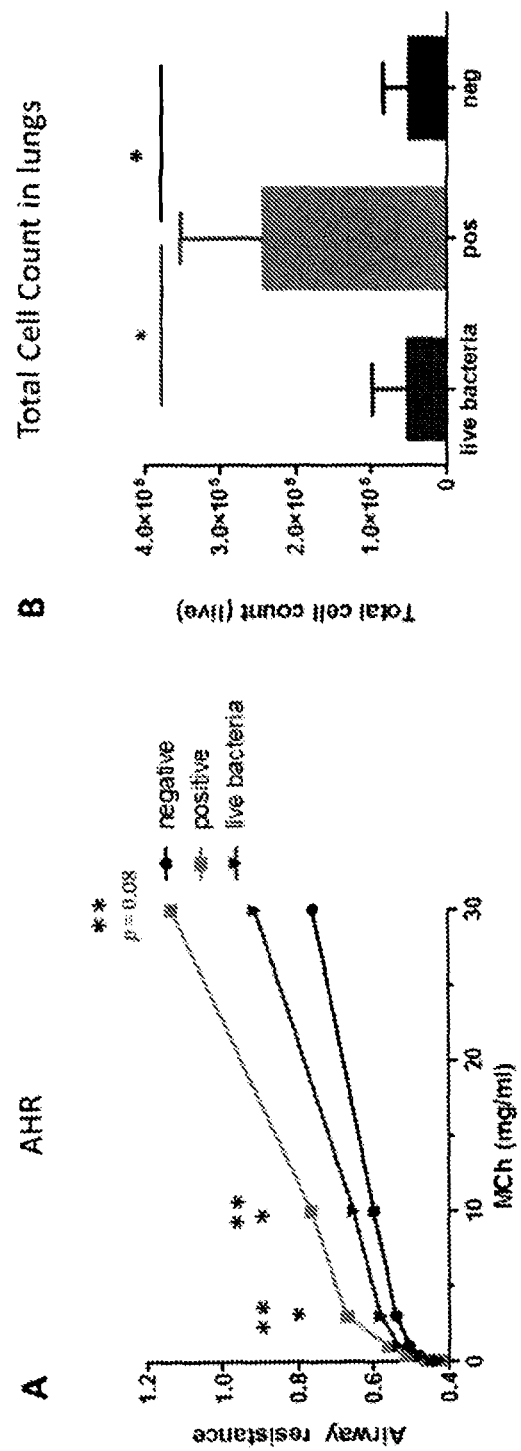

FIG. 12 shows that *H. pylori* colonisation improves outcomes of allergic airways disease in the neonatal allergic asthma model. Panel A shows that airway resistance increased in allergic adult mice not infected with live *H. pylori*, whereas mice challenged with live *H. pylori* from day 5 exhibited comparable airway resistance to that of non-allergic mice. Panel B shows that *H. pylori* colonization prevents cellular infiltration in the lungs after allergen challenge and that the total cell count was similar to non-allergic control mice.

Figure 13:
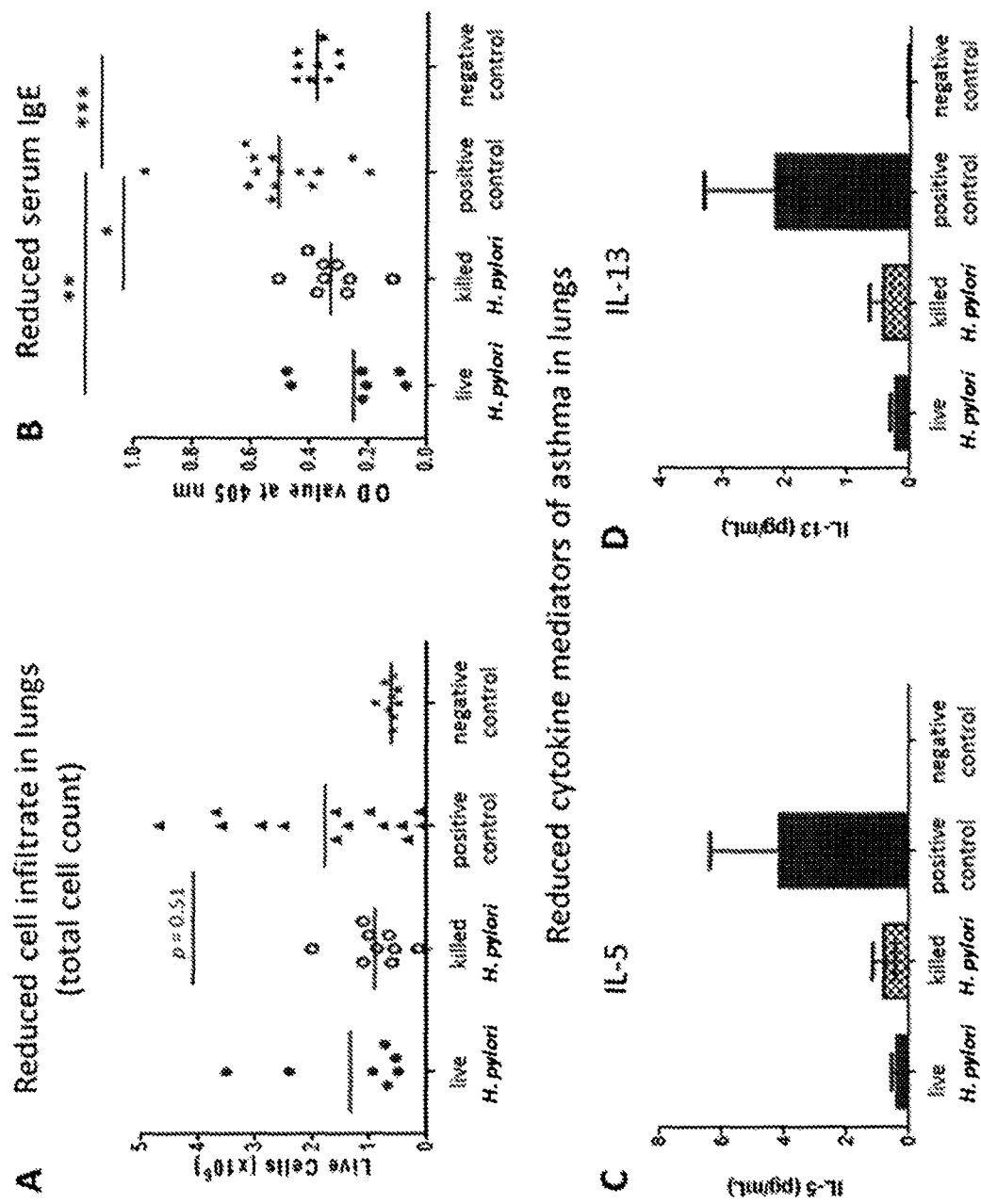

FIG. 13 shows that untreated *H. pylori* (marked "live *H. pylori*" in the x-axes) and treated *H. pylori* i.e., inactivated and/or killed *H. pylori* (marked "killed" in the x-axes) each improve immunological outcomes in the neonatal allergic asthma model. Panel A shows that administration of either treated or live *H. pylori* effectively reduced cellular infiltration in the lungs of *H. pylori* treated mice. Panel B shows that administration of either treated *H. pylori* or live *H. pylori* also reduced allergic allergen-specific IgE antibodies in *H. pylori* treated subjects. Panels C and D demonstrate that administration of treated (or live) *H. pylori* was successful in reducing production of cytokine mediators and biological markers of asthma and allergic respiratory disease, IL-5 and IL-13, in the lungs.

Figure 14:
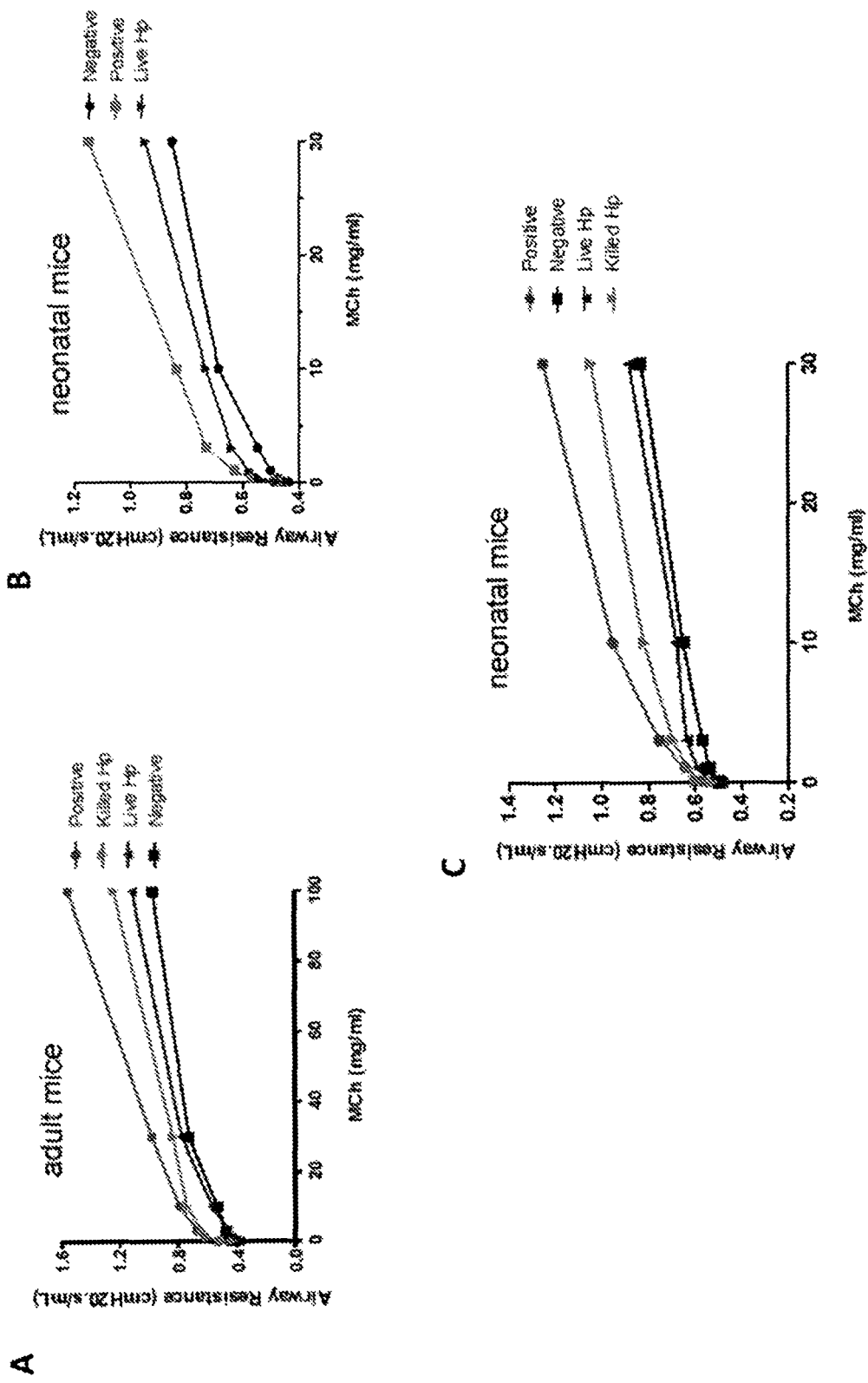

FIG. 14 shows that untreated *H. pylori* (marked "live Hp") and treated *H. pylori* i.e., inactivated and/or killed *H. pylori* (marked "killed Hp") are each effective in reducing allergic airway response to an allergen in adult and in neonatal mice. Panel A, shows results of airway hyperresponsiveness (AHR) of lung tissue in response to increasing doses of metacholine (MCh) challenge in adult mice infected with untreated *H. pylori* and treated *H. pylori* i.e., inactivated and/or killed *H. pylori*. Allergic adult mice controls which did not receive *H. pylori* i.e., were uninfected, sensitised and challenged were marked "Positive" and untreated healthy adult mice controls which did not receive *H. pylori* i.e., were uninfected and were only sensitised were marked "Negative". Panel B, shows results of airway hyperresponsiveness (AHR) of lung tissue in response to increasing doses of metacholine (MCh) challenge in neonatal mice infected with untreated *H. pylori*. Panel C, shows results of airway hyperresponsiveness (AHR) of lung tissue in response to increasing doses of metacholine (MCh) challenge in neonatal mice infected with untreated *H. pylori* and with treated *H. pylori* i.e., inactivated and/or killed *H. pylori*. In panels A and B, allergic adult neonatal mice controls which did not receive *H. pylori* i.e., were uninfected, sensitised and challenged were marked "Positive", and untreated healthy neonatal mice controls which did not receive *H. pylori* i.e., were uninfected and were only sensitised were marked "Negative". The results shown in panels A, B and C represent three independent experiments.

Figure 15:
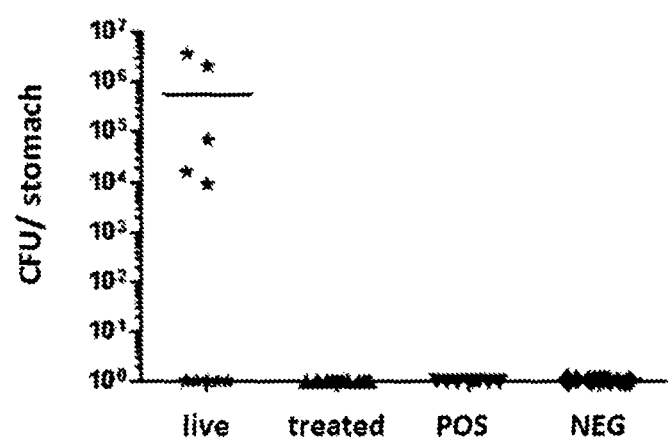

FIG. 15 shows results of colonization efficacy of untreated *H. pylori* (marked "live") and treated *H. pylori* i.e., inactivated and/or killed *H. pylori* (marked "treated") in allergic subjects in the adult allergic asthma model.

Figure 16:
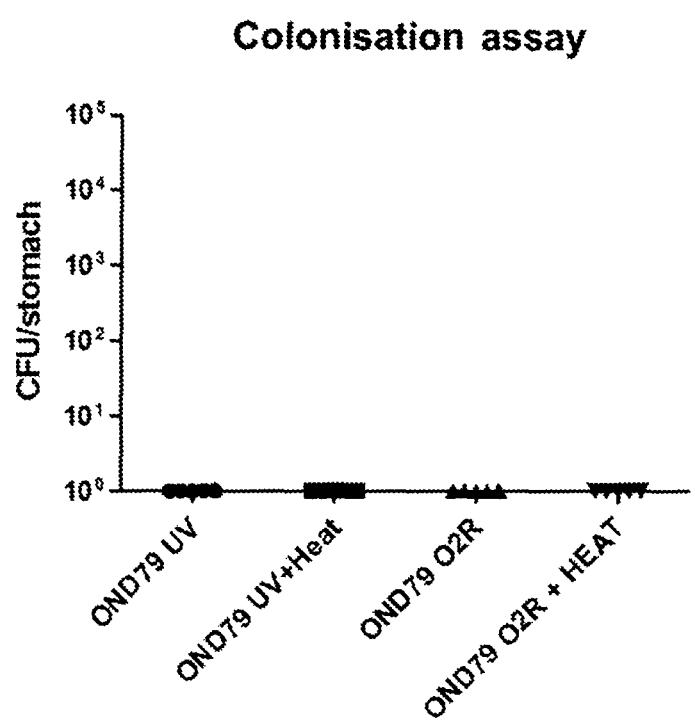

FIG. 16 shows results of colonization efficacy in mice of inactivated and/or killed *H. pylori* produced by treatment of live OND79 *H. pylori* cells with UV-C irradiation (marked "OND79 UV") and optionally heat treatment (marked "OND79 UV+HEAT") or by oxygen starvation (marked "OND79 O2R") and optionally heat treatment (marked "OND79 O2R+HEAT"). Colonization efficacy is shown as the number of colony forming unity (CFU) detected in stomach of infected mice.

Figure 17:
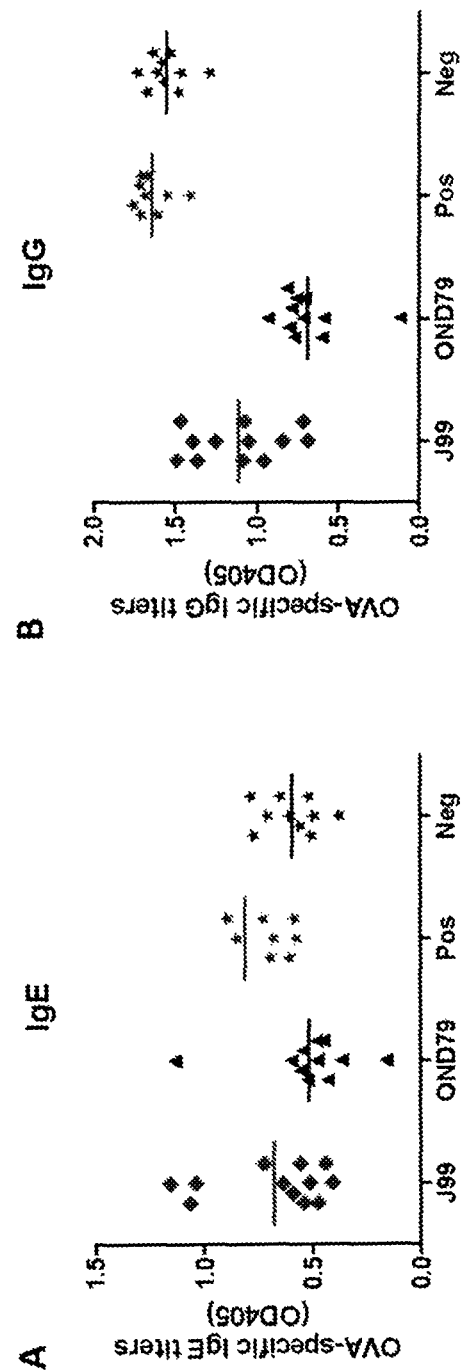

FIG. 17 shows that UV treated i.e., inactivated and/or killed *H. pylori* OND79 (marked "OND79") and *H. pylori* J99 (marked "J99") strains of different origins were effective in reducing allergen (OVA)-specific IgE (Panel A) and IgG (Panel B) antibodies in neonatal allergic asthma mouse model. Control mice were uninfected, sensitised and challenged (positive control i.e., untreated allergic mice; marked "Pos") or only sensitised (negative control i.e., untreated healthy mice; marked "Neg"). Titres of OVA-specific antibodies were measured in mice serum diluted 1:60, and expressed as the individual and average absorbance at OD405 nm.

Figure 18:
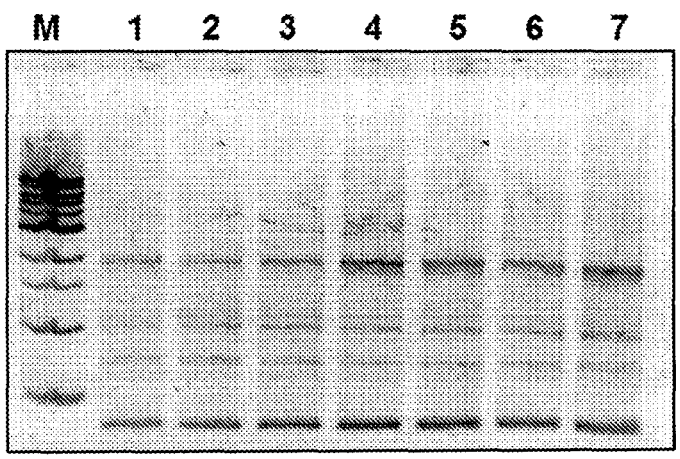
Figure 18:
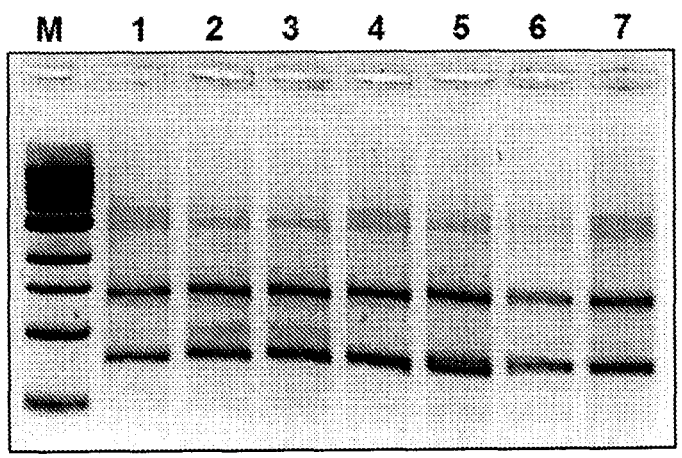

FIG. 18 shows randomly amplified polymorphic DNA (RAPD) analysis of a single colony isolate of *H. pylori* OND79 and single colony isolates six clinical isolates of a derivative *H. pylori* obtained from a gastric biopsy sample following passaging of *H. pylori* OND79 in a human host. The six clinical isolates of the derivative *H. pylori* were labelled "#1157 clone 1", "#1157 clone 9", "#86198 clone 1", "#86198 clone 9", "#45156 clone 1" and "#45156 clone 9". Genetic fingerprinting was performed as described by Akopyanz et al., (1992) *Nucleic Acids Research*, 20:5137-5142 using the primer "1254" set forth in SEQ ID NO: 3 and having the sequence 5'-CCG CAG CCA A-3' (Panel A), or the primer "1281" set forth in SEQ ID NO: 4 and having the sequence 5'-AAC GCG CAA C-3' (Panel B). In each of Panel A or Panel B: lane M, 1 kilo base (kb) DNA ladder marker (New England Biolabs Inc., Ipswich, Mass., US); lane 1, OND79 (parent strain); lane 2, #1157 clone 1; lane 3, #1157 clone 9; lane 4, #86198 clone 1; lane 5, #86198 clone 9; lane 6, #45156 clone 1; lane 7, #45156 clone 9. Genetic fingerprinting was identical for the parent input strain OND 79 and for each clinical isolate of the human-passaged derivative strain.

Figure 19:
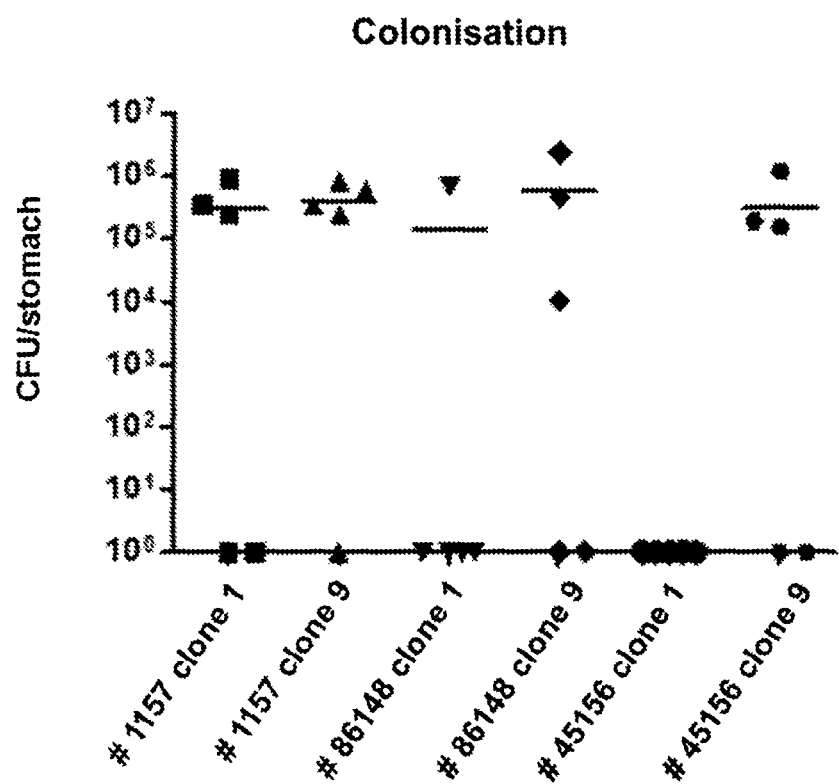

FIG. 19 shows results of infection and colonization efficacy in mice of six clinical isolates of *H. pylori* obtained after passaging *H. pylori* OND79 in a human host. Infection and colonization efficacy of the clinical isolates is shown as the number of colony forming unity (CFU) detected in stomach of infected mice. The six *H. pylori* clinical isolates are labelled "#1157 clone 1", "#1157 clone 9", "#86198 clone 1", "#86198 clone 9", "#45156 clone 1" and "#45156 clone 9". The *H. pylori* clinical isolate #1157 clone 9 corresponds to *H. pylori* OND86 strain deposited under NMI Accession No. V14/013016.

Figure 20:
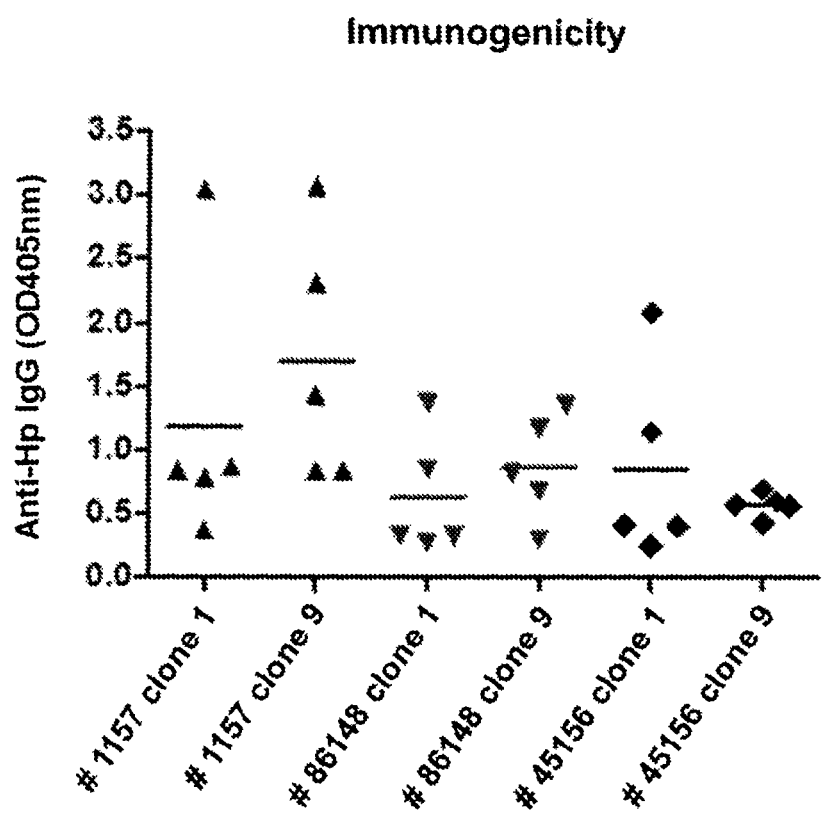

FIG. 20 shows efficacy of six clinical isolates of *H. pylori* obtained after passaging *H. pylori* OND79 in a human host, to induce specific anti-*H. pylori* IgG antibody response 2 weeks after oral administration of the isolates in the C57BL/6 mouse model. Antibody response titres are expressed as the OD value measured at 405 nm. The six *H. pylori* clinical isolates are labelled "#1157 clone 1", "#1157 clone 9", "#86198 clone 1", "#86198 clone 9", "#45156 clone 1" and "#45156 clone 9". The *H. pylori* clinical isolate #1157 clone 9 corresponds to *H. pylori* OND86 strain deposited under NMI Accession No. V14/013016.

Figure 21:
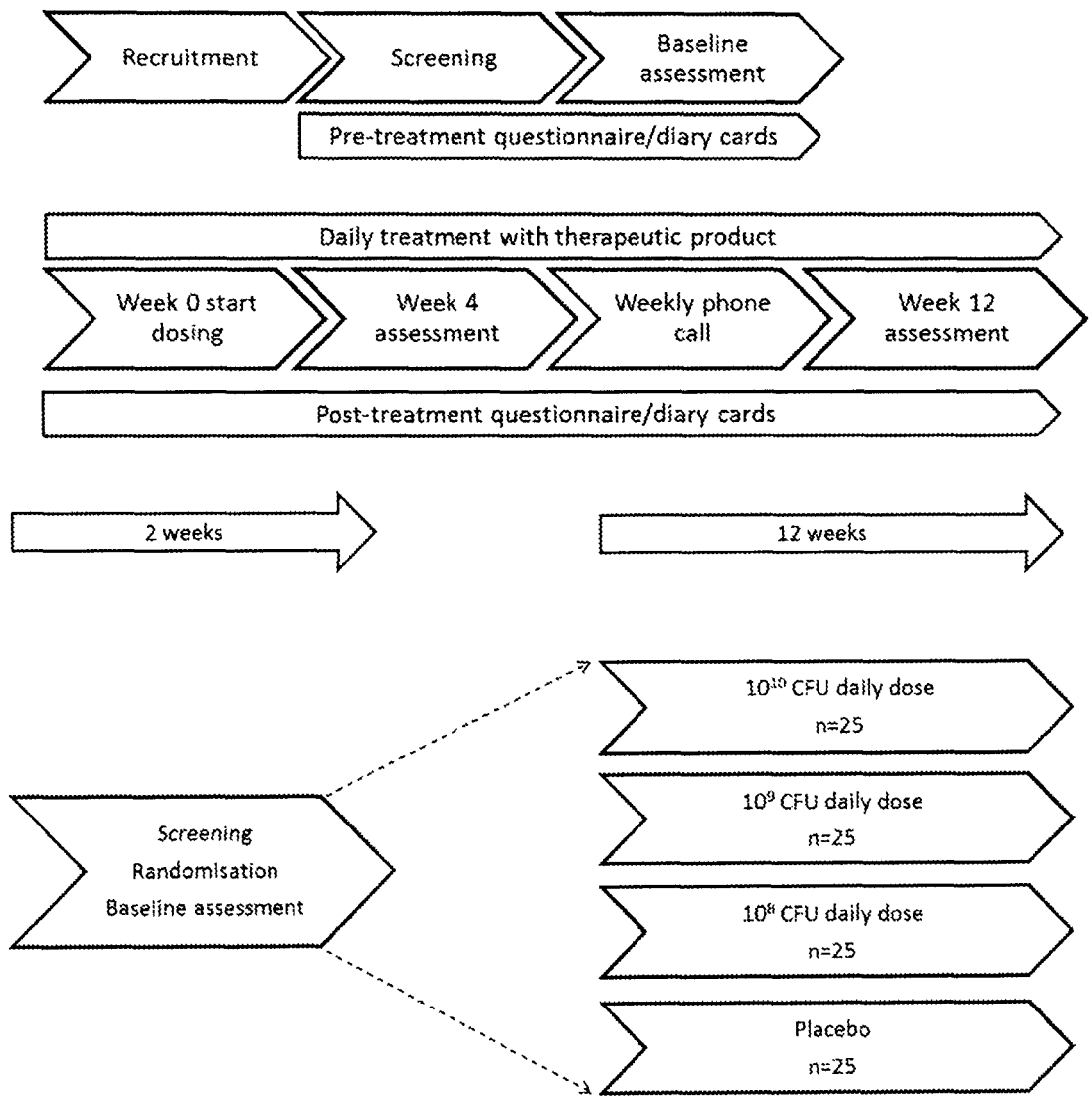

FIG. 21 shows safety and tolerability study in allergic adult subjects including a dose escalation assessment.

DETAILED DESCRIPTION OF THE PREFERRED EMBODIMENTS

1. *H. pylori*

The present invention provides for compositions comprising inactivated and/or killed *H. pylori* or a cell lysate thereof.

In one example, the *H. pylori* is an inactivated *H. pylori*. The term "inactivated *H. pylori*" shall be taken to mean a cell or strain of *H. pylori* which does not have the same capacity of a live *H. pylori* bacterium having the same genotype to induce gastric ulcer or other pathology such as a malignancy and/or does not have the same colonization capability of a live bacterium *H. pylori* bacterium having the same genotype and/or does not have a functional or intact genome of a live *H. pylori* bacterium having the same genotype. For example, an inactivated *H. pylori* may not have an intact genome yet retain a functional transcriptome and/or translational machinery such that it retains at least portion of the metabolic activity of the corresponding live *H. pylori*. Thus, it is preferred that an inactivated *H. pylori* retains partial or full metabolic activity of a corresponding live *H. pylori*. By "live *H. pylori*" in this context is meant *H. pylori* that has not been treated as described according to any example hereof so as to render it inactive and/or killed.

Notwithstanding that an inactivated *H. pylori* may transiently associate with the gastric mucosa of a mammal, it is preferred that such inactivated bacteria are incapable of colonizing the gastric mucosa of a mammal so as to establish chronic or persistent infection of the gastric mucosa. For example, inactivated *H. pylori* may have an impaired ability to induce one or more *H. pylori*-associated pathogenic effects including, but not limited to, formation of peptic ulcers, gastric cancers such as non-cardiac gastric adenocarcinoma or MALT lymphoma, and other disorders such as chronic urticarial (hives) that is normally associated with persistent *H. pylori* colonization of the mucosa.

Preferably, an inactivated *H. pylori* retains the cell structure of live *H. pylori*. For example, an inactivated *H. pylori* retains the structural integrity of the bacterial cell wall and/or cell membrane of live *H. pylori* such that it may not be disrupted or lysed.

Alternatively, or in addition, the inactivated *H. pylori* retains an ability of a live *H. pylori* to be taken up by the Peyer's patches in the lower intestine of a mammal. For example, the inactivated *H. pylori* may retain the immunogenicity and/or antigenicity and/or receptor-ligand interaction of a corresponding live *H. pylori* having replicative and colonizing functionalities.

Alternatively, or in addition, an inactivated *H. pylori* undergoes one or more metabolic changes e.g., enhanced lipopolysaccharide synthesis and surface presentation thereof and/or enhanced degradation of cellular proteins and/or reduced urease production during and/or following their inactivation.

In another example, the *H. pylori* is a killed *H. pylori*. The term "killed *H pylori*" shall be taken to mean a cell or strain of *H. pylori*, which is irreversibly metabolically inactive. For example, a killed *H. pylori* is incapable of inducing gastric ulcer or other pathology such as a malignancy and/or is incapable of colonizing the gastric mucosa of a mammal and/or does not have a functional or intact genome of a live *H. pylori* bacterium having the same genotype. Thus it is preferred that a killed *H. pylori* does not retain a functional transcriptome and/or translational machinery.

Preferably, a killed *H. pylori* retains the cell structure of an a live *H. pylori*. For example, a killed *H. pylori* retains the structural integrity of the bacterial cell wall and/or cell membrane of an inactivated or live *H. pylori* such that it may not be disrupted or lysed.

Alternatively, or in addition, a killed *H. pylori* retains the ability of a live *H. pylori* to be taken up by the Peyer's patches in the lower intestine of a mammal. For example, the killed *H. pylori* may retain the immunogenicity and/or antigenicity and/or receptor-ligand interaction of a corresponding live *H. pylori* having replicative and colonizing functionalities.

In another example, the present invention employs *H. pylori* that has been subjected to a process for inactivating the bacterium and a process for killing *H. pylori*. For example, killing of cells captures the benefits of the inactivated cells to the immune system following their administration whilst ensuring added safety of the organism for human use.

In the present context, a "cell lysate" is a preparation made from inactive and/or killed *H. pylori* cells as described according to any example hereof in which the inactive and/or killed *H. pylori* cells have been disrupted such that the cellular components of the bacteria are disaggregated or liberated from the bacterial cell.

Persons skilled in the art are aware of means for producing bacterial cell lysates. For example, *H. pylori* cells are pelleted and then resuspended in, for example, Dulbecco's phosphate buffered saline (PBS; 10 mM phosphate, 0.14 M NaCl, pH 7.4) and subjected to sonication on ice with a W-375 sonication Ultrasonic processor (Heat Systems-Ultrasonics, Inc., Farmingdale, N.Y.) at 50% duty cycle with pulse and strength setting 5 for three 1 min sessions. If required, insoluble material and unbroken bacterial cells can then be removed by centrifugation. Alternatively, *H pylori* cells are pelleted and then resuspended in a lysis buffer containing 25 mM Tris, pH 7.5, 1 mM $MgCl_2$, 1 mM aminopolycarboxylic acid (EGTA), 150 mM NaCl, 1% v/v nonyl phenoxypolyethoxyl ethanol (e.g., Tergitol-type NP-40 from Sigma-Aldrich Inc.,) and 1% v/v protease and/or phosphatase inhibitor(s). The whole cell lysate is collected e.g., using a cell scraper and centrifuged at 1,200 g, 4° C. for 15 min. Alternatively, *H. pylori* cells are collected by centrifugation and resuspended in PBS and then lysed by passage through a French press (SLM Instrument Inc., Urbana, Ill.) at 20,000 LB/in. Again, if required, the bacterial lysate are centrifuged at 102,000×g for 10 minutes to remove bacterial debris and/or filtered through a 0.45 µM membrane (Nalgene, Rochester, N.Y.). Another method of producing cell lysate of *H. pylori* involves one or more cycles of freezing and thawing of bacterial pellets e.g., in the presence of lysozyme. A particular example of a *H. pylori* cell lysate is the soluble fraction of a sonicated culture of the inactivated *H. pylori*, e.g., obtained after filtration. Alternatively or in addition, *H. pylori* cells are fragmented using a high-pressure homogenizer (e.g., Avestin model EmulsiFlexC5). Optionally, the cell lysate is further treated using formalin. In one example, the whole cell lysate (WCL) of *H. pylori* e.g., obtained as described herein, is subjected to additional fractionation and/or purification to isolate or purify or separate one or more components from the *H. pylori* cell lysate, such as cell proteins and/or lipids.

In another example, the live and/or inactivated and/or killed *H. pylori* may be in an isolated form. As used herein the term "isolated" when used in reference to *H. pylori* such as live and/or inactivated and/or killed *H. pylori* refers to *H. pylori* or cell or strain thereof present in an environment which is different to the native environment in which a live *H. pylori* is naturally present. For example, the isolated *H. pylori* may be removed or isolated from its native environment and/or substantially free of at least one component found in the native environment of a live *H. pylori*. The term "isolated" in this context includes a *H. pylori* cell culture, a partially-pure *H. pylori* cell preparation, and a substantially pure *H. pylori* cell preparation.

In one particular example, *H. pylori* is provided in biologically-pure form. As used herein the term "biologically-pure" refers to an in vitro or ex vivo culture of *H. pylori* that is substantially free from other species of microorganisms. Optionally, a biologically-pure *H. pylori* is in form of a culture of a single strain of *H. pylori*.

In yet another example, a killed and/or inactivated H pylon may comprise a cell lysate. For example, the cell lysate may be a whole cell lysate of *H. pylori*.

Alternatively, the present invention is employed using a composition comprising a mixture of the inactivated and/or killed *H. pylori* as described according to any example hereof and a cell lysate, such as a whole cell lysate of an inactivated and/or killed *H. pylori* as described according to any example hereof.

2. Cultivating *H. pylori*

Strains

Any *H. pylori* strain known in the art may be used in the preparation of the *H. pylori* compositions of the present invention. In one example, the *H. pylori* strain may be any live *H. pylori* strain deposited with an International Depositary Authority under the Budapest Treaty on the International Recognition of the Deposit of Microorganisms for the Purpose of Patent Procedure. For example, the *H. pylori* strain may be obtained from the American Type Culture Collection (ATCC) such as, for example, *H. pylori* deposited under Accession No. ATCC 43504 or Accession No. ATCC 26695 or Accession No. ATCC BAA-945 or Accession No. ATCC 700392 or Accession No. ATCC 49503 or Accession No. ATCC 53726 or Accession No. 53727 or Accession No. ATCC 43526 or Accession No. ATCC: 43579 or accession number ATCC 700824. For example, *H. pylori* strain may be J99 stain (ATCC 700824). Alternatively, or in addition, exemplary *H. pylori* strains are as described by Moodley Y et al., (2009), Science, 323: 527-530 and/or by Falush D, et al., (2003), Science, 299: 1582-1585. Alternatively, or in addition, exemplary *H. pylori* strains that may be used in the preparation of the compositions of the present invention were deposited with the National Measurement Institute (NMI), 1/153 Bertrie Street, Port Melbourne, Victoria, Australia, pursuant to the provisions of the Budapest Treaty as follows:

| *H. pylori* strain name | NMI Accession No | Date of deposit |
| --- | --- | --- |
| OND737 | V09/009101 | 22 Apr. 2009 |
| OND738 | V09/009102 | 22 Apr. 2009 |
| OND739 | V09/009103 | 22 Apr. 2009 |
| OND740 | V09/009104 | 22 Apr. 2009 |
| OND248 | V10/014059 | 28 May 2010 |
| OND256 | V10/014060 | 28 May 2010 |
| OND79 | V13/023374 | 28 Nov. 2013 |
| OND86 | V14/013016 | 10 Jun. 2014 |

In another example, the *H. pylori* may be any *H. pylori* clinical isolate obtained from mammalian e.g., human gastric biopsy samples from patients diagnosed to be infected with *H. pylori* such as those exhibiting chronic gastritis, peptic ulcers e.g., gastric and duodenal ulcers, and/or gastric malignancies. In one such example, the *H. pylori* bacteria in the patient biopsy is inoculated onto a suitable culture medium such as Columbia agar containing 5% sheep blood (Invitrogen) and grown at 37° C. in a microaerophilic chamber (Don Whitley, West Yorkshire, UK) in 10% $CO_2$, 5% $O_2$, and 85% $N_2$; for example as described by Cheng-Chou Yu et al., (2013), PLoS ONE, 1: e55724. In another example, the *H. pylori* bacteria in the patient biopsy is inoculated onto *H. pylori* selective media such as F12 agar medium plates comprising DENT's supplement, nalidixic acid and bacitracin e.g., commercially available from Thermoscientific, Australia. In one such example the *H. pylori* strain is TA1 (Cag+ and VacA+) as described by Cheng-Chou Yu et al., (2013) supra.

Accordingly, in some examples, the *H. pylori* strain of the present invention has been passaged through an animal host such as a human. For example, the *H. pylori* strain of the present invention is derived from the *H. pylori* strain OND79 after passage of the OND79 strain in a human subject e.g., following infection and/or colonization of the gastric mucosa of a human subject with *H. pylori* OND79 strain. In one such example the *H. pylori* strain is obtained from a human gastric biopsy sample of a human subject who has been administered with OND79 cells. For example, the *H. pylori* strain of the present invention is OND86.

Culture Media

Media used for cultivating *H. pylori* for bacterial growth and/or maintenance are prepared by procedures known to the skilled artisan and described, for example, in BD Diagnostics (*Manual of Microbiological Culture Media*, Sparks, Md., Second Edition, 2009); Versalovic et al. (In *Manual of Clinical Microbiology*, American Society for Microbiology, Washington D.C., 10th Edition, 2011), Garrity et al. (In *Bergey's Manual of Systematic Bacteriology*, Springer, New York, Second Edition., 2001); Ndip et al. 2003 *J. Pediatr. Gastroenterol. Nutr.* 36: 616-622 and Testerman et al. 2001 *J. Clin. Microbiol.* 39: 3842-3850. As will be apparent to the skilled artisan, *H. pylori* morphology may be assessed by performing gram staining (See e.g. Coico 2005 *Curr. Protoc. Micorbiol*. Appendix 3) and viability of may be assessed using colony counts as described, for example, by Murray et al. (In: Manual of Clinical Microbiology, American Society for Microbiology, Washington D.C., Ninth Edition 2007).

A preferred cell culture medium is supplemented with bovine serum, or a modified cell culture medium comprising a serum alternative suitable for cultivation of mammalian cells and comprising sufficient carbon and energy sources to support growth of *H. pylori* in a fermentation process. Preferred cell culture media have regulatory approval for use in production of human therapeutics.

For example, *H. pylori* may be cultured on a defined medium supplemented with bovine serum and fortified with Fe3+. Exemplary medium is an F12 liquid medium supplemented with $NaHCO_3$, fetal bovine serum (FBS) 10% (v/v) and $FeSO_4$ (75 µM).

In a particularly preferred example, medium for cultivation of *H pylori* comprises calcium chloride (e.g., calcium chloride anhydrous), cupric sulfate (e.g., as cupric sulfate.$5H_2O$), ferrous sulfate (e.g., $FeSO_4.7H_2O$), magnesium chloride (e.g., magnesium chloride anhydrous), potassium chloride, sodium chloride, sodium phosphate (e.g., sodium phosphate dibasic [anhydrous]), zinc sulfate.$7H_2O$ (e.g., zinc sulfate.$7H_2O$), L-alanine, L-arginine (e.g., L-arginine.HCl), L-asparagine (e.g., L-asparagine. $H_2O$), L-aspartic acid, L-cysteine (e.g., L-cysteine.HCl or L-cysteine.HCl.$H_2O$), L-glutamic acid, L-glutamine, glycine, L-histidine (e.g., L-histidine. HCl or L-histidine.HCl.$H_2O$), L-isoleucine, L-leucine, L-lysine (e.g., L-lysine. HCl), L-methionine, L-phenylalanine, L-proline, L-serine, L-threonine, L-tryptophan, L-tyrosine (e.g., L-tyrosine 2Na.$2H_2O$), L-valine, D-biotin, choline chloride, folic acid, myo-inositol, niacinamide, D-pantothenic acid (hemicalcium), pyridoxine (e.g., pyridoxine.HCl), riboflavin, thiamine (e.g., thiamine-.HCl), vitamin B-12, D-glucose, hypoxanthine, linoleic acid, phenol red (e.g., phenol red.Na), putrescine dihydrochloride, pyruvic acid (e.g., pyruvic acid.Na) thioctic acid, thymidine and bovine serum.

In one such preferred example, the medium for cultivation of *H. pylori* comprises 0.0333 g/L calcium chloride (anhydrous), 0.0000025 g/L cupric sulfate.$5H_2O$, 0.000834 g/L ferrous sulfate.7 $H_2O$, 0.0576 g/L magnesium chloride [anhydrous], 0.224 g/L potassium chloride, 7.599 g/L sodium chloride, 0.14204 g/L sodium phosphate dibasic (anhydrous), 0.000863 g/L zinc sulfate.$7H_2O$, 0.009 g/L L-alanine, 0.211 g/L L-arginine. HCl, 0.01501 g/L L-asparagine.$H_2O$, 0.0133 g/L L-aspartic acid, 0.035 g/L L-cysteine.HCl.$H_2O$, 0.0147 g/L L-glutamic acid, 0146 g/L L-glutamine, 0.00751 g/L glycine, 0.02096 g/L L-histidine.HCl.$H_2O$, 0.00394 g/L L-isoleucine, 0.0131 g/L L-leucine, 0.0365 g/L L-lysine.HCl, 0.00448 g/L L-methionine, 0.00496 g/L L-phenylalanine, 0.0345 g/L L-proline, 0.0105 g/L L-serine, 0.0119 g/L L-threonine, 0.00204 g/L L-tryptophan, 0.00778 g/L L-tyrosine 2Na.$2H_2O$, 0.0117 g/L L-valine, 0.0000073 g/L D-biotin, 0.01396 g/L choline chloride, 0.00132 g/L folic acid, 0.018 g/L myo-inositol, 0.000037 g/L niacinamide, 0.00048 g/L D-pantothenic acid (hemicalcium), 0.000062 g/L pyridoxine.HCl, 0.000038 g/L riboflavin, 0.00034 g/L thiamine.HCl, 0.00136 g/L vitamin B-12, 1.802 g/L D-glucose, 0.00408 hypoxanthine, 0.000084 g/L linoleic acid, 0.0013 g/L phenol red.Na, 0.000161 g/L putrescine dihydrochloride, 0.11 g/L pyruvic acid.Na, 0.00021 g/L thioctic acid, 0.00073 g/L thymidine and bovine serum 100 ml.

In media for culturing *H. pylori*, FBS may be substituted for bovine serum albumin with or without lipid supplementation. Alternatively, plasma may be substituted for FBS, because plasma comprises components of the coagulation cascade that may influence the physiology of the cells e.g., their lipid profile and/or protein profile and/or LPS profile.

Other semi-synthetic media, based on plant proteins or other cell culture media, may also be employed.

*H. pylori* may be cultivated in a liquid, semisolid or solid form. Examples of liquid media include *Brucella* Broth, Columbia Broth, brain heart infusion broth, Wilkins-Chalgren broth, Ham's F-10 nutrient media, Ham's F-12 nutrient media, Mueller-Hinton broth, Skirrow *Campylobacter* media, Belo Horizonte media, Dent's CP media and *H. pylori* special peptone broth as described for example by Stevenson et al. 2000 *Lett. Appl. Microbiol.* 30: 192-196. Semisolid and solid media may be prepared from any of the liquid media described in any example hereof, by the addition of a solidifying agent such as, for example, agar. Alternatively, a specialised semisolid and/or solid medium may be used, such as, for example, Chocolate agar, Tryptic Soy Agar, Glupszynski's Brussels *campylobacter* charcoal agar and Johnson-Murano agar.

The medium may be supplemented with blood or a blood component. As used herein term "blood" shall be taken to mean whole blood and "blood component" refers to serum and/or plasma and/or plasma fractions and/or red blood cells and/or white blood cells and/or platelets and/or protein fractions. Preferably, the blood or blood component is defibrinated. In one example, the blood component is from a mammal.

Suitable mammals include, for example, goats, sheep, bison, cows, pigs, rabbits, buffalos, horses, rats, mouses, or humans. In a preferred example, the blood component may comprise serum. In one example, the serum may be fetal calf serum or newborn calf serum or bovine serum. Media may be supplement with blood or a blood product at final concentration in the media of 1% (vol/vol) or at least 2% (vol/vol) or at least 3% (vol/vol) or at least 4% (vol/vol) or at least 5% (vol/vol) or at least 6% (vol/vol) or at least 7% (vol/vol) or at least 8% (vol/vol) or at least 9% (vol/vol) or at least 10% (vol/vol) or at least 15% (vol/vol) or at least 20% (vol/vol) or at least 25% (vol/vol). In another example, the blood may comprise heat inactivated blood. In another example, the medium may comprise a mixture of heat inactivated and non-heat inactivated blood. Methods of heat inactivating blood are known in the art and are described, for example in Ayache et al. 2006 *J. Transl. Med.* 4:40.

Alternatively, *H. pylori* may be cultivated in blood-free medium, such as an egg yolk emulsion medium as described, for example, by Westblom et al. 1991 *J. Clin. Microbiol.* 29:819-821, or a cyanobacterial extract based medium as described for example, by Vega et al. 2003 *J. Clin. Micrbiol.* 41: 5384-5388.

In another example, the medium may be supplemented with chemical supplements, such as for example, adenine and/or cysteine hydrochloride and/or cyclodextrin and/or ferric nitrate and/or ferrous sulfate and/or peptone and/or IsoVitaleX and/or Vitox and/or starch and/or sodium bicarbonate and/or sodium pyruvate and/or mucin and/or Vitamin B12 and/or L-glutamine and/or guanine and/or p-aminobenzoic acid and/or L-cystine and/or yeast extract.

In yet another example, the medium may be supplemented with antibiotics capable of inhibiting growth of non-*H. pylori* microorganisms. Suitable antibiotics may include, vancomycin and/or trimethoprim and/or cefsulodin and/or amphotericin B and/or polymyxine.

Preferably, *H. pylori* is cultured in medium without antibiotics.

Environmental Conditions

As will be known to the skilled artisan, *H. pylori* may be cultivated in a micro-aerobic atmosphere such as, for example, in a $CO_2$ incubator or in an anaerobic chamber with a micro-aerobic atmosphere or in a gas jar with gas-generation kits as described.

Suitable micro-aerobic atmospheres are described, for example, by Mobley et al. (In *H. pylori: Physiology and Genetics*. American Society for Microbiology, Washington D.C., 2001). In one example, *H. pylori* may be cultivated in an atmosphere comprising about 1% to about 10% oxygen, about 5% to about 10% carbon dioxide, and about 0% to about 10% hydrogen.

Temperature conditions used to cultivate *H. pylori* are known in the art. For example, *H. pylori* may be cultivated at a temperature of between about 25° C. to about 45° C. Preferably, *H. pylori* may be cultivated at a temperature of between about 30° C. to about 40° C. More preferably, *H. pylori* may be cultivated at a temperature of about 37° C.

In one example, *H. pylori* may be stressed during cultivation. As used herein, the term "stressed" shall be taken to mean a change in an environmental condition. For example, *H. pylori* may be exposed to environmental stresses such as, for example, oxidative stress, pH stress, osmotic stress, carbon starvation, phosphate starvation, nitrogen starvation, amino acid starvation, oxygen stress e.g., by growing *H. pylori* under anaerobic conditions, heat or cold shock or mutagenic stress. Preferably, exposure of *H. pylori* to environmental stress(es) during cultivation results in one or more metabolic changes in *H. pylori* such as enhanced lipopolysaccharide synthesis and surface presentation thereof and/or degradation of *H. pylori* cellular proteins.

Cell Culture Containers

*H. pylori* may be cultivated in using standard cell culture containers known to the skilled artisan, such as, for example multi-well plates, petri-dish, roller bottles, T flasks, D flasks, culture chambers, hyperflask vessels, spinner flasks and Erlenmeyer flasks.

Preferred cell culture conditions are optimized for cell culture medium, shear sensitivity, oxygen and other gas requirements, and pH control, to provide for optimum growth of *H. pylori* in large-scale culture e.g., a high optical density of cell culture in a short time frame.

Preferably, *H. pylori* may be cultivated in a bioreactor. As used herein the term "bioreactor" shall be taken to mean an apparatus for the cultivation of prokaryotic and/or eukaryotic cell cultures under controlled conditions. The bioreactor may be operated in a batch or fed batch or an extended batch or a repetitive batch or a draw/fill or a rotating-wall or a spinning flask or a semi-continuous or perfusion or a continuous mode.

In one example, the bioreactor may agitate the cell culture for purposes of aeration using methods such as, for example, rocking, stirring, or channeling fluid or gas through the culture. Examples of such bioreactors include, for example, stirred tank fermentors or bioreactors agitated by rotating mixing devices, chemostats, bioreactors agitated by shaking devices, airlift fermentors/bioreactors, fluidized bed bioreactors, bioreactors employing wave induced agitation, centrifugal bioreactors or roller bottles.

In another example, the bioreactor may comprise means for quantification of biomass, such as, for example, by measuring the optical density of the culture medium. Suitable means for quantification of biomass include, for example, an optical sensor or a waveguide sensor or a Raman spectroscopy.

In yet another example, the bioreactor may include means for monitoring and/or measuring and/or adjusting one or more bioprocess parameters. As used herein, the term "bioprocess parameter" shall be taken to mean a chemical or physical property that may alter the growth rate of *H. pylori*. Suitable bioprocess parameters include, for example, temperature, pH, dissolved oxygen, carbon dioxide concentration, carbon source concentration, bile salt concentration, light, glucose concentration, pressure, concentration of an ionic species, concentration of a cellular metabolite, molarity, osmolality, glucose concentration, serum concentration and degree of agitation.

As will be apparent to the skilled artisan, a number of methods may be used to determine the growth rate of *H. pylori*.

Preferably, the bioreactor is a microreactor. The term "microreactor" as used herein refers to a bioreactor having a volume of less than 1000 mL or less than 900 mL or less than 800 mL or less than 700 mL or less than 600 mL or less than 500 mL or less than 400 mL or less than 300 mL or less than 200 mL or less than 100 mL or less than 90 mL or less than 80 mL or less than 70 mL or less than 60 mL or less than 50 mL or less than 40 mL or less than 30 mL or less than 20 mL or less than 15 mL or less than 10 mL or less than 9 mL or less than 8 mL or less than 7 mL or less than 6 mL or less than 5 mL or less than 4 mL or less than 3 mL or less than 2 mL or less than 1 mL. Commercially available microreactors include, for example, the micro-Matrix (Applikon Biotechnology), the micro-flask (Applikon Biotechnology) and the advanced micro-scale bioreactor (Tap Biosystems).

Alternatively, the bioreactor is a large scale bioreactor. As used herein the term "large scale bioreactor" refers to a bioreactor used to produce a product for sale or for production of an intermediate of a product for sale. Preferably, a large scale bioreactor has an internal capacity of at least 1 L at least 2 L at least 3 L at least 4 L at least 5 L at least 6 L at least 7 L at least 8 L at least 9 L at least 10 L at least 20 L at least 50 L at least 100 L at least 200 L at least 300 L at least 400 L at least 500 L at least 600 L at least 700 L at least 800 L at least 900 L at least 1000 L in particular at least 2000 L at least 3000 L or at least 4000 L.

In a particularly preferred example, *H. pylori* is cultured from a frozen or unfrozen glycerol stock or other liquid stock or plate stock, employing *H. pylori* e.g., in a stock volume of about 3 mL that is then seeded into and cultured in a multichannel miniature bioreactor system or scalable stirred tank bioreactor e.g., a 2 L bench-top stirred tank bioreactor. A seed train may be employed, wherein an inoculum is prepared for a pilot-scale bioreactor. For example, a 400 L pilot-scale batch of H. pylori may be produced from one or two or three or four or five seed stages wherein each seed stage provides a 10-fold amplification of bacterial culture density as determined by OD at about 600 nm. In a similar scale-up process, an inoculum from a pilot-scale bioreactor is employed to inoculate a production-scale bioreactor. For example, batches of 2 L to 20 L of culture from a pilot-scale bioreactor process are combined until an appropriate volume is obtained for inoculation of a production-scale bioreactor. Incubation times for each stage vary in a range from about 16 hours to about 120 hours, including 16 hours to about 96 hours.

In another example, a seed culture is used to amplify cells and process volume to generate an inoculum for a pilot-scale bioreactor, which is then employed to inoculate medium in a production-scale bioreactor. For example, H. pylori cells (0.5 mL) stored frozen at −80° C. are revived by thawing at room temperature and 0.4 mL is transferred to 20 to 100 mL of medium, and the culture is incubated in a microaerobic environment at 37° C. for 16 to 96 hours until the optical density (measured at 600 nm) is in a range from about 0.4 to about 20. This seed culture is then used to inoculate a larger culture having a volume from about 200 mL to about 2000 mL which is then incubated under the same conditions to achieve the same cellular concentration as before. The larger culture is then used to inoculate a small bioreactor having an operating volume of 2 L (e.g., Biostat B, Sartorius-Stedim, Germany) or 10 L (e.g., Biostat C10, Sartorius-Stedim, Germany) or 16 L (e.g., New Brunswick Bioflo 510, Eppendorf, USA) or 50 L (e.g., Biostat D50, Sartorius-Stedim, Germany). The bioreactor is operated at 37° C. with pH, dissolved oxygen, and foam control. The pH is controlled at a set point in the range from pH6 to pH 8 such as by automatic addition of 10% (v/v) phosphoric acid or 10% (v/v) ammonia solution. Preferably, the bioreactor is sparged with a gas mixture containing nitrogen, carbon dioxide and a small proportion of oxygen (or compressed air) and a dissolved oxygen saturation is controlled e.g., in a range from 0.5% to 10% saturation, such as by varying stirrer speed and/or gas flow rate and/or vessel back pressure. Foam may be controlled by automatic addition of chemical antifoam, e.g., polypropylene glycol, added as required.

In an example of production-scale bioreactor process, a bioreactor having a volume from about 400 L to about 10,000 L is operated in a configuration that enables high yield of H. pylori cells. The system may be configured with an automated sterilization process and a series of re-sterilizable sample(s) and addition valves, to enable sampling and addition of reagent and product during fermentation. At inoculation, the inoculum is transferred aseptically to the production bioreactor. The bioreactor is operated at 37° C. with pH, dissolved oxygen and foam control, essentially as during the pilot-scale production process.

Fed-batch or "semi-batch" culture is particularly preferred for large-scale production of H. pylori. In fed-batch culture, one or more nutrients are fed to the bioreactor during cultivation and the cellular product remains in the bioreactor until the end of the run. In some cases, all the nutrients are fed into the bioreactor. Fed-batch culture permits better control of the nutrient concentrations in the culture liquid. Fed-batch H. pylori cultures are generally monitored for one or more of dissolved oxygen concentration, feed composition to increase cell number, feed rate to increase cell number, gas requirement required to increase cell number, and nutrient composition of medium required to increase cell number. This is because of the high nutrient demand of H. pylori. Optical density is monitored for comparative analysis of the media formulations and cell growth, such that a high optical density of cells is obtained in the shortest time frame. For example, a cell concentration above levels typically observed in batch culture may be obtained, such as greater than 20 optical density units at 600 nm and/or up to about 40 optical density units at 600 nm.

3. Inactivating and Killing H. pylori

H. pylori may be inactivated and/or killed by chemical means and/or physical means and/or genetic means. As used herein, the term "chemical means" refers to a method of inactivating and/or killing H. pylori by exposing H. pylori to a chemical agent. As used herein, the term "physical means" refers to a method of inactivating and/or killing H. pylori by exposing H. pylori to one or more physical treatments not involving the use of a chemical. As used herein, the term "genetic means" refers to a method of inactivating and/or killing H. pylori by modifying the genome of H. pylori.

Suitable chemical means for inactivating and/or killing H. pylori include the addition of one or more chemical agents such as formaldehyde and/or β-propiolactone and/or ethyleneimine and/or binary ethyleneimine and/or thimerosal and/or acid and/or alkali and/or one or more bactericidal agents and/or one or more reducing agents and/or a bile salt. Derivatives of these chemical agents known in the art may also be employed.

In one preferred example, H. pylori is inactivated and/or killed by exposure to formaldehyde at a concentration from about 0.01% to about 1% (w/w) or from about 0.01% to about 0.1% (w/w) or between about 0.025% and about 0.1% (w/w).

Alternatively, or in addition, H. pylori is inactivated and/or killed by exposure to polyethyleneimine functionalized zinc oxide nanoparticles as described, for example, by Chakraborti et al. 2012 Langmuir, 28:11142-11152.

Alternatively, or in addition, killed H. pylori as described according to any example hereof is prepared by exposing live and/or inactivated H. pylori cells or strains to one or more bactericidal agent(s). For example, live and/or inactivated H. pylori can be subjected to treatment with one or more antibiotics selected from rifampin, amoxicillin, clarithromycin, rifamycin, rifaximin, the rifamycin derivative 3'-hydroxy-5'-(4-isobutyl-1-piperazinyl)benzoxazinorifamycin syn. KRM-1648 and/or the rifamycin derivative 3'-hydroxy-5'-(4-propyl-1-piperazinyl)benzoxazinorifamycin syn. KRM-1657.

Alternatively, or in addition, inactivated H. pylori as described according to any example hereof is prepared by exposing live H. pylori cells or strains to one or more acid(s) or to a low pH environment such as pH 3.0 or lower and/or to one or more base(s) or to high pH environment such as pH 9.0 or higher.

Alternatively, or in addition, inactivated and/or killed H. pylori as described according to any example hereof is prepared by exposing live H. pylori cells or strains to one or more reducing agent(s) such as sodium bisulfite and/or one or more oxidative agents such as hydrogen peroxide.

Alternatively, or in addition, inactivated and/or killed H. pylori as described according to any example hereof is prepared by exposing live H. pylori cells or strains to bile salts.

Suitable physical means for inactivating and/or killing H, pylori include exposure to visible light and/or ultraviolet light such as UV-C light and/or low-power laser photosensitizer and/or heat (e.g., dry heat or wet heat such as in steam) and/or elevated pressure and/or temperature shift and/or freeze-thaw and/or freeze-drying (lyophilization) and/or sonication.

Alternatively, or in addition *H. pylori* is inactivated and/or killed by exposure to visible light at wavelengths ranging from about 375 nm to about 500 nm or in a range from about 400 nm to about 420 nm.

Alternatively, or in addition, *H pylori* is inactivated and/or killed by exposure to ultraviolet light, e.g., Hayes el al. 2006, *Appl. Environ. Microbiol.* 72: 3763-3765.

For example, inactivated *H. pylori* as described according to any example hereof is prepared by exposing live *H. pylori* cells or strains to irradiation such as ultraviolet irradiation and/or by exposure to visible light such as wavelengths ranging from about 375 nm to about 500 nm or in a range from about 400 nm to about 420 nm e.g., 405 nm violet light. In one example, inactivated *H pylori* as described according to any example hereof is prepared by a process comprising exposing live *H pylori* cells or strains to ultraviolet C (UVC) irradiation such as wavelength in a range from about 100 nm to about 280 nm such as about 257.3 nm and/or to ultraviolet B (UVB) irradiation such as wavelength in a range from about 280 nm to about 315 nm and/or to ultraviolet A (UVA) irradiation such as wavelength in a range from about 315 nm to about 400 nm. Preferably, the live *H. pylori* is exposed to UVC light in a range from about 100 nm to about 280 nm such as about 257.3 nm and/or the live *H. pylori* is exposed to about 405 nm violet light to thereby inactivate *H. pylori*.

Alternatively, killed *H. pylori* as described according to any example hereof is prepared by a process comprising exposing live or inactivated *H. pylori* cells or strains to ultraviolet C (UV-C) irradiation such as wavelength in a range from about 100 nm to about 280 nm e.g., about 257.3 nm and/or to ultraviolet B (UV-B) irradiation such as wavelength in a range from about 280 nm to about 315 nm and/or to ultraviolet A (UV-A) irradiation such as wavelength in a range from about 315 nm to about 400 nm. Preferably, the live or inactivated *H. pylori* is exposed to UV-C light in a range from about 100 nm to about 280 nm such as about 257.3 nm. Alternatively, the live or inactivated is exposed to about 405 nm violet light to thereby kill *H. pylori*.

Alternatively, or in addition *H. pylori* is inactivated and/or killed by exposure to gamma irradiation.

Alternatively, or in addition, *H. pylori* is inactivated and/or killed by exposing live or inactivated *H. pylori* to low-power laser light in the presence of a photosensitiser as described, for example, by MILLSON et al. 1996 *J. Med. Microbiology*, 44:245-252. Alternatively, or in addition, *H. pylori* is inactivated and/or killed by heat treatment of cells.

For example, *H. pylori* may be inactivated by heat treatment wherein live *H. pylori* cells are exposed to heat treatment such as at temperatures in the range between about 40° C. to about 70° C. or more. Preferred heat treatment in this context may comprise exposure of live *H. pylori* cells to a temperature of about 60° C. or more for at least about 60 seconds, preferably at a temperature of about 60° C. or about 70° C. or about 80° C. or about 90° C. or about 100° C. or about 110° C. or about 120° C. or about 130° C. or about 140° C. or about 150° C., said temperature exposure being for a period of at least 3 minutes or at least 4 minutes or at least 5 minutes or at least 6 minutes or at least 7 minutes or at least 8 minutes or at least 9 minutes or at least 10 minutes or at least 20 minutes or at least 30 minutes or at least 40 minutes or at least 50 minutes or at least 1 hour or at least 2 hours or at least 3 hours or at least 4 hours or at least 5 hours or at least 6 hours or at least 7 hours or at least 8 hours or at least 9 hours or at least 10 hours or at least 11 hours or at least 12 hours or at least 13 hours or at least 14 hours or at least 15 hours or at least 16 hours or at least 17 hours or at least 18 hours or at least 19 hours or at least 20 hours or at least 21 hours or at least 22 hours or at least 23 hours or at least 1 day or at least 2 days or at least 3 days or at least 5 days or at least 5 days or at least 6 days or at least 7 days.

Alternatively, killed *H. pylori* as described according to any example hereof is prepared by exposing live and/or inactivated *H. pylori* cells or strains to heat treatment such as by exposure to temperature of about 60° C. or more for at least about 60 seconds, preferably at a temperature of about 60° C. or about 70° C. or about 80° C. or about 90° C. or about 100° C. or about 110° C. or about 120° C. or about 130° C. or about 140° C. or about 150° C., said temperature exposure being for a period of at least 2 minutes or at least 3 minutes or at least 4 minutes or at least 5 minutes or at least 6 minutes or at least 7 minutes or at least 8 minutes or at least 9 minutes or at least 10 minutes or at least 20 minutes or at least 30 minutes or at least 40 minutes or at least 50 minutes or at least 1 hour or at least 2 hours or at least 3 hours or at least 4 hours or at least 5 hours or at least 6 hours or at least 7 hours or at least 8 hours or at least 9 hours or at least 10 hours or at least 11 hours or at least 12 hours or at least 13 hours or at least 14 hours or at least 15 hours or at least 16 hours or at least 17 hours or at least 18 hours or at least 19 hours or at least 20 hours or at least 21 hours or at least 22 hours or at least 23 hours or at least 1 day or at least 2 days or at least 3 days or at least 5 days or at least 5 days or at least 6 days or at least 7 days.

In one preferred example, live and/or inactivated *H. pylori* is killed by exposure to a single such elevated temperature or by exposure to at least two different elevated temperatures such as by exposure to a first temperature of about 70° C. followed exposure to a second temperature of about 90° C. or about 95° C. In one such preferred example, the live and/or inactivated *H. pylori* is killed by exposure to temperature of about 70° C. for about 10 minutes followed by exposure to temperature of about 90° C. or about 94° C. or about 95° C. for about 5 minutes.

Alternatively, or in addition, killed *H. pylori* as described according to any example hereof is prepared by exposing live and/or inactivated *H. pylori* cells or strains to elevated temperatures in the presence of steam and elevated pressure, such as by autoclaving live and/or inactivated *H. pylori* cells or strains. For example, live and/or inactivated *H. pylori* is killed by autoclaving the bacterial cells or strains for about 15 minutes at about 121° C. and about 15 psi, or for about 3 minutes at about at 132° C. and about 30 psi.

In one preferred example, *H. pylori* is inactivated and/or killed by temperature shift such as exposure to a single such elevated temperature or by exposure to at least two different elevated temperatures such as by exposure to a first temperature of about 70° C., followed exposure to a second temperature of about 90° C. or about 94° C. or about 95° C.

Alternatively, or in addition, *H. pylori* is inactivated and/or killed exposure of cells to one or more freeze-thaw cycles e.g., by exposure to 2 or 3 or 4 or 5 or 6 or 7 or 8 or 9 or 10 freeze-thaw cycles. Exemplary freeze-thaw cycles comprise freezing *H. pylori* in a dry ice/ethanol bath and then thawing the material at 37° C.

Alternatively, or in addition, *H. pylori* is inactivated and/or killed by freeze-drying cells.

Alternatively, or in addition, *H. pylori* is inactivated and/or killed by sonicating the cells. For example, killed *H.*

*pylori* as described according to any example hereof is prepared by sonication e.g., at ultrasonic frequencies such as about 20 kHz or more of live and/or inactivated *H. pylori*.

Preferably, the inactivated and/or killed *H. pylori* as described according to any example hereof is prepared by first by exposing live *H. pylori* cells or strains to irradiation such as gamma irradiation and/or ultraviolet irradiation such as UV-C light and/or by exposure to visible light such as wavelengths ranging from about 375 nm to about 500 nm or in a range from about 400 nm to about 420 nm, to thereby inactivate *H. pylori* and then exposing the inactivated *H. pylori* cells or strains to heat treatment as described according to any example hereof to thereby kill the inactivated *H. pylori* or render the inactivated *H. pylori* irreversibly metabolically inactive.

For example, the inactivated *H. pylori* is then exposed to temperature of about 60° C. or more for at least about 60 seconds, preferably at a temperature of about 60° C. or about 70° C. or about 80° C. or about 90° C. or about 100° C. or about 110° C. or about 120° C. or about 130° C. or about 140° C. or about 150° C., said temperature exposure being for a period of at least 2 minutes or at least 3 minutes or at least 4 minutes or at least 5 minutes or at least 6 minutes or at least 7 minutes or at least 8 minutes or at least 9 minutes or at least 10 minutes or at least 20 minutes or at least 30 minutes or at least 40 minutes or at least 50 minutes or at least 1 hour or at least 2 hours or at least 3 hours or at least 4 hours or at least 5 hours or at least 6 hours or at least 7 hours or at least 8 hours or at least 9 hours or at least 10 hours or at least 11 hours or at least 12 hours or at least 13 hours or at least 14 hours or at least 15 hours or at least 16 hours or at least 17 hours or at least 18 hours or at least 19 hours or at least 20 hours or at least 21 hours or at least 22 hours or at least 23 hours or at least 1 day or at least 2 days or at least 3 days or at least 5 days or at least 5 days or at least 6 days or at least 7 days. In one such example, the inactivated *H. pylori* is exposed to a single such elevated temperature or to at least two different elevated temperatures such as by exposure to a first temperature of about 70° C. e.g., for about 10 minutes, followed by exposure to a second temperature of about 90° C. or about 95° C. e.g., for about 5 minutes.

In one preferred example, the killed *H. pylori* as described according to any example hereof is prepared by first by exposing live *H. pylori* cells or strains to ultraviolet irradiation such as UVC light e.g., at about as 257.3 nm to thereby inactivate *H. pylori* and then exposing the inactivated *H. pylori* cells or strains to heat treatment as described according to any example hereof to thereby kill the inactivated *H. pylori* or render the inactivated *H. pylori* irreversibly metabolically inactive.

Accordingly, in one preferred example, the composition according to any example hereof comprises *H. pylori* that has been subjected to a process for inactivating *H. pylori* by irradiation and a process for the killing the inactivated *H. pylori* by heat treatment.

Alternatively, or in addition, *H. pylori* as described according to any example hereof is inactivated and/or killed by exposing live or inactivated *H. pylori* to anaerobic conditions e.g., by changing the atmosphere in which *H. pylori* is cultured from microaerobic to anaerobic environment for example to mimic the in vivo atmospheric conditions during the washout of *H. pylori* from the stomach to the lower gut (e.g., small and/or large intestine). For example, live (such as freshly grown) *H. pylori* is inactivated by exposing (e.g., by growing or incubating) the bacterial cells to anaerobic conditions for about 1 day to about 5 days or more, including for at least about 24 hours, or for at least about 48 hours or at least about 73 hours or at least about 96 hours or at least about 120 hours. In one such example, the live *H. pylori* cells are inactivated by exposing the cells to anaerobic conditions and by heat treatment of the cells.

In another example, live or inactivated *H. pylori* as described according to any example hereof is killed by exposing (e.g., by incubation) the live or inactivated bacterial cells to anaerobic conditions for about 1 day to about 5 days or more, including for at least about 24 hours, or for at least about 48 hours or at least about 73 hours or at least about 96 hours or at least about 120 hours.

In one preferred example, the composition according to any example hereof comprises *H. pylori* that has been subjected to a process for inactivating *H. pylori* by exposing (e.g., by growing or incubating) the bacterial cells to anaerobic conditions for about 1 day to about 5 days or more, including for at least about 24 hours, or for at least about 48 hours or at least about 73 hours or at least about 96 hours or at least about 120 hours, and a process for the killing the inactivated *H. pylori* by heat treatment of the cells.

Suitable genetic means for producing inactivated *H. pylori* as described according to any example hereof comprises mutagenesis of live *H. pylori* cells or strains to modify one or more genes the expression of which is/are required for efficient colonization and/or maintenance of *H pylori* in the stomach and intestinal mucosa of human subject. For example, such genes may be deleted by recombination or modified by insertion of a transposon or other genetic element, or they may be inactivated by chemical mutagenesis. Such means are described in the art.

Inactivation and/or killing may be performed on *H. pylori* cells that are in a liquid, semisolid or solid form. In one example, *H. pylori* cultivated in a liquid may be inactivated and/or killed during a logarithmic phase of growth i.e., wherein cell numbers are increasing exponentially in culture or stationary phase of growth i.e., wherein viable cells in culture are post-logarithmic and not increasing in number.

In a particularly preferred example, a pilot-scale culture or other large-scale culture e.g., greater than 2 L or greater than 5 L or greater than 10 L or about 100 L to about 400 L volume including 100 L or 150 L or 200 L or 250 L or 300 L or 350 L or 400 L, or larger volume culture, is treated in a steam-in-place bioreactor or sterilisable-in-place bioreactor e.g., having the same operating system as a pilot-scale reactor described herein. In such bioreactors, the inactivation and/or killing process utilizes high temperature and high pressure to generate steam which is applied to the cells once they have achieved a desired cell density, to thereby inactivate and/or kill the cells In another example, a culture in a fed-batch process is subjected to ultraviolet light e.g., UV-C irradiation, at an irradiance of greater than 100 Joules per OD unit at 600 nm, and the cells are then heat-treated at a temperature in a range from 60° C. to about 120° C. including 121° C. for a time in a range from about 15 minutes to about 6 hours.

The present invention also provides a master cell bank comprising the treated *H. pylori* of the present invention prepared as described herein. For example, a master cell bank may comprise aliquots of the treated *H. pylori* cells e.g., 100 or 200 or 300 or 400 or 500 vials comprising the cellular product. Preferably, a master cell bank is stored frozen e.g., at −80° C.

4. Harvesting Treated *H. pylori* Cells

Methods for harvesting microorganisms are well known in the art and are described, for example, by Ausubel et al. (In: Current Protocols in Molecular Biology. Wiley Inter-science, ISBN 047 150338, 1987) or Sambrook et al. (In: Molecular Cloning: Molecular Cloning: A Laboratory Manual, Cold Spring Harbor Laboratories, New York, Third Edition 2001). As used herein, the term "harvesting" refers to a collection of *H. pylori* from medium upon, or in which, a population of *H pylori* has been cultivated. Suitable methods include, for example, centrifugation e.g. ultracentrifugation, or by filtration, e.g. ultrafiltration or microfiltration or deep filtration.

*H pylori* cells are generally harvested after inactivation and/or killing.

In a preferred example, treated cells are recovered from culture e.g., a bioreactor, by employing continuous centrifugation such as at a centrifugal force in a range from about 5,000×g to about 20,000×g. Preferably, the harvested cells are washed using a formulation buffer e.g., a phosphate-buffered saline or other pharmaceutically-acceptable excipient or diluent. The wash solution may be supplemented with dextran or an encapsulation formulations.

The cellular product is then packaged ready for storage or use. Preferably, the cells are lyophilized or spray-dried to generate a solid product suitable for long term storage.

Packs comprise one or more specifications of cellular product e.g., cell concentration, buffer composition, liquid formulation, dry formulation, pack size, etc.

5. Determining or Identifying Inactivated and/or Killed *H. pylori*

A method to measure utility of *H. pylori* or cell thereof in the compositions and/or methods as described in any example hereof includes any method that measures the ability of *H. pylori* or cell thereof to replicate and/or colonize a gastric mucosa of a mammal and/or any method that measures the ability of *H. pylori* or cell thereof to adhere to the gastric mucosa or epithelial cells thereof and/or any method that measure viability and/or metabolic activity of *H. pylori* e.g., following stress and/or inactivation and/or killing treatment of H, *pylori* as described according to any example hereof.

In one example, the ability of a *H. pylori* or cell thereof to replicate and colonize the gastric mucosa in a mammal is determined by quantification of viable bacteria such as by colony count. See e.g., Drumm and Sheman 1991, *J. Med. Microbiol* 35:197-202.

For example, 0.5 ml of a sample measuring cell equivalent of optical density of about 0.2 to about 5.0 or more at 660 nm stored *H. pylori* bacteria which has been cultured, and subjected to stress and/or inactivation and/or killing treatment e.g., as described according to any example hereof, is resuspended in a 250 ml Erlenmeyer flask containing 11 ml of fresh medium of *Brucella* Broth (e.g., Gibco Laboratories, Madison, Wis., USA) supplemented with 10% fetal bovine serum (e.g., Boknek Laboratories, Ontario, Canada), or other media suitable for growth of *H. pylori* e.g., as described according to any example hereof. If required, the culture medium is supplemented with trimethoprim (e.g., Sigma Chemicals, St. Louis, Mo., USA) 5 mg/L and/or vancomycin (e.g., Sigma) 10 mg/L. The flask is closed with a loosely fitted screw cap and placed inside an incubation jar which is then evacuated and flushed through with a gas mixture containing $CO_2$ 10%, $O_2$ 5%, $N_2$ 85%, and incubated at 37° C. on a rotary shaker and incubated at 37° C. with shaking at 100 rpm. After about 24 hours, approximately 1 ml of bacterial culture is transferred to fresh medium of *Brucella* Broth and re-cultured. Absence of viable and replicating *H. pylori* is confirmed by subculture of broth on supplemented *Brucella* agar plates and inspection of bacterial morphology by phase contract microscopy. See e.g., Drumm and Sherman, 1989, *J. Clin Microbiol*, 27:1655-1656.

Alternatively, or in addition, quantification of viable and replicating *H. pylori* bacteria is performed in the broth cultures by serial dilution and sequential measurements of optical density of cultures at 600 nm and/or by colony counts e.g., after incubation for 6, 12, 18, 24, 30 and 36 hours. For example, if present, cell counts of viable and replicating *H. pylori* bacteria are determined by inoculating serial dilutions of cultures in triplicates onto *Brucella* agar and incubating plates for 5 days at 37° C. in microaerobic conditions. Viable and replicating *H. pylori* produce smooth, translucent colonies on *Brucella* agar. To improve the accuracy of viable counts (cfu), 4 mg/L tetrazolium salts are added to the *Brucella* agar prior to inoculation of the agar with the bacterial cultures. After incubation for 5 days at 37° C. in microaerobic conditions, viable and replicating *H. pylori* cells produce red colonies on this medium. Absence of *H. pylori* colonies as described herein confirms that *H. pylori* is inactivated and/or killed and is incapable of replicating and colonising the gastric mucosa.

In another example, inactivated and/or killed *H. pylori* may be confirmed by any assay measuring metabolic activity of *H. pylori* such as, for example, urease production and/or ATP consumption.

In one preferred example, Rapid Urease Test, also known as *Campylobacter*-like organism (CLO) test, is used to detect presence of *H. pylori* which is partially or fully metabolically active based on the ability of *H. pylori* to secrete a urease enzyme which catalyzes the conversion of urea to ammonia and $CO_2$. According to this example, aliquots of about 1 µl to about 100 µl, of samples measuring cell equivalent of optical density of about 0.2 to about 5.0 or more at 660 nm of stored *H. pylori* bacteria cultured, and subjected to stress and/or inactivation and/or killing treatment e.g., as described according to any example hereof, or aliquots of about 1 µl to 100 µl of bacterial cells cultured in any suitable medium e.g., *Brucella* Broth medium as described above, are added to sterile Eppendorf tubes containing freshly prepared urease indicator reagent to a total volume of 200 µl. For example, a urease indicator reagent containing about 2% (w/v) to about 5% (w/v) urea, and at least one pH indicator such as phenol red, bromothymol blue, bromocresol purple, and methyl red at a concentration of about 0.1% (w/v) or about 0.05% (w/v) in 0.01 M phosphate-buffered saline (PBS), may be used. If required, the pH of each urease indicator reagent formulation may be adjusted to the lower end of the known pH range for each indicator with the use of 0.1 N or 1.0 N HCl; For example, the indicator phenol red has a pH range of 6.6 to 8.0 and a urease indicator reagent formulation comprising phenol red may be adjusted to pH 6.6; the indicator bromothymol blue has a pH range of 6.0 to 7.6 and a urease indicator reagent formulation comprising bromothymol blue may be adjusted to pH 6.0; the indicator the indicator bromocresol purple has a pH range of 5.2 to 6.8 and a urease indicator reagent formulation comprising bromocresol purple may be adjusted to pH 5.2; the indicator the indicator Methyl red has a pH range of 4.8 to 6.2 and a urease indicator reagent formulation comprising bromocresol purple may be adjusted to pH 4.8. Alternatively, the urease indicator reagent is prepared as described by Nedrud J G, Blanchard T G. Helicobacter animal models. In: Coligan J E, Bierer B, Margulies D H, Shevach E M, Strober W, Coico R, editors. *Current Protocols in Immunology*. Philadelphia: John Wiley and Sons; 2000. p. 19.8.1-26. Alternatively, the urease indicator reagent may be obtained commercially e.g., from ASAN pharm. Co., Seoul, Korea. The tubes are then vortexes and incubated at room temperature. After 4 hours the tubes are centrifuged at RCF 6000 for 5 minutes and about 100 µl of the supernatant is transferred to a 96-well plate to be read spectrophotometrically at 550 nm. If required, Gastric mucosal tissue homogenates from mice uninfected with *H. pylori* e.g., prepared as described below may serve as negative control for the urease assay. Also, if required, a positive control containing known concentrations of cultured *H. pylori* such as wild type *H. pylori* capable of replicating and colonizing the mucosa may be used. Samples of *H. pylori* showing less than 5% urease activity as determined by the Rapid Urease Test indicate *H. pylori* which is inactivated and/or killed.

As will be apparent to the skilled artisan, a number of urease tests are commercially available, such as, for example, CLOtest (Kimberly-Clark), Hpfast (Sigma) and Pyloritek (Serim).

In another example, inactivation and/or killing of *H. pylori* is confirmed by performing an oxidase test. As used herein, the term "oxidase test" shall refer to an assay used to detects the presence of a cytochrome c oxidase using a redox indicator such as, for example, N,N,N,N-tetramethyl-p-phenylenediamine (TMPD) or N,N-dimethyl-p-phenylenediamine (DMPD). Suitable oxidase tests are described for example by Tsukita et al. 1999 *J. Biochem.* 1235:194-201 or Murray et al. (In: Manual of Clinical Microbiology, American Society for Microbiology, Washington D.C., Ninth Edition 2007).

In another example, inactivation and/or killing of *H. pylori* is confirmed by performing a catalase test. The term "catalase test" shall be taken to encompass any assay that determines the ability of *H. pylori* to liberate oxygen gas from hydrogen peroxide by catalase degradation. Suitable catalase test will be apparent to the skilled artisan.

In yet another example, inactivation and/or killing of *H. pylori* is confirmed by performing a motility assay as described, for example, by Worku et al. 1999 *Microbiology* 145: 2803-2811.

In another example, the ability of a *H. pylori* or cell thereof to replicate and/or colonize the gastric mucosa of a mammal is determined using in vitro assay of *H. pylori* adherence to human gastric tissue. See e.g., Hemalatha et al. 1991, *J. Med. Microbiol* 35:197-202; Falk et al., 1993, *Proc. Natl. acad. Sci. USA.* 90:2035-2039; Hsieh et al. 2012 *Helicobacter* 17:466-477.

In another example, the ability of a *H. pylori* or cell thereof to replicate and colonize the gastric mucosa in a mammal is determined by analysis of in vivo stomach colonization infected animals e.g., mice. For example, *H. pylori* bacteria which has been cultured, and subjected to stress and/or inactivation and/or killing treatment e.g., as described according to any example hereof, is harvested and resuspended in sterile saline. As a positive control a culture of *H. pylori* known to be capable of replicating and colonizing the gastric mucosa of a mammal and which has not been the subjected to stressing and/or inactivation and/or killing treatment prior to inoculation challenge described below, is used. Suitable *H. pylori* capable of replicating and colonizing the gastric mucosa are known in the art. Briefly, a flask containing BHI broth plus 4% fetal calf serum (FCS) is inoculate with an aliquot of a positive control *H. pylori* stock and allowed to incubate for 25 to 48 hours at 37° C. in an atmosphere of 10% $CO_2$+5% $O_2$, shaking at 125 rpm, to yield a pure culture of *H. pylori* bacteria having the expected morphology to be used for infection. For challenge inoculum an optical density of a 1:10 dilution of the sterile saline suspension comprising the *H. pylori* bacteria which has been cultured, and subjected to stress and/or inactivation and/or killing treatment is read at 660 nm, and inoculum samples generating a reading of between 0.07 and 0.002 are used for inoculation of mice.

Alternatively, samples for inoculation comprising an amount of *H. pylori* bacteria which has been cultured and subjected to stress and/or inactivation and/or killing treatment in a range equivalent to between about $1 \times 10^7$ to $2 \times 10^{10}$ cells/ml or CFU/ml as determined e.g., by a haemocytometer, are used. For positive control *H. pylori*, an inoculum of about $1 \times 10^8$ cells is used. Six to 8 weeks old C57BL/6 mice (from Charles River Laboratories (Wilmington, Mass.) and/or BALB/c (from Charles River Laboratories (Wilmington, Mass.) are challenges orally with a dosage comprising an amount of bacteria in a range corresponding between $10^8$ to $10^{10}$ cells, preferably $10^9$ cells of *H. pylori* bacteria subjected to stressing and/or inactivation and/or killing treatment and an inoculum of about $1 \times 10^8$ cells comprising the control *H. pylori*, by gavage twice within a 1-week period, preferably at least one day separating each challenge.

Alternatively, mice are challenged by intragastric immunization wherein about 0.25 ml or about 0.5 ml or about 1 ml volumes comprising inoculum dosages as above are delivered into the stomach of lightly etherized mice by intubation through polyethylene tubing attached to a hypodermic syringe. If required, this procedure may be performed three times in a 5-day period, with 24 hours between dosing.

According to this example, for the purpose of analysing stomach colonization two weeks following challenge mice are sacrificed e.g., by $CO_2$ inhalation and stomachs and duodenum are removed for quantitative assessment of colonization. For example, the stomachs and duodenum are transferred to labelled sterile Petri plates containing 5-10 ml of sterile PBS, and are then transferred to a biosafety cabinet where the stomachs are opened by midline incision and the contents gently cleaned using sterile gauze. The antrum is visualized and aseptically dissected away from the rest of the stomach, which is discarded. The antral section is then diced, using sterilized single-edge razor blades, and the pieces placed in a pre-weighed 5 ml tube containing brain-heart infusion broth (BHI) media. If required, tubes containing antral sections are re-weighed to 0.001 g accuracy and placed in a biosafety cabinet. The sections may then be mechanically macerated e.g., using sterile plastic tissue homogenizers and serial 1:10, 1:100, and 1:1000 dilutions of the homogenates are made in BHI media. From each dilution tube a 100 µl aliquot is placed on a sterile BHI agar plate and a full plate spread is performed. For example, the media on which homogenates are plated contain BHI agar (Difco), 4% fetal bovine serum, bacitracin, nalidixic acid, amphoteracin B, and *Campylobacter* selective supplement (Oxoid, Lenexa, Kans.). Plates are placed in anaerobic jars containing BBL CampyPak Plus microaerophilic envelopes (Becton Dickinson, Franklin Lakes, N.J.; product #271045) and preferably incubated at 37° C. for 6-7 days. Growth control plates are included in each jar, inoculated with a freshly grown preparation of the positive control *H. pylori* supra. The limit of detection in this assay is approximately 500 *H. pylori* cells per gram of stomach tissue. Absence of *H. pylori* colonies indicates that the *H. pylori* is inactive and is unable to replicate and colonise the gastric mucosa. However, if colonies are observed on plates, colonies may be confirmed to be *H. pylori* by means as described in any example hereof e.g., using one urease activity assay and/or oxidase activity assay and/or catalase activity assay and/or by colony morphology.

In yet another example, the ability of a *H. pylori* or cell thereof to replicate and colonize the gastric mucosa in a mammal is determined by polymerase chain reaction (PCR) detection of colonization of *H. pylori* in conventional euthymic mice based on detection of the *H. pylori* 16S ribosomal gene sequence. See e.g. Smith et al., 1996, *Clinic. Diagn. Lab. Immuno.* 3:66-72. For example, *H. pylori* bacteria which has been cultured, and subjected to stress and/or inactivation and/or killing treatment e.g., as described according to any example hereof, is harvested and resuspended in sterile saline. If required, as a positive control a culture of *H. pylori* e.g., wild type (WT) *H. pylori*, known to be capable of replicating and colonizing the gastric mucosa of a mammal and which has not been the subjected to stressing and/or inactivation and/or killing treatment prior to inoculation challenge described below, is separately harvested and resuspended in sterile saline. Suitable *H. pylori* capable of replicating and colonizing the gastric mucosa are known in the art and are described herein. For challenge inoculum an optical density of a 1:10 dilution of the inoculum is read at 660 nm, and inoculum samples generating a reading of between 0.07 and 0.002 are used for inoculation of mice.

Alternatively, inoculum samples comprising an amount of bacteria in a range corresponding to between about $2 \times 10^7$ to $2 \times 10^8$ cells/ml or CFU/ml as determined for example by a haemocytometer, are used. Eight to 12 weeks old VAF and GF Swiss-Webster mice or VAF CD-1 mice (from Taconic Laboratories (Germantown, N.Y.)) and/or VAF-CD-1 mice (from Charles River Laboratories (Wilmington, Mass.) and/or C57BL/6 mice (from Charles River Laboratories (Wilmington, Mass.) and/or BALB/c (from Charles River Laboratories (Wilmington, Mass.) and/or SJL/J mice (from The Jackson Laboratory, Bar Harbor, Me., USA) are challenges orally with 0.5 ml of the *H. pylori* inoculum prepared as described above, by gavage twice within a 1-week period, preferably at least one day separating each challenge. All mice are housed in sterile microisolator cages with sterile water and mouse chow ad libitum. If required GF mice are maintained and manipulated using sterile GF procedure, in laminar flow hood with all surfaces sanitized, and cages for GF mice are autoclaved in sterile wrap, and water is also autoclaved and filter sterilized prior to use. To assess *H. pylori* colonisation of the gastric mucosa in challenged mice, about 1 to about 4 weeks post challenge, preferably about 4 weeks post challenge, mice are sacrificed e.g., by inhalation of $CO_2$ and stomachs are removed by aseptic techniques. Stomachs are then cut longitudinally, and the stomach contents are washed away by rinsing with sterile deionized $H_2O$. The stomach mucosa is then separated from the stomach lining tissue by gently scraping the mucosa with sterile glass microscope slides. Mucosa samples are then placed in Tris-sodium chloride-EDTA (TNE) buffer and stored on ice or frozen until DNA extraction for PCR analysis. Methods for extracting DNA from the mucosa suspensions for PCR analysis are known in the art and may be readily employed. For example, DNA are extracted by centrifuging the stomach mucosa suspension in TNE buffer for 3 min at 12,000 rpm. The supernatant is then removed, and the cell pellet is resuspended in 570 ml of TNE containing 1% Triton X-100 (Sigma) and 0.5 ml of lysozyme (Sigma) per ml. Samples are then incubated at 37° C. for 30 min. Next, 1 mg of proteinase K (Boehringer GmbH, Mannheim, Germany) per ml is added, and the mixture is incubated at 65° C. for 2 hours or at 37° C. overnight. The digest is mixed with an equal volume of phenol-chloroform-isoamyl alcohol (25:24:1) and then centrifuged at 10,000 3 g for 6 min. The top aqueous layer is then removed, and a second extraction with phenol-chloroform-isoamyl alcohol is preferably performed. The aqueous layer is then mixed with an equal volume of chloroform-isoamyl alcohol (24:1) and processed as in the previous two extractions. DNA is then precipitated by adding a $\frac{1}{10}$ volume of 3 M sodium acetate and 2 volumes of absolute ethanol and placing on dry ice for 20 min. DNA is pelleted by centrifugation as described above and rinsed with 70% ethanol. The pellet is preferably dried e.g., by speed vacuum and resuspended in 100 ml of 0.13 TE (13 TE is 10 mM Tris [pH 7.4], 0.1 mM EDTA). Samples are stored at 4° C. until the PCR is run.

PCR primers used for amplification of a DNA sequence of *H. pylori* encoding the 16S rRNA which are used include the upstream primer (HP forward) set forth in SEQ ID NO: 1 had having the sequence 5'-TTG GAG GGC TTA GTC TCT-3', and the downstream primer (HP reverse) set forth in SEQ ID NO: 2 and having the sequence 5'-AAG ATT GGC TCC ACT TCA CA-3'. The primers set forth in SEQ ID NO: 1 and SEQ ID NO: 2 are designed to 459 bp PCR product spanning bases 793 to 1252 of the *H. pylori* DNA sequence. SEQ ID NO: 1 and SEQ ID NO: 2 primers are designed based on a region of homology for six isolates of *H. pylori* listed in gene bank accession numbers U00679, U01328, U01329, U01330, U01331, and U01332 and which differs from the sequences listed for *H. felis* (gene bank accession number M57398), *H. muridarum* (gene bank accession number M80205), and *Campylobacter* sp. (gene bank accession number L04315). Accordingly use of these primers avoids cross-reactivity with closely related bacteria.

If required, internal PCT control DNA templates can also be constructed for use in the PCR reaction. See e.g, Smith et al, 1996 supra. For example, the 495-bp PCR product amplified from a WT *H. pylori* using the primers set forth in SEQ ID NO 1 and SEQ ID NO: 2 as described according to any example hereof, is closed into a multi-copy plasmid. Subsequently, an internal restriction fragment of 237 bp, conveniently flanked by SM sites, is deleted from within the cloned *H. pylori* DNA to create a template with perfect homology to the HP primers but from which a much shorter sequence would be amplified with those primers. The 459-bp PCR amplified *H. pylori* DNA fragment was purified by using a GENECLEAN® kit (Bio 101, Inc., La Jolla, Calif.) and ligated with T4 DNA ligase (GIBCO BRL, Gaithersburg, Md.) into the EcoRV site of plasmid pBLUESCRIPT II SKI® (Stratagene Co., La Jolla, Calif.), which confers ampicillin resistance and encodes the lacZa peptide. The recombinant plasmids are transformed into *Escherichia coli* DH5a (GIBCO BRL). Ampicillin-resistant transformants are selected on Luria broth plates containing X-Gal (5-bromo-4-chloro-3-indolyl-b-D-galactopyranoside), and plasmids carrying inserted DNA are identified as giving white colonies. Plasmids are extracted from selected colonies with the Qiagen plasmid purification kit (Qiagen Inc., Chatsworth, Calif.) and cut with Styl restriction endonuclease (New England BioLabs, Beverly, Mass.), which removes an internal 237-bp DNA fragment from the *H. pylori* DNA insertion. The remaining DNA is recirculized with T4 DNA ligase and transformed into strain DH5a, and colonies are selected as ampicillin resistant. Transformants yield the desired 222-bp fragment when amplified in PCRs with the HP primers set forth in SEQ ID NO: 1 and SEQ ID NO: 2. One transformant may be selected was selected, and plasmid DNA is extracted for use as the internal PCT control template.

PCT analysis is conducted by preparing master reaction mixtures, under sterile conditions. Each master mixture is made in in a 1.5-ml microcentrifuge tube and contains reactants for 45 sample reactions. To each master mix there is added 826.9 ml of deionized $H_2O$, 112.5 ml of 103 Taq buffer (Stratagene), 45 ml of deoxynucleoside triphosphate (5 mM), 22.5 ml of each primer of SEQ ID NO: 1 or SEQ ID N: 2 (25 to 50 mM), and 5.6 ml of Taq polymerase (5 U/ml; Stratagene). If required, the master mixtures are aliquoted at 23 ml per reaction into 200-ml PCR tubes. The volume of each reaction mixture for PCR is brought up to 25 ml by adding 2 ml of DNA templates extracted mouse mucosal DNA extracted above, typically comprising an amount of 2 mg of extracted DNA. If required, PCR reaction tubes are briefly centrifuged to mix reactants. PCR reaction mixtures containing the mucosal DNA extracted from mice challenged with *H. pylori* subject to stressing and/or inactivation and/or killing treatment and, if required, from negative control mice challenges with WT *H. pylori* are cycled in Perkin-Elmer 9600 System thermal cycler (Perkin-Elmer, Norwalk, Conn.). DNA is amplified for 35 cycles of 15 s at 94° C., 30 s at 55° C., and 1 min at 72° C., with a final elongation cycle at 72° C. for 10 min. Positive and negative control reactions may be perfumed performed with each amplification. If required, control templates in each PCR run may be used which consist of deionized $H_2O$, *H. pylori* DNA corresponding to 1, 10, and 100 cells, and mouse mucosal tissue DNA (2 mg). The PCR products are analyzed by 2% agarose gel electrophoresis with ethidium bromide incorporation and visualized under UV light. Detection of a PCR product is scored as colonization, while absence of a PCR product is scored as no-colonization, and provides a positive confirmation that the *H. pylori* is inactive and is unable to replicate and colonise the gastric mucosa of a mammal.

Other methods for measuring the utility of *H. pylori* or cell thereof in the compositions and/or methods as described in any example hereof will be apparent to the skilled artisan and are encompassed by the present invention.

6. Formulations

Inactivated and/or Killed *H. pylori* or Cell Lysates Thereof May be Formulated for Oral Administration to a Human or Mammal.

In one example, inactivated and/or killed *H. pylori* or a cell lysate thereof is encapsulated. As used herein, the term "encapsulated" shall be taken to mean that the inactivated and/or killed *H. pylori* or cell lysate is enclosed within a degradable barrier.

For example, the degradable barrier may degrade at a predetermined location in gastrointestinal tract.

In one example the composition is in the form of a tablet or a capsule.

In another example, composition of the present invention is lyophilised. In another example, the composition of the present invention is a powder.

Compositions of the present invention may be formulated as a foodstuff or dietary supplement. As used herein, the term "foodstuff" refers to any food product or beverage and the term "dietary supplement" refers to a product intended to supplement the diet of a human or mammal that comprises a vitamins and/or a mineral and/or a herb or other botanical and/or an acid.

In one example, the foodstuff or dietary supplement may be a ready-to-drink product. As used herein, the term "ready-to-drink" shall be taken to mean that the product is in a form suitable for oral administration without additional preparation. Suitable ready-to-drink products may include, for example, carbonated water, flavoured water, carbonated flavoured water, drinks containing juice (juice derived from any fruit or any combination of fruits, juice derived from any vegetable or any combination of vegetables), milk drinks obtained from animals, milk drinks derived from soy, rice, coconut or other plant material, yoghurt drinks, sports drinks, energy drinks, coffee, decaffeinated coffee, tea, tea derived from fruit products, tea derived from herb products, decaffeinated tea and liquid meal replacements. In one example, the ready-to-drink product may comprise filtered water, skim milk powder, cane sugar, wheat maltodextrin, soy protein, vegetable oils, starch, inulin, corn syrup solids, fructose, cereals, flavour, calcium, phosphorus, fermented red rice, vitamin C, Niacin, vitamin A, vitamin B12, vitamin B6, vitamin B2, vitamin BI, folate and salt. In another example, the ready-to-drink product may comprise include carbonated water, corn syrup, caramel color, caffeine, phosphoric acid, coca extract, lime extract, vanilla and glycerine. In yet another example, the ready-to-drink product may comprise carbonated water, sucrose, glucose, sodium citrate taurine, glucuronolactone, caffeine, inositol, niacinamide and vitamin B 12.

In another example, the foodstuff or dietary supplement may be a ready-to-eat product. As used herein, the term "ready-to-eat" shall be taken to mean that the product is in a form suitable for oral administration without additional preparation. Suitable ready-to-eat products may include, for example, a meal replacement bar, a protein bar, snack food and confectionary product. In one example, the ready-to-eat product may comprise wholegrain cereals, glucose, sugar, vegetable oil, maize starch, humectants, rice flour, oat flour, skim milk powder and honey.

In yet another example, the foodstuff or dietary supplement may require suspension and/or reconstitution in a liquid or diluent prior to administration. For example, the foodstuff or dietary supplement may be a liquid or liquid concentrate or powder.

In one example, the foodstuff or dietary supplement may be an infant formula or follow-on formula or infant formula for special dietary use or pre-term formula. As used herein, the term "infant formula" shall refer to a breast milk substitute which satisfies the nutritional requirement of infants aged up to about four to about six months. In one example, the infant formula may have an energy content of no less than about 2500 kJ/L and no more than about 3150 kJ/L. In one example, the infant formula may comprise an amount of protein between 0.45 g per 100 kJ and 0.7 g per 100 kJ, an amount fat between 1.05 g per 100 kJ and 1.5 g per 100 kJ. In another example, the infant formula may comprise less than 0.05 mg of aluminium per 100 mL. As used herein, the term "follow-on formula" shall refer to a breast milk substitute or a replacement for infant formula which constitutes the principal liquid source of nourishment for infants aged from about six months. For example, infant follow-on formula may have an energy content of no less than about 2500 kJ/L and no more than about 3550 kJ/L. In one example, the infant formula may comprise an amount of protein between 0.45 g per 100 kJ and 1.3 g per 100 kJ, an amount fat between 1.05 g per 100 kJ and 1.5 g per 100 kJ. In another example, the infant formula may comprise less than 0.05 mg of aluminium per 100 mL. The term "infant formula product for special dietary use" as used herein shall be taken to mean an infant formula product formulated to satisfy particular needs of infants with a particular metabolic and/or immunological and/or renal and/or hepatic and/or malabsorptive condition. For example, infant formula products for specific dietary use may have an energy content of no less than about 2500 kJ/L and no more than about 3550 kJ/L. In one example, the infant formula may comprise an amount of protein between 0.45 g per 100 kJ and 1.3 g per 100 kJ, an amount fat between 0.93 g per 100 kJ and 1.5 g per 100 kJ. In another example, the infant formula may comprise less than 0.05 mg of aluminium per 100 mL. The term "pre-term formula" shall be construed broadly to mean an infant formula product specifically formulated to satisfy particular needs of an infant born prior to 36 weeks of gestation. Preferably, pre-term formula may comprise an amount of protein between 0.45 g per 100 kJ and 1.3 g per 100 kJ, an amount fat between 0.93 g per 100 kJ and 1.5 g per 100 kJ. In another example, the infant formula may comprise less than 0.02 mg of aluminium per 100 mL.

Compositions of the invention may comprise one or more prebiotics or paraprobiotics or probiotics e.g., as a food, beverage, dietary supplement or animal feed.

The term "probiotic" used herein shall be taken to mean live microorganisms, which when administered in an adequate amount confers a health benefit on the host. Suitable probiotics include, for example, *Aspergillus niger, Aspergillus oryzae, Bacillus coagulans, Bacillus lentus, Bacillus licheniformis, Bacillus pumilus, Bacillus subtilis, Bacteroides amylophilus, Bacteroides capillosus, Bacteroides ruminocola, Bacteroides suis, Bifidobacterium adolescentis, Bifidobacterium animalis, Bifidobacterium bifidum, Bifidobacterium infantis, Bifidobacterium longum, Bifidobacterium thermophilum, Enterococcus cremoris, Enterococcus diacetylactis, Enterococcus faecium, Enterococcus intermedius, Enterococcus lactis, Enterococcus thermophilus, Lactobacillus acidophilus, Lactobacillus brevis, Lactobacillus bulgaricus, Lactobacillus casei, Lactobacillus cellobiosus, Lactobacillus curvatus, Lactobacillus delbruekii, Lactobacillus fermentum, Lactobacillus helveticus, Lactobacillus lactis, Lactobacillus plantarum, Lactobacillus reuteri, Leuconostoc mesenteroides, Pediococcus acidilacticii, Pediococcus pentosaceus, Propionibacterium freudenreichii, Propionibacterium shermanii, Saccharomyces cerevisiae.*

The term "paraprobiotic" has been coined to refer to those products comprising killed or inactivated microbes which may positively affect host health (Taverniti V and Guglielmetti S, 2011, *Genes Nutr.* 6(3): 261-274).

As used herein, the term "prebiotic" shall be taken to mean a non-digestible food ingredient that beneficially affects a host by selectively stimulating growth and/or activity of one or more microorganisms in the gut. Suitable prebiotics include, for example, fructooligosaccharides, transgalactooligosaccharides, inulins, acacia gum, xylooligosaccharides, isomaltooligosaccharides, lactulose and soy oligosaccharides.

7. Administration

Compositions of the present invention may be formulated for daily or periodic administration. For example, the composition may be administered daily for a period of at least about 1 week or at least about 2 weeks or at least about 3 weeks or at least about 4 weeks or at least about 5 weeks or at least about 6 weeks or at least about 7 weeks or at least about 8 weeks or at least about 9 weeks or at least about 10 weeks or at least about 11 weeks or at least about 12 weeks or at least about 13 weeks or at least about 14 weeks or at least about 15 weeks or at least about 16 weeks or at least about 17 weeks or at least about 18 weeks or at least about 19 weeks or at least about 20 weeks or at least about 21 weeks or at least about 22 weeks or at least about 23 weeks or at least about 24 weeks or at least about 25 weeks, or at least about 6 months, or at least about one year or more than one year. Preferably, the composition is administered, over a period of at least about 13 weeks or at least about 3 months.

In another example, the composition may be administered periodically, such as, for example, every second day or every third day or every fourth day or every fifth day or every sixth day or every second week for a period of at least about 1 week or at least about 2 weeks or at least about 3 weeks or at least about 4 weeks or at least about 5 weeks or at least about 6 weeks or at least about 7 weeks or at least about 8 weeks or at least about 9 weeks or at least about 10 weeks or at least about 11 weeks or at least about 12 weeks or at least about 13 weeks or at least about 14 weeks or at least about 15 weeks or at least about 16 weeks or at least about 17 weeks or at least about 18 weeks or at least about 19 weeks or at least about 20 weeks. In yet another example, the composition may be administered intermittently. For example, the composition may be administered for an administration period at least about 1 week or at least about 2 weeks or at least about 3 weeks or at least about 4 weeks or at least about 5 weeks or at least about 6 weeks or at least about 7 weeks or at least about 8 weeks or at least about 9 weeks or at least about 10 weeks or at least about 11 weeks or at least about 12 weeks or at least about 13 weeks or at least about 14 weeks or at least about 15 weeks or at least about 16 weeks or at least about 17 weeks or at least about 18 weeks or at least about 19 weeks or at least about 20 weeks or at least about 21 weeks or at least about 22 weeks or at least about 23 weeks or at least about 24 weeks or at least about 25 weeks, or at least about 6 months, followed by a period of discontinuance, followed by an administration period at least 1 week or at least 2 weeks or at least 3 weeks or at least 4 weeks or at least 5 weeks or at least 6 weeks or at least 7 weeks or at least 8 weeks or at least 9 weeks or at least 10 weeks or at least 11 weeks or at least 12 weeks or at least 13 weeks or at least 14 weeks or at least 15 weeks or at least 16 weeks or at least 17 weeks or at least 18 weeks or at least 19 weeks or at least 20 weeks or at least about 21 weeks or at least about 22 weeks or at least about 23 weeks or at least about 24 weeks or at least about 25 weeks, or at least about 6 months. Preferably, wherein the composition is administered for a period of at least about 13 weeks or at least about 3 months, followed by a period of discontinuance, and then followed by an administration period of at least about 13 weeks or at least about 3 months. In another example, the composition may be administered for an administration period of at least 1 or 2 or 3 or 4 of 5 or 6 or 7 or 8 or 9 or 10 or 15 or 20 or 25 or 30 or 35 or 40 years.

In one example, compositions may be formulated as a daily dosage comprising *H. pylori* or cell lysate thereof in an amount corresponding to about $10^6$ cells or about $10^7$ cells or about $10^8$ cells or about $10^9$ cells or about $10^{10}$ cells or about $10^{11}$ cells or about $10^{12}$ or between about $10^6$ cells to about $10^{12}$ cells or between about $10^7$ cells to about $10^{11}$ cells or between about $10^8$ cells to about $10^{10}$ cells or between about $10^9$ cells to about $10^{10}$ cells. As will be apparent to the skilled artisan, single or multiple dosage units may be administered to make up the daily dosage.

In another example, compositions may be formulated for administration to infants aged between 0 to about 5 years, or between 0 to about 4 years, or between 0 to about 3 years, or between 0 to about 2 years, or between 0 to about 1 year. In one example, the composition may be formulated for administration to infants aged between 0 to about 2 years. In another example, the composition may be formulated for administration to infants of an age between about 4 months and about 12 months. In another example, the composition may be formulated for administration to infants less than about 6 months of age.

In yet another example, compositions may be formulated for administration to children older than about 5 years of age and/or to adolescents and/or to adults.

In a further example, a composition of the invention according to any example hereof is a cosmetic or a nutraceutical formulation such as a food stuff, tablet, capsule, or liquid drink, for administration to a subject not suffering from a medical condition referred to herein such as allergy or one or more of allergic eczema, urticaria, hives, rhinitis, wheezing, airway resistance, airway restriction, lung inflammation, food allergy, or asthma or in need of prevention of such medical condition. For example, a cosmetic or a nutraceutical formulation of the present invention will promote a general sense of wellbeing and/or boost the immune system and/or provide balance to the immune system of a subject not in need of therapy or prophylaxis from any medical condition(s).

In one example, the present invention provides a method of cosmetic or nutraceutical use comprising administering a composition comprising inactivated and/or killed *H. pylori* or a cell lysate thereof according to any example hereof to a subject not suffering from a medical condition referred to herein such as allergy or one or more of allergic eczema, urticaria, hives, rhinitis, wheezing, airway resistance, airway restriction, lung inflammation, food allergy, or asthma or in need of prevention of such medical condition. In one such example, the method of the present invention promotes a general sense of wellbeing and/or boost the immune system and/or provide balance to the immune system of a subject not in need of therapy or prophylaxis from any medical condition(s).

The present invention is described further in the following non-limiting examples:

Example 1

Treatment to Inactivate and/or Kill *H. pylori* Cells—Method I

This example demonstrates the utility of ultraviolet irradiation, and optional additional freeze-thawing, for inactivating and/or killing *H. pylori* cells.

Cells of *Helicobacter pylori* strain OND79 deposited with the National Measurement Institute (NMI) of Australia under Accession No. V13/023374 were obtained by growth on Columbia agar (CBA) plates comprising Columbia agar base (Product Code CM0311, Thermo Fisher Scientific, Oxoid Ltd) and 7% (v/v) sterile defibrinated horse blood for 24 hours and harvesting cells by resuspension of grown cells in saline solution [0.9% (w/v) sodium chloride] and then centrifugation, according to standard procedures. The cells were then resuspended in saline solution, and the concentration of resuspended cells was adjusted to a measured absorbance at 600 nm wavelength of 1 optical density (OD) unit per ml. Equal volumes (1 ml) of resuspended cells were plated onto CBA plates comprising 7% (v/v) sterile defibrinated horse blood. The plates were incubated for 24 hours at 37° C. in a microaerobic environment containing 5% (v/v) $CO_2$ and less than 5% (v/v) $O_2$.

Plate samples were then subjected to ultraviolet irradiation using ultraviolet C (UV-C) light (wavelength between 200 and 290 nm) in Bio-Link BLX crosslinker UV chamber (Vilber Lourmat, France) at an irradiance of 4 Joules/cm$^2$ or 12 Joules/OD$_{600}$ of plated cells. For example, a plate of 9 cm diameter may be irradiated by exposure to about 240 Joules UV-C. Irradiated bacteria were then collected from the plates, resuspended in the saline solution and the concentration of resuspended cells was adjusted to a measured absorbance at 600 nm wavelength of 20 optical density (OD) unit per ml.

As untreated control, OND79 *H. pylori* cells which were cultured, harvested and plated as described above but which were not irradiated using UV-C were also collected and resuspended in a saline solution and the concentration of untreated resuspended cells was adjusted to a measured absorbance at 600 nm wavelength of 20 optical density (OD) unit per ml.

Aliquots of the irradiated cells were assayed directly to determine cell replication ability and urease activity, or alternatively, frozen at −20° C. and then thawed, prior to cellular replication and urease testing being performed.

To test for an ability of irradiated cells, optionally subjected to irradiation and freeze-thawing, to replicate, the bacterial suspensions were serially-diluted in saline, plated onto CBA plates, and the plates incubated for 3 days at 37° C. in a microaerobic environment containing 5% (v/v) $CO_2$ and less than 5% (v/v) $O_2$. Cell counts were then determined for the various dilutions tested.

In two independent experiments, no colony forming units were identified for suspensions in a concentration range corresponding to a measured absorbance at 600 nm wavelength of 0.056-3.6 OD units per ml. The same results were obtained for cells receiving only UV-C as for cells receiving UV-C and a cycle of freeze-thawing.

Urease activities of the treated cells were determined by standard assay of resuspended cells. Briefly, 25 μl of urease buffer comprising 0.1 M citrate, 2 g/l urea and phenol red 0.01% was added to an equal volume of treated cell suspension, and the pH of the mixture was determined at room temperature over a period of 30 mins. In this assay, a change in assay sample colour from yellow to red is indicative of an increase in pH due to breakdown of urea and production of ammonia. Data obtained for two independent experiments indicates that UV-C irradiated cells had residual urease activity relative to untreated cells, estimated to be less than 10% of the urease activity of untreated *H. pylori* cells e.g., prior to UV irradiation.

Consistent with the reduced urease activity of the irradiated cells, SDS/PAGE of extracts from *H. pylori* cells exposed to UV-C irradiation demonstrate that the irradiated cells undergo protein degradation, and aggregation of proteins into high molecular weight complexes, compared to untreated cells (data not shown). In a UV-C dosage range of 1-4 J/cm$^2$, the level of such degradation and aggregation is dose-dependent i.e., a higher UV-C dose e.g., 2 J/cm$^2$ or 4 J/cm$^2$, produces increased degradation and aggregation (data not shown).

Collectively, the data indicate that UV-C irradiation and optionally, additional freeze-thawing of *H. pylori*, provides an effective means for inactivating and/or killing *H. pylori*.

Example 2

Treatment to Inactivate and/or Kill *H. pylori* Cells—Method II

This example demonstrates the utility of ultraviolet irradiation or oxygen restriction, and optional additional heat treatment following ultraviolet irradiation or oxygen restriction and/or by heat treatment alone, for inactivating and/or killing *H. pylori* cells.

Cells of *H. pylori* strain OND79, or cells of *H. pylori* strain OND86 deposited with the National Measurement Institute (NMI) of Australia under Accession No. V14/013016 (described in Example 15), or cells of *H. pylori* strain J99 were grown on Columbia agar (CBA) plates comprising Columbia agar base (Product Code CM0311, Thermo Fisher Scientific, Oxoid Ltd) and 7% (v/v) sterile defibrinated horse blood for 24 hours and harvesting cells by resuspension of grown cells in saline solution [0.9% (w/v) sodium chloride] and then centrifugation, according to standard procedures. The cells were then resuspended in saline solution, and the concentration of resuspended cells was adjusted to a measured absorbance at 600 nm wavelength of 1 optical density (OD) unit per ml. Equal volumes (1 ml) of resuspended cells were plated onto CBA plates comprising 7% (v/v) sterile defibrinated horse blood. The plates were incubated at 37° C. in a microaerobic environment containing 5% (v/v) $CO_2$ and less than 5% (v/v) $O_2$ for 24 hours if cells were then subjected UV irradiation or, alternatively, for 18 hours if the cells were then subjected to oxygen starvation.

After 24 hours at microaerobic conditions plate samples were then subjected to ultraviolet irradiation using UV-C light, and the irradiated bacteria were then collected from the plates, resuspended in the saline solution and the concentration of resuspended cells was adjusted to a measured absorbance at 600 nm wavelength of 20 optical density (OD) unit per ml, as described in Example 1. Optionally, the resuspended cells were then subjected to heat treatment by exposure to a first elevated temperature of about at 70° C. for 10 minutes immediately followed by exposure to a second elevated temperature of about 94° C. or 95° C. for 5 minutes at normal atmosphere conditions.

Alternatively, after 18 hours incubation in microaerobic conditions as described above, cultured *H. pylori* cells were then subjected to oxygen restriction treatment depleting the *H. pylori* cultures of oxygen by transferring the plates to plates hermetically sealed jars containing gas sachets (AnaeroGen, AN0025A, ThermoScientific) to generate anaerobic conditions. Plates were then incubated at under anaerobic conditions at 37° C. for periods of 24 h or 48 hours or 72 hours. The bacteria which were subjected to oxygen starvation treatment were then collected from the plates, resuspended in the saline solution and the concentration of resuspended cells was adjusted to a measured absorbance at 600 nm wavelength of 20 optical density (OD) unit per ml. Optionally, the resuspended cells were then subjected to heat treatment by exposure to a first elevated temperature of about at 70° C. for 10 minutes immediately followed by exposure to a second elevated temperature of about 94° C. or 95° C. for 5 minutes at normal atmosphere conditions.

Alternatively, *H. pylori* cells which had been cultured on CBA plates for 24 hours at microaerobic conditions as described above were resuspended in the saline solution and the concentration adjusted to a measured absorbance at 600 nm wavelength of 20 optical density (OD) unit per ml. The resuspended cells were then subjected to inactivation and/or killing by heat treatment alone by exposing the cells to a first elevated temperature of about 70° C. for 10 minutes and then to a second elevated temperature of about 94° C. or 95° C. for 5 minutes at normal atmosphere conditions.

To test for the ability of *H. pylori* treated cells to replicate, bacterial suspensions of live untreated *H. pylori* OND86 cells (live control) and bacterial suspensions of *H. pylori* OND86 cells that were subjected to ultraviolet irradiation using UV-C light (UV) and optionally further subjected to heat treatment (UV+heat) or which were subjected to oxygen starvation treatment for 48 hours ($O_2$ restriction) and optionally further subjected to heat treatment ($O_2$ restriction+heat), were serially-diluted in saline, plated onto CBA plates, and the plates incubated for 3 days at 37° C. in a microaerobic environment containing 5% (v/v) $CO_2$ and less than 5% (v/v) $O_2$. Cell counts were then determined for the various dilutions. Results obtained from two independent experiments are shown in FIG. 2. The results indicate that treatment of *H. pylori* cells by UV irradiation, UV irradiation and heat treatment, oxygen restriction and heat treatment abolished the ability of treated *H. pylori* cells to replicate and form colonies. Although in one independent experiment where *H. pylori* cells were subjected to oxygen restriction for 48 hours without further heat treatment resulted in *H. pylori* colonies on CBA plates, the ability of the treated cells to replicate was substantially reduced relative to untreated live *H. pylori*. In a further independent experiment, *H. pylori* cells which were subjected to heat treatment alone to inactivate and/or kill the cells consistently generated no colonies on CBA plates (data not shown), indicating that exposure to heat treatment alone e.g., as described herein also abrogates replication capabilities of *H. pylori* cells.

To test for the effect of various oxygen restriction treatment periods on the ability of *H. pylori* cells to replicate, *H. pylori* OND86 cells which were subjected to oxygen restriction for periods of 24 hours, or 48 hours or 72 hours without additional heat treatment, were collected from the plates after incubation under anaerobic conditions as described above, resuspended in the saline solution and the concentration of resuspended cells was adjusted to a measured absorbance at 600 nm wavelength of 1 optical density (OD) unit per ml, and seeded onto fresh CBA plates after serial 10-fold dilution. Plates were then incubated for 3 days at 37° C. in a microaerobic environment containing 5% (v/v) $CO_2$ and less than 5% (v/v) $O_2$. *H. pylori* were able to form colonies after 24 hours of oxygen restriction treatment, however, following 48 hours of oxygen restriction *H. pylori* cultures demonstrated limited growth on CBA plates, and after 72 hours of oxygen restriction no *H. pylori* colonies were formed on the CBA plates (results not shown). These results indicate that treatment of live *H. pylori* cells by oxygen restriction for a period of about 48 hour or more e.g., between 48 hours to 72 hours or more is effective in reducing and/or preventing replication ability of *H. pylori* thereby inactivating and/or killing *H. pylori* cells.

Urease activities of bacterial suspensions of live untreated *H. pylori* OND86 cells (live control) and bacterial suspensions of *H. pylori* OND86 cells that were subjected to ultraviolet irradiation using UV-C light (UV) and optionally further subjected to heat treatment (UV+heat) or which were subjected to oxygen starvation treatment for 48 hours ($O_2$ restriction) were and optionally further subjected to heat treatment ($O_2$ restriction+heat), were determined by the standard urease test. Briefly, 25 µl of urease buffer comprising 0.1 M citrate, 2 g/l urea and phenol red 0.01% was added to an equal volume of live untreated cells and treated cell suspension, and the pH of the mixture was determined spectrophotometrically at 560 nm after incubation of the cells at room temperature over a period of 5 mins. In this assay, a qualitative urease activity was determined as a measure of metabolic activity of the treated cells. *H. pylori* urease enzyme activity was evaluated based on a change in assay sample colour from yellow to red is indicative of an increase in pH due to breakdown of urea and production of ammonia.

Results of the qualitative urease activity are provided in Table 1 below.

TABLE 1

Qualitative Urease Activity.

| Treatment of H. pylori OND86 cells | Urease activity |
|---|---|
| No treatment (live control cells) | ++ |
| UV irradiation (UV) | −/+ |
| UV irradiation + heat | − |
| O$_2$ restriction | ++ |
| O$_2$ restriction + heat | − |

Enzymatic activity was evaluated based on the change of colour from yellow to red measured at 560 nm after incubation of the cells at room temperature over a period of 5 mins. Four qualitative levels were used; negative, −; weak, −/+; moderate, +, strong ++. Treatment of H. pylori OND86 cells are as indicated above.

In a second, independent, experiment urease activity of bacterial suspensions of live untreated H. pylori OND86 cells (live control) and bacterial suspensions of treated H. pylori OND86 cells was performed by the urease test as above, except that urease enzyme activity was measured at 560 nm after 1 minute incubation of the cells at room temperature. The urease activity of the live untreated bacteria was set at 100%, and the relative urease activity reading output for treated i.e., inactivated and/or killed bacteria was calculated as a percentage of the urease activity measured for the live untreated H. pylori. In this experiment suspensions H. pylori OND86 cells were also tested for urease activity following heat treatment alone i.e., by exposure to elevated temperature of about 70° C. for 10 minutes and then about 94° C. or 95° C. for 5 minutes as described above. The results of the urease activity of H. pylori cells subjected to heat treatment alone (Heat), UV-C irradiation (UV) and optionally further heat treatment (UV+heat), oxygen starvation for 48 hours (O$_2$ res) and optionally further heat treatment (O$_2$ res+heat), relative to the urease activity readout of the live untreated cells is shown in FIG. 3.

The results shown in FIG. 2 and the urease activity results shown in Table 1 and FIG. 3 indicate that although treatment to inactivate and/or kill H. pylori e.g., by way of UV treatment alone, UV plus heat treatment, oxygen starvation plus heat, or by heat treatment alone, can abrogate replication ability of H. pylori, the treated cells display residual metabolic activity as determined by the urease test.

To further investigate the metabolic activity of treated H. pylori cells, the ability of treated H. pylori cells to respire was evaluated by measuring the membrane redox potential of treated cells by flow cytometry using the BacLight™ RedoxSensor™ CTC (product catalogue No. B34956) from Invitrogen (Molecular Probes™ Invitrogen detection technologies) according to manufacturer's instructions. Live cells of H. pylori OND86 strain were subjected to heat treatment alone, oxygen starvation for 48 hours and optionally further heat treatment, or UV-C irradiation and optionally further heat treatment as described above to inactivate and/or kill the cells. Approximately the equivalent of $10^7$ cells per tune were incubated with 5-cyano-2,3-ditolyl tetrazolium chloride (CTC) in the dark for 6 hours and then fixed by addition of 4% formaldehyde according to manufacturer's instructions. The ratio of the redox potential obtained by FACS analysis for live untreated H. pylori cells relative or cells which were treated by oxygen starvation or UV-C irradiation relative to the redox potential obtained for the live or treated cells after heat treatment was calculated to normalize the redox potential of the different inactivation and/or killing treatment regimes. Without being bound by any specific theory of mode of action, the present inventors speculated that heat treatment of H. pylori cells as described herein may lead to destruction of the majority of metabolic activity in treated cells and may further result in alteration of cell shape and/or cell aggregation patterns. Accordingly, to take into account variations in FACS cells sorting arising from differences in cell shape or cell aggregation that may arise due to heat treatment of cells, normalization of the redox potential for cells following heat treatment was performed. The results are shown in FIG. 4. The results show that both live and UV-C treated cells were metabolically active and were respiring before heat treatment (ratio of 0.85 and 1.1, respectively), whereas treatment of live H. pylori cells by exposure to oxygen restriction led to a ratio of 0.1 indicating that treatment of cells by oxygen starvation significantly attenuated metabolic activity of H. pylori. Treatment by oxygen restriction resulted in 8.5-fold decrease in the redox potential ratio compared to redox potential ration obtained for live cells, but UV-C irradiation had little effect on the redox potential ratio relative to live cells.

Collectively, the herein data indicate that UV-C irradiation and optionally heat treatment of cells, or oxygen starvation and optionally heat treatment of cells, provide an effective means for inactivating and/or killing H. pylori.

Example 3

H. pylori Improves Outcomes of Allergic Asthma in the OVA Model of Allergic Airways Disease Adult C57BL/6 mice (6 to 8 weeks) were infected with wild-type H. pylori (WT), wild-type H. pylori expressing the asthma inducing antigen (OVA), or treated H. pylori (KD), or left uninfected. The H. pylori inocula comprised 0.2 ml of a suspension of H. pylori strain OND79 cells in saline solution adjusted to a measured absorbance at 600 nm wavelength of 20 OD unit per ml. Treated H. pylori were inactivated and/or killed as described in Example 1. Eight (8) weeks later, an allergic asthma phenotype was induced by sensitized mice with OVA/alum i.p. (day 0 and 14) and then challenged with OVA aerosol for 5 days from day 21-25. Control mice were uninfected, sensitised and challenged (positive) or only sensitised (negative). On day 26 mice received methacholine (MCh) challenge at increasing doses and airway resistance in the lungs was measured. FIG. 5 shows that H. pylori protected mice from induction of an allergic asthma phenotype.

Example 4

H. pylori Reduces Total Cell Count and Eosinophilia in the OVA Model of Allergic Airways Disease Adult C57BL/6 mice (6 to 8 weeks) were infected orally by gavage with wild-type H. pylori (WT), wild-type H. pylori-expressing the asthma inducing antigen (HpOVA), treated H. pylori (KD) or left uninfected. The H. pylori inocula comprised 0.2 ml of a suspension of H. pylori strain OND79 cells in saline solution adjusted to a measured absorbance at 600 nm wavelength of 20 OD unit per ml. Treated *H. pylori* were inactivated and/or killed as described in Example 1. Eight (8) weeks later, an allergic asthma phenotype was induced by sensitised mice with OVA/alum i.p. (day 0 and 14) and then challenged with OVA aerosol for 5 days from day 21-25. Control mice were uninfected, sensitised and challenged (positive) or only sensitised (negative). On day 26 mice were sacrificed and bronchioalveolar lung fluid collected. Total cell counts (Panel A) and eosinophil counts (Panel B) in the BALF were enumerated and the average number of eosinophils recruited to the lung is represented from 10 mice per group. FIG. 6 shows that *H. pylori* reduces total cell count and eosinophilia.

Example 5

*H. pylori* Decreases OVA-Specific IgE and OVA-Specific IgG Response in the OVA Model of Allergic Airways Disease Adult C57BL/6 mice were infected orally by gavage with wild-type *H. pylori* (WT), wild-type *H. pylori*-expressing the asthma inducing antigen (HpOVA), treated *H. pylori* (KD) or left uninfected. The *H. pylori* inocula comprised 0.2 ml of a suspension of *H. pylori* strain OND79 cells in saline solution adjusted to a measured absorbance at 600 nm wavelength of 20 OD unit per ml. Treated *H. pylori* were inactivated and/or killed as described in Example 1. Eight (8) weeks later, mice were sensitized with 20 µg OVA/1 mg alum i.p. (day 0 and 14) and then challenged intranasally with 2 µg OVA in saline for 4 days from day 21-24. Control mice were uninfected, sensitised and challenged (positive) or only sensitised (negative). On day 25 mice were bled and OVA-specific IgE (Panel A) and IgG (Panel B) antibodies were measured from serum, diluted 1:60 and 1:6000 respectively, by ELISA. Results are expressed as the individual and average absorbance at $OD_{405}$ nm. FIG. 7 shows that *H. pylori* decreases OVA-specific IgE (Panel A) and OVA-specific IgG (Panel B) response in the ova model of allergic airways disease.

Example 6

*H. pylori* Reduces IL-13

Adult C57BL/6 mice were infected orally by gavage with *H. pylori* (WT), treated bacteria (KD) or left uninfected. The *H. pylori* inocula comprised 0.2 ml of a suspension of *H. pylori* strain OND79 cells in saline solution adjusted to a measured absorbance at 600 nm wavelength of 20 OD unit per ml. Treated *H. pylori* were inactivated and/or killed as described in Example 1. As a comparator, *H. pylori* strain 10700 was also tested. 8 weeks later, mice were sensitized with 20 µg OVA/1 mg alum i.p. (day 0 and 14) and then challenged intranasally with 2 µg OVA in saline for 4 days from day 21-24. Control mice were uninfected, sensitised and challenged (positive) or only sensitised (negative). On day 25 bronchioalveolar lung fluid (BALF) was collected from the lungs of anaesthetised mice. IL-13 was measured from undiluted BALF using cytokine bead array and expressed as the average of 10 mice per group in pg/ml. FIG. 8 shows that IL-13 is reduced in the lungs of *H. pylori*-infected mice in the allergic asthma model.

Example 7

*H. pylori* Reduces OVA-Specific CD8 T Cells

Adult C57BL/6 mice were infected orally by gavage with ~1×10$^9$ CFU *H. pylori* (WT) or left uninfected for 8 months then received 2 doses of 20 µg OVA/2 mg alum on day 0 and 28. The *H. pylori* inocula comprised 0.2 ml of a suspension of *H. pylori* strain OND79 cells in saline solution adjusted to a measured absorbance at 600 nm wavelength of 20 OD unit per ml. One day prior to OVA/alum challenge, mice received 5×10$^4$ MACS purified CD8 OT-I cells i.v. Spleens were harvested on day 35 and single cell suspension of spleen cells was stimulated with SIINFEKL peptide for 4 hours in presence of BrefA. Intracellular cytokine staining was performed to measure IFNγ secretion by FACS. CD8 OT-I cells were identified by CD45.1 expression. Colonization results from the stomach showed that all WT infected mice were colonized. *H. pylori* reduces the OVA-specific CD8 T cell response and impairs function of OVA-specific CD8 T cells. FIG. 9 shows the decreased number (panel A) and function (panel B) of OVA-specific CD8 T cells in *H. pylori* infected mice compared to control mice after OVA/alum challenge.

Example 8

*H. pylori* Decreases Antigen-Specific IgG

Adult C57BL/6 mice were infected orally by gavage with ~1×10$^9$ CFU *H. pylori* (WT) or left uninfected for 8 weeks then injected i.p. with 20 µg OVA/alum. 14 days later serum was collected and OVA-specific IgG determined by ELISA.

In some mice a secondary i.p. dose of OVA/alum was administered at day 14. No differences in OVA-specific IgG titres was observed at day 21 (7 days after boost). Mice are able to overcome *H. pylori*-mediated immune suppression in the presence of sufficient immunological stimulus. FIG. 10 (panel A) shows decreased antigen-specific IgG in *H. pylori*-infected compared to control mice after primary OVA/alum challenge. FIG. 10 (panel B) shows antigen specific IgG response 7 days after secondary challenge.

Example 9

*H. pylori* Reduces Responsiveness of CD4 and CD8 T Cells

Adult C57BL/6 mice were infected orally by gavage with ~1×10$^9$ CFU *H. pylori* (WT) or left uninfected. 7 months after challenge spleen cells were isolated and single suspensions of cells stimulated with PMA/ionomycin for 4 hours in the presence of Brefeldin A. Numbers of IFNγ CD4+ and CD8+ T cells were assessed using intracellular cytokine staining and FACS. FIG. 11 shows the reduced responsiveness of CD4 and CD8 T cells from *H. pylori* infected mice to non-specific stimulus.

Example 10

Effect of *H. pylori* Colonisation in the Neonatal Allergic Asthma Model 5-day old female C57BL/6 mice (n=5-10) were fed ~10$^9$ CFU live *H. pylori* for 5 consecutive days or left uninfected. 8 weeks later, mice were sensitized with 2 doses of 50 µg OVA/1 mg alum i.p. (day 0 and 14) and then challenged with OVA aerosol for 5 days from day 21-25. Control mice were uninfected, sensitised and challenged (positive control, i.e., untreated allergic mice) or only sensitised (negative control, i.e., untreated healthy mice). On day 26 mice received metacholine (MCh) at increasing doses and airway hyperresponsiveness (AHR) of lung tissue was measured and bronchio-alveolar lung fluid (BALF) collected.

FIG. 12, in panel A, shows the results in which AHR results are expressed as the average cmH2o.s/ml per group of mice. Statistical significance was determined using a one-sided student's t-test assuming a normal Gaussian distribution where p<0.5. The non-parametric Wilcoxon rank test that is suitable for non Gaussian distribution showed statistical significance at the three highest concentration of MCh. In FIG. 12, panel B, total cell infiltrate from the lungs was determine and is expressed at the average number of live total cells from BALF per group of mice. Bars represent standard deviation from the mean. Statistical significance was determined using a one-sided student's t-test assuming a normal Gaussian distribution where p<0.5.

The results herein demonstrate that *H. pylori* reduces symptoms of allergic asthma. FIG. 12 (panel A) shows that airway resistance increased in allergic adult mice not infected with live *H. pylori*, whereas mice challenged with live *H. pylori* from day 5 exhibited comparable airway resistance to that of non-allergic mice. FIG. 12 (panel B) further demonstrates that *H. pylori* colonization prevents cellular infiltration in the lungs after allergen challenge and that the total cell count was similar to non-allergic control mice. Accordingly, live *H. pylori* protects neonatal mice from developing allergic asthma in response to allergen exposure later in life and reduces cellular infiltrate in the lungs.

FIG. 12 demonstrates that *H. pylori* colonization e.g., in neonates improves outcomes of allergic airways disease and reduces risk of developing allergic airway disease, for example as shown using the neonatal allergic asthma model described herein.

Example 11

Effect of *H. pylori* on Immunological Outcome in a Neonatal Allergic Asthma Model The present inventors inter alia conduct a side-by-side comparison of the effects on protection against allergic disease, such as allergic airway disease, achieved by administration of live colonizing bacteria or repeated oral administration of treated *H. pylori* to neonatal mice. The *H. pylori* inocula comprised 0.2 ml of a suspension of *H. pylori* strain OND79 cells in saline solution adjusted to a measured absorbance at 600 nm wavelength of 20 OD unit per ml. Treated *H. pylori* were inactivated and/or killed as described in Example 1. Briefly, 5-day old C57BL/6 mice (n=10) were fed ~$10^9$ CFU live *H. pylori* for 5 consecutive days or treated bacteria (for 3 days per week, for 10 weeks) or left untreated. 8 weeks later, mice were sensitized with 2 doses of 50 µg OVA/1 mg alum i.p. (day 0 and 14) and then challenged with OVA aerosol for 5 days from day 21-25. Control mice were uninfected, sensitised and challenged (positive control i.e., untreated allergic mice) or only sensitised (negative control i.e., untreated healthy mice). On day 26 mice were sacrificed and serum and bronchio-alveolar lung fluid (BALF) collected. Total cell infiltrate per group of mice in the lungs was determined and is expressed as the individual and average number of live total cells from BALF. As shown in FIG. 13 administration of either treated or live *H. pylori* effectively reduced cellular infiltration in the lungs of *H. pylori* treated mice (Panel A). In addition, allergen (OVA)-specific IgE antibodies were measured by standard ELISA methods from serum diluted 1:60. Antibody titres were expressed as the individual and average absorbance at $OD_{405}$ nm. As shown in FIG. 13 (panel B), administration of either treated *H. pylori* or live *H. pylori* also reduced allergic allergen-specific IgE antibodies in *H. pylori* treated subjects. *Statistical significance was determined using a one-sided student's t-test assuming a normal Gaussian distribution where p<0.5. Collectively, the data illustrated in panels (A) and (B) of FIG. 13 demonstrate that administration of treated i.e., inactivated and/or killed (or live) *H. pylori* is effective in reducing allergic inflammation and/or allergic immune responses.

Inflammatory cytokines, IL-5 and IL-13 were measured from undiluted BALF using a cytokine bead array kit and results are expressed as the average concentration of cytokine per group in pg/ml and shown in FIG. 13 (panels C and D). The results shown in FIG. 13 (panels C and D) demonstrate that administration of treated (or live) *H. pylori* was successful in reducing production of cytokine mediators and biological markers of asthma and allergic respiratory disease, IL-5 and IL-13, in the lungs.

In another experiment as shown in FIG. 14, the present inventors also demonstrated that adult and neonatal mice administered with treated (i.e., inactivated and/or killed) or live *H. pylori* had reduced allergic airway resistance response. Lung airway hyperresponsivness (AHR) was measured using 5-day old female C57BL/6 mice (n=5-10) as well as adult C57BL/6 mice (6-8 weeks, n=10) essentially as described in Example 10. In brief, neonatal and adult mice were fed ~$10^9$ CFU/dose of treated bacteria, 3 times per week for 8 weeks or fed ~$10^9$ CFU/dose of live freshly cultured bacteria for 6 consecutive days. Treated *H. pylori* were inactivated and/or killed as described in Example 1. On day 0 and 14, all mice received intraperitoneal OVA/alum. The allergic asthma phenotype was induced with 1% OVA aerosol for 5 consecutive days from day 21. Control mice were uninfected, sensitised and challenged (positive control, i.e., untreated allergic mice) or only sensitised (negative control, i.e., untreated healthy mice). In other words, positive and negative controls did not receive bacteria. On day 26 mice received metacholine (MCh) at increasing doses and airway hyperresponsiveness (AHR) of lung tissue in response to MCh challenge was measured, and mice were sacrificed.

As shown in FIG. 14, panel A, allergic adult mice which did not receive *H. pylori* (positive control) showed elevated airway resistance after allergen challenge compared with airway resistance of adult mice which received a formulation of treated *H. pylori* or live *H. pylori*. As shown in FIG. 14, panels B and C, allergic neonatal mice which did not receive *H. pylori* (positive control) showed elevated airway resistance after allergen challenge compared with airway resistance of neonatal mice which received a formulation of treated *H. pylori* or live *H. pylori*. The results shown in panels A, B and C of FIG. 14 represent three independent experiments, and demonstrate that *H. pylori* can reduce or attenuate allergic response e.g., of allergic airway disease such as asthma in response to allergen in both adults and neonatal subjects. These results further demonstrate that this effect occurs equally as well when either live *H. pylori* or inactivated and/or killed *H pylori* are used. In other words, the results demonstrate that inactivated and/or killed *H. pylori* bacteria are as effective as live *H. pylori* bacteria in reducing or attenuate allergic response e.g., of allergic airway disease such as asthma in response to allergen in both adults and neonatal subjects, thereby protecting subjects from allergic disease such as allergic as asthma.

Example 12

Inactivated and/or Killed H. pylori Cells do not have the Same Colonization Capability of Live H. pylori Cells This example demonstrates the utility of treatment to inactivate and/or kill H. pylori cells in reducing the efficacy of H. pylori cells in colonizing the gastric mucosa of allergic subjects in adult allergic asthma model.

Adult C57BL/6 mice (6 to 8 weeks, n=10) were infected orally by gavage with ~1×10$^9$ CFU of OND79 H. pylori (WT) or treated H. pylori three (3) times per week for a duration of eight (8) weeks. The H. pylori inocula comprised 0.2 ml of a suspension of H. pylori strain OND79 cells in saline solution adjusted to a measured absorbance at 600 nm wavelength of 20 OD unit per ml. Treated H. pylori were inactivated and/or killed as described in Example 1. At the end of the 8 weeks period, mice were sensitized with 2 doses of 50 μg OVA/1 mg alum i.p. (day 0 and 14) and then challenged with OVA aerosol for 5 days from day 31-35. Control mice were uninfected, sensitised and challenged (positive) or only sensitised (negative). Mice were sacrificed on day 36 and stomach tissue harvested. Stomachs were dissected along the greater curvature and residual food removed by gently washing with PBS. Opened stomachs were placed in 500 μl PBS and homogenized with a 5 mm stainless steel bead for 30 seconds at a frequency of 30 (Qiagen TissueLyser II). Samples were further homogenized for 2 min at a frequency of 10. Serial dilutions of homogenates were plated on BHI agar plates supplemented with amphotericin B (8 μg/ml), trimethoprim (5 μg/ml) and vancomycin (6 μg/ml), nalidixic acid (10 μg/ml), polymyxin B (10 μg/ml) and bacitracin (200 μg/ml). Plates were placed in gas-controlled chambers containing two Campygen kit gas packs (Product Code CN0025A, Thermo Fisher Scientific, Oxoid Ltd) and incubated at 37° C. Bacterial growth was determined 5-7 days post plating. Results of H. pylori colonization of the gastric mucosa in infected mice are shown in FIG. 15 and are expressed as the number of colony forming units (CFU) per stomach per mouse.

The results in FIG. 15 demonstrate that although live untreated H. pylori were able to colonize gastric mucosa of allergic mice, treated H. pylori did not colonize gastric mucosa of infected allergic adult mice. This demonstrates that treated H. pylori cells do not have the same colonization capability as a live bacterium having the same genotype.

The inventors also tested the effect of H. pylori colonisation in the neonatal allergic asthma model. In particular, the inventors have repeated the above experiment with the exception that instead of using adult mice, 5-day old female C57BL/6 mice (n=5-10) were infected orally by gavage with ~1×10$^9$ CFU of OND79 H. pylori (WT) or treated H. pylori three (3) times per week for a duration of eight (8) weeks. The H. pylori inocula comprised 0.2 ml of a suspension of H. pylori strain OND79 cells in saline solution adjusted to a measured absorbance at 600 nm wavelength of 20 OD unit per ml. Treated H. pylori were inactivated and/or killed as described in Example 1. At the end of the 8 weeks period mice were treated as above. The results obtained show that colonization with live untreated (WT) H. pylori was achieved in 1 out of 5 neonatal mice at the commencement of the study. On the other hand, no colonization was observed for any mice infected with treated H. pylori as demonstrated by lack of any detectable H. pylor CFU on BHI agar plates plated with undiluted and serial dilutions of 1:10 and 1:100 of homogenised stomach samples (data not shown). These results confirm that treated H. pylori cells which are inactivated and/or killed also have reduced colonization capability relative to a live H. pylori having the same genotype in neonatal subjects.

Example 13

Inactivated and/or Killed H. pylori Cells are Unable to Colonize the Gastric Mucosa This example supports the findings in Example 12 and further demonstrates that treatment to inactivate and/or kill H. pylori cells abrogates ability of H. pylori cells in colonizing the gastric mucosa of adult mice.

Adult C57BL/6 mice (6 to 8 weeks, n=5) were repeatedly inoculated orally by gavage with approximately 1×10$^9$ CFU of treated OND79 H. pylori 3 times per week for 2 weeks. The H. pylori inocula comprised 0.2 ml of a suspension of treated H. pylori strain OND79 cells in saline solution adjusted to a measured absorbance at 600 nm wavelength of 20 OD unit per ml. Treated H. pylori were inactivated and/or killed by subjecting live H. pylori cells to ultraviolet irradiation using UV-C light and optionally further subjected to heat treatment, or by subjecting live H. pylori cells to oxygen starvation treatment for 48 hours and optionally further subjected to heat treatment, as described in Example 2.

To determine the level of colonization, stomach tissue was harvested from animals 2 weeks after final oral inoculation. Stomachs were dissected along the greater curvature and residual food removed by gently washing with PBS. Opened stomachs were placed in 500 μl PBS and homogenized with a 5 mm stainless steel bead for 30 seconds at a frequency of 30 (Qiagen TissueLyser II). Samples were further homogenized for 2 min at a frequency of 10. Serial dilutions of homogenates were plated on H. pylori selective (DENT's supplement, nalidixic acid and bacitracin) F12 agar medium plates. Plates were incubated as described above and after three days of incubation at 37° C. (Anoxomat, 83% $N_2$, 7% $CO_2$, 6% $O_2$ and 4% $H_2$) and single colonies were counted to determine bacterial growth 5-7 days post plating.

Efficacy of infection and colonization of the mouse gastric mucosa for treated H. pylori was assessed based on the number of colony forming units (CFU) per stomach. The results are shown in FIG. 16 and demonstrate that treatment of H. pylori by UV-C irradiation and optionally heat treatment, or by oxygen starvation for 48 hours and optionally further heat treatment abolishes the colonization capability of H. pylori. These results confirm the findings in Example 12 and further demonstrate that it is possible to inactivate and/or kill H. pylori and prevent colonization by H. pylori by more than merely one means of treating live H. pylori cells.

Example 14

Immunological Efficacy of Inactivated and/or Killed H. pylori in Neonatal Allergic is not Strain Specific This example demonstrates a side-by-side comparison of the effects on immunological protection against allergic disease, achieved by administration of treated i.e., inactivated and/or killed H. pylori strains from different geographical origins and belonging to genetically removed ancestral populations of H. pylori. There are identified 6 distinct ancestral populations of H. pylori identified by multi-locus sequence typing analysis and have been named ancestral European 1, ancestral European 2, ancestral East Asia, ancestral Africa1, ancestral Africa2, and ancestral Sahul. *H. pylori* strain OND79 used in this example is a European strain, and *H. pylori* strain J99 used in this example is an African strain.

Live *H. pylori* OND79 cells or *H. pylori* J99 cells were inactivated and/or killed by UV-C irradiation treatment as described Examples 1 and 2. Treated *H. pylori* OND79 cells and treated *H. pylori* J99 cells were administered to 5-day old C57BL/6 mice, and mice were sensitized and challenged with allergen (OVA) by following the same method described in Example 11. Control mice were uninfected, sensitised and challenged (positive control i.e., untreated allergic mice) or only sensitised (negative control i.e., untreated healthy mice). On day 26 mice were sacrificed and serum and collected. In addition, allergen (OVA)-specific IgE and IgG antibodies were measured by standard ELISA methods from serum diluted 1:60. Antibody titres were expressed as the individual and average absorbance at OD405 nm.

As shown in FIG. 17 administration of either UV-C treated *H. pylori* OND79 cells or UV-C treated *H. pylori* J99 cells reduced allergic allergen-specific IgE and IgG antibodies in mice. These results demonstrate that efficacy conferred by administering treated i.e., inactivated and/or killed *H. pylori* (such as UV-C treated *H. pylori*) in allergic asthma mouse model is not strain specific. This is because treated i.e., inactivated and/or killed *H. pylori* of different origins were effective in reducing allergic immune responses to allergen relative to untreated allergic mice.

Example 15

Production of a *H. pylori* Strain Passaged in a Human Host for Use in the Compositions and/or Methods of the Invention This example demonstrates the production and characterization of a passaged strain or derivative of *H. pylori* strain OND79 obtained after passaging in a human host. The resulting passaged or derivative strain of *H. pylori* is suitable for treatment to inactivate and/or kill the cells and use in the compositions and/or methods of the invention.

Expansion of *H. pylori* OND79 for Administration to Human

*H. pylori* OND79 strain was expanded for human administration by the following method. Specifically, commercially available PyloriAgar (PA) plates (from BioMerieux, France) were purchased for culture of *H. pylori* OND79 strain to prepare an inoculum of the OND79 strain for human challenge. To this effect, a glycerol stock vial of *H. pylori* OND79 strain (Heart Infusion [HI] broth containing 20% (v/v) glycerol and 10% (v/v) of *H. pylori* OND79 cells) which had been stored at −80° C., was thawed and inoculated onto 5 PA agar plates. The bacteria-inoculated plates were subjected to an atmosphere evacuation/replacement cycle using an Anoxomat (ANCTS2, Mart Microbiology, Drachten, The Netherlands) to generate micro-aerobic conditions (approximately 83% $N_2$, 7% $CO_2$, 6% $O_2$ and 4% $H_2$) and were incubated at 37° C. for 72 h. The total plate content was then expanded onto new PA plates. Bacteria were harvested and suspended in 1 ml of sterile saline solution (0.9%). Six plates were then inoculated with 100 µl of the bacterial suspension. Cells were evenly distributed on the plates with a sterile disposable loop and incubated under micro-aerobic conditions at 37° C. for 72 h as described above. After 24 h four plates were harvested into 10 ml of regular beef stock solution (1 gram [Continental, Unilever, Australia] in 80 ml preheated water that was filter-sterilized through a 0.2 µm Millipore syringe filter). Biochemical tests including urease, catalase and oxidase tests as well as Gram staining were performed to confirm that the stock solution comprised a pure *H. pylori* culture. The bacterial stock solution was placed on ice and transported to the Department of Gastroenterology and Hepatology at Sir Charles Gairdner Hospital (SCGH) (Western Australia) for administration to the human subject volunteer under SCGH Human Research Ethics Committee approval #2009-062. Approximately $10^9$ viable bacteria were then administered orally to a human subject volunteer by ingestion. Two weeks post administration the patient underwent endoscopy and a gastric biopsy taken to confirm *H. pylori* colonization of the gastric mucosa and the patient was left untreated for a period of at least 12 weeks post administration to maintain *H. pylori* gastric colonization in the human subject.

Isolation of *H. pylori* OND86 Strain from Human Gastric Biopsies

Twelve weeks post bacterial inoculation the human subject underwent an endoscopy to collect several gastric biopsies. One gastric antrum biopsy obtained from the subject was processed by homogenization [Qiagen Tissue Lyser] and serially diluted in sterile physiological saline for culturing bacteria from the gastric biopsy on *H. pylori* selective (DENT's supplement, nalidixic acid and bacitracin) F12 agar medium plates (Thermoscientific, Australia). Bacterial cultures were incubated under micro-aerobic conditions (approximately 83% $N_2$, 7% $CO_2$, 6% $O_2$ and 4% $H_2$) at 37° C. for 72 h as described above, and then single bacterial colonies were isolated and expanded three to four times to produce clonal cultures of a *H. pylori* strain isolated from the gastric biopsy of the patient. Pure clonal *H. pylori* cultures were verified by Gram staining and biochemical tests as above and the expanded single colonies were frozen in triplicates and stored at −80° C. in F12 broth with 20% (v/v) vegetable glycerol (freezing medium). A pure clonal culture of *H. pylori* strain derived from *H. pylori* OND79 after passage in the human subject was named *H. pylori* OND86 strain and a sample was deposited on 10 Jun. 2014 with the National Measurement Institute (NMI), 1/153 Bertrie Street, Port Melbourne, Victoria, Australia, pursuant to the provisions of the Budapest Treaty, and allocated the NMI Accession No. V14/013016.

Characterization of Clinical Isolates of *H. pylori* Derived from OND79 Following Passage in a Human Host Analysis of genomic DNA diversity among the *H. pylori* parent strain OND79 and six clinical isolates of *H. pylori* obtained as described above from gastric biopsies of three human volunteers administered with the parent OND79 strain, was performed using a PCR-based Randomly Amplified Polymorphic DNA (RAPD) fingerprinting method as described by Akopyanz et al., (1992) *Nucleic Acids Research*, 20:5137-5142. The six clinical isolates of *H. pylori* were labelled "#1157 clone 1", "#1157 clone 9", "#86198 clone 1", "#86198 clone 9", "#45156 clone 1" and "#45156 clone 9". Clinical isolates #1157 clone 1, and #1157 clone 9 represent two clonal isolates obtained from the same gastric biopsy of the same human subject (volunteer 1) administered with the parent OND79 strain. Similarly, clinical isolates #86198 clone 1, and #86198 clone 9 represent two clonal isolates obtained from the same gastric biopsy of the same human subject (volunteer 2) administered with the parent OND79 strain. Clinical isolates #86198 clone 1, and #86198 clone 9 represent two clonal isolates obtained from the same gastric biopsy of the same human subject (volunteer 3) administered with the parent OND79 strain. A pure clonal culture of *H. pylori* clinical isolate #1157 clone 9 was chosen for deposit as *H. pylori* OND86 strain under NMI Accession No. V14/013016 described above.

RAPD fingerprinting was performed on the *H. pylori* parent strain OND79 and the six clinical isolates using either the primer "1254" set forth in SEQ ID NO: 3 and having the sequence 5'-CCG CAG CCA A-3', or the primer "1281" set forth in SEQ ID NO: 4 and having the sequence 5'-AAC GCG CAA C-3'. As shown in FIG. 18, genomic RAPD fingerprinting was identical for the parent OND79 strain and for each clinical isolate of the human passage derivative strain including the deposited OND86 strain. Such result indicates that a *H. pylori* strain that has been passaged through an animal host, such as a human host passaged clinical isolates have similar, if not identical, genetic makeup as the parent OND79 strain.

Example 16

*H. pylori* Strain Derived from OND79 that has been Passaged in a Human Shows Strong Colonization Efficacy of the Gastric Mucosa in Infected Animals This example demonstrates that a passaged strain or derivative of *H. pylori* strain OND79 obtained after passaging in a human host is able to colonize the gastric mucosa of animals.

Adult C57BL/6 mice (n=5) were orogastrically inoculated with approximately 1×10⁹ live bacteria from pure cultures of each one of the six clinical isolates of the *H. pylori* obtained after passaging *H. pylori* OND79 in a human host described in Example 15 i.e., #1157 clone 1, #1157 clone 9, #86198 clone 1, #86198 clone 9, #45156 clone 1 and #45156 clone 9. To determine the level of colonization of the 6 clinical isolated (including a clinical isolated of the *H. pylori* OND86 strain deposited under NMI Accession No. V14/013016) stomach tissue was harvested from animals 2 weeks after bacterial administration. Stomachs were dissected along the greater curvature and residual food removed by gently washing with PBS. Opened stomachs were placed in 500 μl PBS and homogenized with a 5 mm stainless steel bead for 30 seconds at a frequency of 30 (Qiagen TissueLyser II). Samples were further homogenized for 2 min at a frequency of 10. Serial dilutions of homogenates were plated on *H. pylori* selective (DENT's supplement, nalidixic acid and bacitracin) F12 agar medium plates. Plates were incubated under micro-aerobic conditions (Anoxomat, approximately 83% N2, 7% CO2, 6% O2 and 4% H2) at 37° C. for 72 h as described above, and then single colonies were counted (i.e., bacterial growth) was determined 5-7 days post plating. Efficacy of infection and colonization of the mouse gastric mucosa for each one of the six isolates of the *H. pylori* derivative strain obtained after passaging *H. pylori* OND79 in a human host was measured based on the number of colony forming units (CFU) per stomach. As shown in FIG. 19, all six clinical isolates (including the deposited *H. pylori* OND86 strain) were able to effectively infect and colonize the mouse gastric mucosa.

Example 17

*H. pylori* Strain Derived from OND79 that has been Passaged in a Human Host Such Demonstrate Strong Efficacy in Colonizing the Gastric Mucosa of Animals This example demonstrates that a passaged strain or derivative of *H. pylori* strain OND79 obtained after passaging in a human host induces specific anti-*H. pylori* IgG antibody in animals.

The adult C57BL/6 mice which were orogastrically inoculated with the live bacteria from pure cultures of each one of the six clinical isolates of the *H. pylori* described in Example 14 were also used to determine the immunogenicity efficacy of the six clinical isolates of the *H. pylori* described above. Serum was collected from the mice at the end point of the colonization experiment described in Example 16. Ninety-six well plates (Nunc Maxisorb) were coated with 10 μg/ml *H. pylori* X47 strain cell lysate and incubated overnight at 4° C. Plates were then washed 5 times in PBS/0.05% Tween-20 and blocked with 2% bovine serum albumin (BSA) for 2 hours at 37° C. Plates were washed twice and serum samples (1/20 dilution) were added to the wells in duplicate. The plates were then incubated for 1 h at room temperature (RT), subsequently washed and detection antibody (anti-mouse IgG conjugated to alkaline phosphatase, 1/1000, Sigma) was added. Plates were further incubated for 1 h at RT then washed. Plates were developed using p-NPP for 60 min before the reaction was stopped with 2M NaOH. Antibody titres were expressed as the OD value measured at 405 nm. As shown in FIG. 20, all six clinical isolates (including the deposited *H. pylori* OND86 strain) were able to induce antibody specific immune responses to *H. pylori*.

Taken together the results presented herein demonstrate inter alia that administration of live, killed or inactivated forms of *H. pylori* to a mammalian subject can modulate the mammalian host immune responses to supress or attenuate allergic immune responses to an allergen, and/or suppress or attenuate allergic airway disease such as allergic asthma. The results presented herein also inter alia demonstrate that formulations comprising live, killed, or inactivated *H. pylori* can prevent development of an allergic immune response or allergic disease such as allergic airway disease, and can have utility as an immunotherapy in children such as neonates and/or juveniles to prevent or limit the atopic march and the progression of allergic disease in a subject e.g., prevent or limit progression of allergic disease in children with eczema to food allergy and/or severe asthma later in life. Furthermore, as demonstrated herein efficacy in supressing or attenuate allergic immune responses to an allergen conferred by killed and/or inactivated *H pylori* is not strain specific.

Further Non-Limiting Examples of the Invention

A composition comprising an isolated *H. pylori* cell, a cell lysate thereof or combination thereof, optionally further processed to produce a processed *H. pylori* preparation such as an extract prepared from whole *H. pylori* cells or proteins isolated from *H. pylori* cells which are partially or completely purified and/or pre-treated, and a pharmaceutically accepted carrier, wherein said *H. pylori* cell is either killed or incapable of colonizing the mucosa of said mammal. The term "composition" as used herein refers a therapeutically-effective or prophylactically-effective amount of the *H. pylori* bacteria or *H. pylori* cell lysate or combination thereof which is optionally in admixture with a pharmaceutically acceptable carrier, excipient or diluent suitable for which are administered to a mammal. Generally, the composition is prepared to be administered as a therapeutically effective amount. A pharmaceutically acceptable carrier are any organic or inorganic inert material suitable for administration to a mammalian musoca, e.g., water, gelatin, gum arabic, lactose, starch, magnesium stearate, talc, vegetable oils, polyalkylene-glycols, petroleum jelly and the like, optionally further comprising one or more other pharmaceutically active agents, flavouring agents, preservatives, stabilizers, emulsifying agents, buffers and the like, added in accordance with accepted practices of pharmaceutical compounding. A "therapeutically effective amount" of the composition of the present invention is understood to comprise an amount effective to elicit the desired response e.g., anergy, but insufficient to cause a toxic reaction. As used herein, the term "anergy" refers to either a diminished immune reaction, or the absence of an immune reaction to an antigen as revealed by the lack of an appropriate immune response, possibly entailing a reversible anti-proliferative state which results in decreased responsiveness of an immune cell or cells to an antigen. The term "cell lysate thereof" as used herein refers to a preparation of the *H. pylori* cells of the present invention, in which the *H. pylori* cells have been disrupted such that the cellular components of the bacteria are disaggregated or liberated. Persons skilled in the art would be well aware of techniques for producing bacterial cell lysates. For example, *H. pylori* cells are pelleted and then resuspended in, for example, Dulbecco's phosphate buffered saline (PBS; 10 mM phosphate, 0.14 M NaCl, pH 7.4) and subjected to sonication on ice with a W-375 sonication Ultrasonic processor (Heat Systems-Ultrasonics, Inc., Farmingdale, N.Y.) at 50% duty cycle with pulse and strength setting 5 for three 1 min sessions. If required, insoluble material and unbroken bacterial cells can then be removed by centrifugation. Alternatively, *H pylori* cells are collected by centrifugation and resuspended in PBS and then lysed by passage through a French press (SLM Instrument Inc., Urbana, Ill.) at 20,000 LB/in. Again, if required, the bacterial lysate are centrifuged at 102,000×g for 10 minutes to remove bacterial debris and/or filtered through a 0.45 μM membrane (Nalgene, Rochester, N.Y.). Another method of producing cell lysate of *H. pylori* involves freezing and thawing of bacterial pellets in the presence of lysozyme. A particular example of a *H. pylori* cell lysate is the soluble fraction of a sonicated culture of the *H. pylori*, e.g., obtained after filtration. Alternatively or in addition, *H. pylori* are fragmented using a high-pressure homogenizer (e.g. Avestin model EmulsiFlexC5). Optionally, the cell lysate is further inactivated by treatment with formalin, or a comparable agent. Alternatively, the immunotherapy composition according to the present invention is obtained by fractionation and/or purification of one or more proteins from a lysate of *H. pylori* culture medium. Obviously, a person skilled in the art will appreciate that if a cell lysate is to be used in the inventive methods described herein there is no need to inactivate or "kill" the *H. pylori* as it will already be disrupted; however, as described supra or infra, the whole *H. pylori* it needs to be either killed or incapable of colonizing the mucosa of said mammal.

A composition consisting essentially of an isolated *H. pylori* cell and a cell lysate thereof together with a pharmaceutically accepted carrier. The terms "composition" and "cell lysate" have the meaning given in paragraph 1.

A composition for use in preventing or treating allergy in a mammal comprising an isolated *H. pylori* cell, a cell lysate thereof or combination thereof and a pharmaceutically accepted carrier, wherein said *H. pylori* cell is either killed or incapable of colonizing the mucosa of said mammal. The terms "composition" and "cell lysate" have the meaning given in paragraph 1 supra. A killed *H. pylori* is in a state of irreversible bacteriostasis. While the *H. pylori* cell retains its structure and thus retains, for example, the immunogenicity, antigenicity, and/or receptor-ligand interactions associated with a wild-type *H. pylori* cell, it is not capable of replicating. There are various methods known in the art to produce killed (whole) bacteria including *H. pylori*, such as exposure to ultraviolet (UV) irradiation, exposure to extreme heat and/or pressure and/or infection with a bacteriophage. In some embodiments, the killed or inactivated *H. pylori* may remain metabolically active e.g., it may wholly retain or partially retain a cell wall and a cell membrane and certain enzymatic functions such as the presence of catalase and superoxide dismutase (SOD) activities for free radical harvesting, however be incapable of colonizing the gastric mucosa of a subject to whom it is administered. A preferred method of producing killed or inactivated *H. pylori* is by heat, UV irradiation, pressure or chemical means. Exemplary means of inactivation by irradiation include exposure to ultraviolet irradiation or gamma irradiation. Once a killed or inactivated *H. pylori* strain, or *H. pylori* strain that is naturally incapable of colonizing the mucosa of a mammal, or *H. pylori* cell lysate has been produced, it are formulated in to a composition of the present invention.

A composition according to any one of paragraphs 1 to 3, wherein the *H. pylori* is killed before use in the invention by, for example, inactivating or killing the strain, or wherein the strain is naturally incapable of colonizing the mucosa of a mammal.

A composition according to any one of paragraphs 1 to 4, wherein the *H. pylori* is a cagA-deficient or cagA$^-$ strain, and preferably a strain that is also positive for toxigenic s1 and m1 alleles of the VacA gene. The terms "cagA$^-$," "cagA minus," "cagA deficient" and the like refer to the absence of the *H. pylori* virulence factor cagA (cytotoxin-associated gene A), which is a 120-145 kDa protein encoded on the 40 kb cag pathogenicity island (PAI) (Hatakeyama & Higashi, (2005), Cancer Science., 96: 835-843). *H. pylori* strains are divided into cagA$^+$ (positive) or cagA$^-$ (negative) strains, of which around 60% of *H. pylori* isolates in Western countries are positive, whereas the majority of East Asian isolates are negative e.g., Hatakeyama & Higashi, (2005).

A composition according to any one of paragraphs 1 to 5, wherein the *H. pylori* has the characteristics of a strain of *H. pylori* selected from the group consisting of OND737, as deposited in the National Measurement Institute under Accession No. V09/009101; OND738, as deposited in the National Measurement Institute under Accession No. V09/009102; OND739, as deposited in the National Measurement Institute under Accession No. V09/009103; OND248, as deposited in the National Measurement Institute under Accession No. V10/014059; OND256 as deposited in the National Measurement Institute under Accession No. V10/014060, OND740 as deposited in the National Measurement Institute under Accession No. V09/009104; OND79 as deposited in the National Measurement Institute under Accession No. V13/023374 and/or OND86 as deposited in the National Measurement Institute under Accession No. V14/013016, or passaged strain, a mutant or a derivative thereof. The term "mutant" or "derivative" as used herein, refers to *H. pylori* which is produced from or derived from a strain of *H. pylori* described herein and as such has genomic DNA at least about 80%, preferably at least about 90%, and most preferably at least about 95%, identical to that of *H. pylori* strain OND737, OND738, OND739, OND740, OND248, OND256, OND79 or OND86.

A composition according to any one of paragraphs 1 to 6, wherein the *H. pylori* has been passaged through an animal host before it is inactivated for use in the present invention.

A composition according to any one of paragraphs 1 to 7, wherein the *H. pylori* is further genetically modified prior to being inactivated to comprise one or more nucleic acid molecule(s) encoding at least one heterologous antigen or a functional fragment thereof. This means that the *H. pylori* will generally express the antigen before it is inactivated. A "genetically modified" *H. pylori* refers to a *H. pylori* bacterium that differs in its phenotype and/or genotype from that of the corresponding wild type *H. pylori* in that it comprises an alteration to or an addition to the genetic makeup present in *H pylori*. Methods for the genetic modification of the *H pylori* are well-known in the art: See, for example, Sambrook & Russell, (2001), "Molecular Cloning—A Laboratory Manual", Cold Spring Harbor Laboratory Press, New York, 3$^{rd}$ Edition. An "isolated genetically modified *H. pylori* cell may be present in a mixed population of *H. pylori* cells. In some embodiments, the genetically modified *H pylori* will comprise one or more nucleic acid molecule(s) encoding at least one heterologous antigen or a functional fragment thereof. The nucleic acid molecule may reside extra-chromosomally or will preferably integrate into the genome of the *H. pylori*. The term "nucleic acid" as used herein refers to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The term "heterologous nucleic acid," as used herein, refers to a nucleic acid wherein at least one of the following is true: (a) the nucleic acid is foreign ("exogenous") to (i.e., not naturally found in) *H. pylori*; (b) the nucleic acid comprises two or more nucleotide sequences or segments that are not found in the same relationship to each other in nature, e.g., the nucleic acid is recombinant. "Recombinant," as used herein, means that a particular nucleic acid (DNA or RNA) is the product of various combinations of cloning, restriction, and/or ligation steps resulting in a construct having a structural coding or non-coding sequence distinguishable from endogenous nucleic acids found in natural systems. Generally, DNA sequences encoding the structural coding sequence are assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences are provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms. Thus, e.g., the term "recombinant" polynucleotide or "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques. In some embodiments, the heterologous nucleic acid sequence is introduced into a *H. pylori* strain of the present invention by a vector. By "vector" is meant a recombinant nucleic acid, generally recombinant DNA, which has been generated for the purpose of the expression and/or propagation of a specific nucleic acid sequence, or is to be used in the construction of other recombinant nucleic acid sequences. The vector often comprises DNA regulatory sequences as well as the nucleic acid sequence of interest. The terms "DNA regulatory sequences", "control elements," and "regulatory elements," refer to transcriptional and translational control sequences, such as promoters, enhancers, polyadenylation signals, terminators, protein degradation signals, and the like, that provide for and/or regulate expression of a nucleic acid sequence in a *H. pylori* cell. The term "transformation" is used interchangeably herein with "genetic modification" and refers to a permanent or transient genetic change induced in a *H. pylori* cell following introduction of a new nucleic acid. Genetic change ("modification") are accomplished either by incorporation of the new DNA into the genome of the *H. pylori* cell, or by transient or stable maintenance of the new DNA as an episomal element such as an expression vector, which may contain one or more selectable markers to aid in their maintenance in the recombinant *H. pylori* cell. Suitable methods of genetic modification include transfection, conjugation, protoplast fusion, electroporation, particle gun technology, calcium phosphate precipitation, direct microinjection, and the like. A general discussion of these methods are found in Ausubel, et al., Short Protocols in Molecular Biology, 3$^{rd}$ ed., Wiley & Sons, 1995. The DNA regulatory sequences and nucleic acid sequence of interest are often "operably linked," which refers to a juxtaposition wherein the components so described are in a relationship permitting them to function in their intended manner. For instance, a promoter is operably linked to a coding sequence if the promoter effects its transcription or expression. As used herein, the terms "heterologous promoter" and "heterologous control regions" refer to promoters and other control regions that are not normally associated with a particular nucleic acid in nature. For example, a "transcriptional control region heterologous to a coding region" is a transcriptional control region that is not normally associated with the coding region in nature. In some embodiments, the nucleic acid sequence encodes a heterologous antigen. A "heterologous antigen" is one not native to *H. pylori*, i.e., not expressed by *H. pylori* in nature or prior to introduction into *H. pylori*. An "antigen" refers to any immunogenic moiety or agent, generally a macromolecule, which can elicit an immunological response in a mammal. The term may be used to refer to an individual macromolecule or to a homogeneous or heterogeneous population of antigenic macromolecules. As used herein, "antigen" is generally used to refer to a protein molecule or portion thereof which contains one or more epitopes, which is encoded by a nucleic acid sequences as herein defined. In various examples of the invention, the antigen contains one or more T cell epitopes. A "T cell epitope" refers generally to those features of a peptide structure which are capable of inducing a T cell response. In this regard, it is accepted in the art that T cell epitopes comprise linear peptide determinants that assume extended conformations within the peptide-binding cleft of MHC molecules, (Unanue et al., (1987), Science, 236:551-557). As used herein, a T cell epitope is generally a peptide having at least about 3-5 amino acid residues, and preferably at least 5-10 or more amino acid residues. The ability of a particular antigen to stimulate a cell-mediated immunological response may be determined by a number of well-known assays, such as by lymphoproliferation (lymphocyte activation) assays, CTL cytotoxic cell assays, or by assaying for T-lymphocytes specific for the antigen in a sensitized subject. See, e.g., Erickson et al., (1993), J. Immunol., 151:4189-4199; and Doe et al., (1994), Eur. J. Immunol., 24:2369-2376. In other examples of the invention, the antigen contains one or more B cell epitopes. A "B cell epitope" generally refers to the site on an antigen to which a specific antibody molecule binds. The identification of epitopes which are able to elicit an antibody response is readily accomplished using techniques well known in the art. See, e.g., Geysen et al., (1984), Proc. Natl. Acad. Sci. USA, 81:3998-4002 (general method of rapidly synthesising peptides to determine the location of immunogenic epitopes in a given antigen); U.S. Pat. No. 4,708,871 (procedures for identifying and chemically synthesising epitopes of antigens); and Geysen et al., (1986), Molecular Immunology, 23:709-715 (technique for identifying peptides with high affinity for a given antibody). In some embodiments, the nucleic acid sequence encoding one or more antigens (allergens) are inserted into a suitable *H. pylori* shuttle vector, e.g., a shuttle plasmid with selectable markers, e.g., antibiotic markers, to assess their transformability. Broadly, a suitable shuttle vector will include one, two, three or more of the following features, a cloning site, a *H. pylori* origin of replication, an *E. coli* origin of replication, and an antibiotic resistance gene and/or selectable marker. Art-known vectors suitable for this purpose, or readily adaptable for this purpose include, for example, the recombinant shuttle plasmid pHR106 described by Roberts et al. (Appl Env Mircobiol., 54: 268-270 (1988)); the PJIR 750 and PJIR 751 plasmids described by Bannam et al. (Plasmid, 29:233-235 (1993)); the promoter-less PPSV promoter selection vector of Matsushita et al. (Plasmid, 31, 317-319 (1994)); the shuttle plasmids pJIR1456 and pJIR1457, described by Lyras et al. (Plasmid, 39, 160-164 (1988)); and the pAK201 shuttle vector described by Kim et al. (Appl Environ Microbiol., 55, 360-365(1989)), the contents of which are incorporated herein by reference in their entireties. Alternatively, homologous recombination are used to introduce an exogenous sequence into the genome of the *H. pylori*. Once the vector, e.g., a shuttle vector, has been produced then nucleic acid transfer protocols are used including transformation/transfection, electroporation, liposome mediated nucleic acid transfer, N-[1-(2,3-Dioloyloxy) propyl]-N,N,N-trimethyl ammonium methyl sulfate meditated transformation, and others. One skilled in the art will be readily able to select the appropriate tools and methods for genetic modifications of the *H. pylori* according to the knowledge in the art and design choice. Once the *H. pylori* or genetically modified *H. pylori* of the present invention has been isolated, passaged through a host and/or prepared, by for example culturing it are used in the present methods.

A composition according to paragraph 8, wherein the nucleic acid molecule resides extra-chromosomally.

A composition according to paragraph 8, wherein the nucleic acid molecule is chromosomally inserted.

A composition according to any one of paragraphs 8 to 10, wherein the heterologous antigen or a functional fragment thereof will encode an environmental antigen. For example, the antigen are obtained or derived from any known allergen including a recombinant allergen. Exemplary recombinant allergens are provided in the tabular representation provided below:

Recombinant Allergens

| Source | Allergen | Reference |
| --- | --- | --- |
| Shrimp/lobster | tropomyosin | Leung et al. (1996) J. Allergy Clin. Immunol. 98: 954 961 |
| | Pan s 1 | Leung et al. (1998) Mol. Mar. Biol. Biotechnol. 7: 12 20 |
| Ant | Sol i 2 (venom) | Schmidt et al. J Allergy Clin Immunol., 1996, 98: 82 8 |
| Bee | Phospholipase A2 (PLA) | Muller et al. J Allergy Clin Immunol, 1995, 96: 395 402 |
| | | Forster et al. J Allergy Clin Immunol, 1995, 95: 1229 35 |
| | | Muller et al. Clin Exp Allergy, 1997, 27: 915 20 |
| | Hyaluronidase (Hya) | Soldatova et al. J Allergy Clin Immunol, 1998, 101: 691 8 |
| Cockroach | Bla g Bd9OK | Helm et al. J Allergy Clin Immunol, 1996, 98: 172 180 |
| | Bla g 4 (a calycin) | Vailes et al. J Allergy Clin Immunol, 1998. 101: 274 280 |
| | Glutathione S-transferase | Arruda et al. J Biol Chem, 1997, 272: 20907 12 |
| | Per a 3 | Wu et al. Mol Immunol, 1997, 34: 1 8 |
| Dust mite | Der p 2 (major allergen) | Lynch et al. J Allergy Clin Immunol, 1998, 101: 562 4 |
| | | Hakkaart et al. Clin Exp Allergy, 1998, 28: 169 74 |
| | | Hakkaart et al. Clin Exp Allergy, 1998, 28: 45 52 |
| | | Hakkaart et al. Int Arch Allergy Immumol, 1998, 115 (2): 150 6 |
| | | Mueller et al. J Biol Chem, 1997, 272: 26893 8 |
| | Der p2 variant | Smith et al. J Allergy Clin Immunol, 1998, 101: 423 5 |
| | Der f2 | Yasue et al. Clin Exp Immunol, 1998, 113: 1 9 |
| | | Yasue et al. Cell Immunol, 1997, 181: 30 7 |
| | Der p10 | Asturias et al. Biochim Biophys Acta, 1998, 1397: 27 30 |
| | Tyr p 2 | Eriksson et al. Eur J Biochem, 1998 |
| Hornet | Antigen 5 aka Dol m V (venom) | Tomalski et al. Arch Insect Biochem Physiol, 1993 22: 303 13 |
| Mosquito | Aed a 1 (salivary apyrase) | Xu et al. Int Arch Allergy Immunol, 1998, 115: 245 51 |
| Yellow jacket | antigen 5, hyaluronidase and phospholipase (venom) | King et al. J Allergy Clin Immunol. 1996, 98: 558 600 |

-continued

| Source | Allergen | Reference |
|---|---|---|
| Cat | Fel d 1 | Slunt et al J Allergy Clin Immunol, 1995, 95: 1221 8 |
| | | Hoffmann et al. (1997) J Allergy Clin Immunol 99: 227 32 |
| | | Hedlin Curr Opin Pediatr, 1995, 7: 676 82 |
| Cow | Bos d 2 (dander; a lipocalin) | Zeiler et al. J Allergy Clin Immunol, 1997, 100: 721 7 |
| | | Rautiainen et al. Biochem Bioph. Res Comm., 1998, 247: 746 50 |
| | ☐-lactoglobuin (BLG, major cow milk allergen) | Chatel et al. Mol Immunol, 1996, 33: 1113 8 |
| | | Lehrer et al. Crit Rev Food Sci Nutr, 1996, 36: 553 64 |
| Dog | Can f1 and Can f2, salivary lipocalins | Konieczny et al. Immunology, 1997, 92: 577 86 |
| | | Spitzauer et al. J Allergy Clin Immunol, 1994, 93: 614 27 |
| | | Vrtala et al. J Immunol, 1998, 160: 6137 44 |
| Horse | Equ e1 (major allergen, a lipocalin) | Gregoire et al. J Biol Chem, 1996, 271: 32951 9 |
| Mouse | mouse urinary protein (MUP) | Konieczny et al. Immunology, 1997, 92: 577 86 |
| Insulin | | Ganz et al. J Allergy Clin Immunol, 1990,86: 45 51 |
| | | Grammer et al. J Lab Clin Med, 1987, 109: 141 6 |
| | | Gonzalo et al. Allergy, 1998, 53: 106 7 |
| Interferons | interferon alpha 2c | Detmar et al. Contact Dermatis, 1989, 20: 149 50 |
| | topomyosin | Leung et al. J Allergy Clin Immunol, 1996, 98: 954 61 |
| Barley | Hor v 9 | Astwood et al. Adv Exp Med Biol, 1996, 409: 269 77 |
| Birch | pollen allergen, Bet v 4 | Twardosz et al. Biochem Bioph. Res Comm., 1997, 23 9: 197 |
| | rBet v 1 Bet v 2 (profilin) | Pauli et al. J Allergy Clin Immunol, 1996, 97: 1100 9 |
| | | van Neerven et al. Clin Exp Allergy, 1998, 28: 423 33 |
| | | Jahn-Schmid et al. Immunotechnology, 1996, 2: 103 13 |
| | | Breitwieser et al. Biotechniques, 1996, 21: 918 25 |
| | | Fuchs et al. J Allergy Clin Immunol, 1997, 100: 3 56 64 |
| Brazil nut | globulin | Bartolome et al. Allergol Immunopathol, 1997, 25: 135 44 |
| Cherry | Pru a 1 (major allergen) | Scheurer et al. Mol Immunol, 1997, 34: 619 29 |
| Corn | Zml3 (pollen) | Heiss et al. FEBS Lett, 1996, 381: 217 21 |
| | | Lehrer et al. Int Arch Allergy Immunol, 1997, 113: 122 4 |
| Grass | Phl p 1, Phl p 2, Phl p 5 (timothy grass pollen) | Bufe et al. Am J Respir Crit Cart Med, 1998, 157: 1269 76 |
| | | Vrtala et al. J Immunol Jun. 15, 1998, 160: 6137 44 |
| | | Niederberger et al J Allergy Clin Immun., 1998, 101: 258 64 |
| | Hol l 5 velvet grass pollen | Schramm et al. Eur J Biochem, 1998, 252: 200 6 |
| | Bluegrass allergen | Zhang et al. J Immunol. 1993; 151: 791 9 |
| | Cyn d 7 Bermuda grass | Smith et al. Int Arch Allergy Immunol, 1997, 114: 265 71 |
| | Cyn d 12 (a profilin) | Asturias et al. Clin Exp Allergy, 1997, 27: 1307 13 |
| | | Fuchs et al. J Allergy Clin Immunol, 1997, 100: 356 64 |
| Japanese Cedar | Jun a 2 (*Juniperus ashei*) | Yokoyama et al. Biochem. Biophys. Res. Commun., 2000, 275: 195 |
| | | 202 |
| | Cry j 1, Cry j 2 (*Cryptomeria japonica*) | Kingetsu et al. Immunology, 2000, 99: 625 629 |
| Juniper | Jun o 2 (pollen) | Tinghino et al. J Allergy Clin Immunol, 1998, 101: 772 7 |
| Latex | Hev b 7 | Sowka et al. Eur J Biochem, 1998, 255: 213 9 |
| | | Fuchs et al. J Allergy Clin Immunol, 1997, 100: 3 56 64 |
| *Mercurialis* | Mer a I (profilin) | Vall verdu et al. J Allergy Clin Immunol, 1998, 101: 3 63 70 |
| Mustard (Yellow) | Sin a I (seed) | Gonzalez de la Pena et al. Biochem Bioph. Res Comm., 1993, 190: 648 53 |
| Oilseed rape | Bra r I pollen allergen | Smith et al. Int Arch Allergy Immunol, 1997, 114: 265 71 |
| Peanut | Ara h I | Stanley et al. Adv Exp Med Biol, 1996, 409 213 6 |
| | | Burks et al. J Clin Invest, 1995, 96: 1715 21 |
| | | Burks et al. Int Arch Allergy Immonol, 1995, 107: 248 50 |
| *Poa pratensis* | Poa p9 | Parronchi et al. Eur J Immunol, 1996, 26: 697 703 |
| | | Astwood et al. Adv Exp Med Biol, 1996, 409: 269 77 |
| Ragweed | Amb a I | Sun et al. Biotechnology Aug, 1995, 13: 779 86 |
| | | Hirsehwehr et al. J Allergy Clin Immunol, 1998, 101: 196 206 |
| | | Casale et al. J Allergy Clin Immunol, 1997, 100: 110 21 |
| Rye | Lol p I | Tamborini et al. Eur J Biochem, 1997, 249: 886 94 |
| Walnut | Jug r I | Teuber et al. J Allergy Clin Immun., 1998, 101: 807 14 |
| Wheat | allergen | Fuchs et al. J Allergy Clin Immunol, 1997, 100: 356 64 |
| | | Donovan et al. Electrophoresis, 1993, 14: 917 22 |
| *Aspergillus* | Asp f 1, Asp f 2, Asp f 3, Asp f 4, rAsp f 6 | Crameri et al. Mycoses, 1998, 41 Suppl 1: 56 60 |
| | | Hemmann et al. Eur J Immunol, 1998, 28: 1155 60 |
| | | Banerjee et al. J Allergy Clin Immunol, 1997, 99: 821 7 |
| | | Crameri Int Arch Allergy Immunol, 1998, 115: 99 114 |
| | | Crameri et al. Adv Exp Med Biol, 1996, 409: 111 6 |
| | | Moser et al. J Allergy Clin Immunol, 1994, 93: 1 11 |
| | Manganese superoxide dismutase (MNSOD) | Mayer et at Int Arch Allergy Immunol, 1997, 113: 213 5 |
| *Blomia* | allergen | Caraballo et al. Adv Exp Med Biol, 1996, 409: 81 3 |
| *Penicillinium* | allergen | Shen et al. Clin Exp Allergy, 1997, 27: 682 90 |
| *Psilocybe* | Psi e 2 | Homer et al. Int Arch Allergy Immunol, 1995, 107: 298 300 |

A composition according to any one of paragraphs 8 to 11, wherein the nucleic acid molecule encoding the heterologous antigen will reside in a plasmid vector comprising (a) a nucleotide sequence encoding the heterologous antigen and (b) a control or regulatory sequence operatively linked thereto which is capable of controlling the expression of the nucleic acid when the vector is transformed into a H. pylori strain.

A composition according to any one of paragraphs 1 to 12, wherein the composition further comprises an adjuvant. Any adjuvant known in the art may be used.

A composition according to paragraph 13, wherein the adjuvant is selected from 5 the group consisting of alum, pertussis toxin, Lacto fucopentaose III, phosphopolymer, complete Freund's adjuvant, monophosphoryl lipid A, 3-de-O-acylated monophosphoryllipid A (3D-MPL), aluminium salt, CpG-containing oligonucleotides, immunostimulatory DNA sequences, saponin, MONTANIDE® ISA 720, SAF, ISCOMS, MF-59®, SBAS-3, SBAS-4, Detox, RC-529, aminoalkyl glucosaminide 4-phosphate, 10 and LbeiF4A or combinations thereof.

A composition according to any one of paragraphs 1 to 14, wherein the composition is formulated to prevent or treat anergy and/or allergy in a mammal. The dosage and duration of administration of the composition to a mammal will be determined by the health professional attending the mammalian subject in need of treatment, and will consider the age, sex and weight of the subject, the specific H. pylori and nucleic acid molecule being expressed or the state in which the H. pylori and/or cell lysate thereof e.g., whether the H. pylori is killed or alive or the strain of H. pylori being used. The various delivery forms of the compositions are readily prepared for use in the practice of the present invention given the specific types and ratios of specific H. pylori, plasmid vectors and other delivery mechanisms described herein, and those formulation techniques known to those in the formulary arts, such as are described in Remington's Pharmaceutical Sciences, 20th edition, Mack Publishing Company, which text is specifically incorporated herein by reference. One application of the composition of the invention is to alter, ameliorate, or change the immune response to one or allergens (antigens), thereby resulting in anergy. The terms "altering or altered," "effecting or effected" or "altering relative to" are all used herein to imply or suggest that the specific immune response of an individual has been modified when compared to specific immune response before the methods of the invention have been used. Allergic diseases that are specifically considered to be prevented and/or treated by the methods of the present invention include, but are not limited to contact dermatitis (Kapsenberg et al., Immunol Today 12:392-395), chronic inflammatory disorders such as allergic atopic disorders (against common environmental allergens) including allergic asthma (Walker et al., (1992), Am. Rev. Resp. Dis. 148:109-115), atopic dermatitis (van der Heijden et al., (1991), J. Invest. Derm. 97:389-394); hyper-IgE syndrome, Omenn's syndrome, psoriases, hay fever, allergic rhinitis, urticaria, eczema and food allergies. The H. pylori containing composition may be formulated for administration or delivery "orally," "enterally," or "non-parenterally," i.e., by a route or mode along the alimentary canal.

A composition according to paragraph 15, wherein the allergy is selected from the group consisting of contact dermatitis, chronic inflammatory disorders, allergic atopic disorders, allergic asthma, atopic dermatitis, hyper-IgE syndrome, Omenn's syndrome, psoriases, hay fever and allergic rhinitis.

A composition according to any one of paragraphs 1 to 16, wherein the composition is formulated to be orally administered. Examples of "oral" routes of administration of a composition include, without limitation, swallowing liquid or solid forms of a composition from the mouth, administration of a composition through a nasojejunal or gastrostomy tube, intraduodenal administration of a composition, and rectal administration, e.g., using suppositories that release the H. pylori strain as described herein to the lower intestinal tract of the alimentary canal.

A method of treatment or prevention of allergy in a mammal at risk of developing said method comprising the step of administering to said mammal an effective amount of a composition comprising an isolated H. pylori cell, a cell lysate thereof or combination thereof and a pharmaceutically accepted carrier, wherein said H. pylori cell is either killed or incapable of colonizing the mucosa of said mammal, wherein said composition, upon administration, provides protective immunity against said allergy. Preferably, the composition is the composition according to any one of paragraphs 1 to 17. The term "mucosa" in this context refers to the lining of mammalian tissue including, but not limited to oral mucosa esophageal mucosa, gastric mucosa, nasal mucosa, bronchial mucosa and uterine mucosa. Preferably, the mucosa is the gastric mucosa. Mucosal delivery may encompass delivery to the mucosa. Oral mucosal delivery includes buccal, sublingual and gingival routes of delivery. Accordingly, the present invention relates to a method in which said mucosal delivery is chosen from the group consisting of buccal delivery, pulmonary delivery, ocular delivery, nasal delivery and oral delivery. Preferably, said mucosal delivery is oral delivery. The term "mammal" or "mammalian subject" or "individual" are used interchangeably herein to refer to any member of the subphylum Chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The method is intended for use in any of the above vertebrate species. The term "treatment" is used herein to mean affecting an individual or subject, their tissue or cells to obtain a desired pharmacological and/or physiological effect, such as by prophylaxis i.e., complete or partial prevention of allergic disease or sign or symptom thereof, or by therapy i.e., partial or complete cure of allergic disease, including: (a) preventing the allergic disease from occurring in a subject that may be predisposed to the allergic disease, but has not yet been diagnosed as having them; (b) inhibiting the allergic disease, i.e., arresting its development; or (c) relieving or ameliorating the symptoms of the allergic disease, i.e., cause regression of the symptoms of the allergic disease.

A method of treatment or prevention of allergy in an immunologically naive mammal at risk of developing said allergy, said method comprising the step of: (i) identifying a mammal at risk of developing an allergy; (ii) administering to said mammal a composition comprising an isolated H. pylori cell, a cell lysate thereof or combination thereof and a pharmaceutically accepted carrier, wherein said H. pylori cell is either killed or incapable of colonizing the mucosa of said mammal and (iii) allowing sufficient time to elapse to enable anergy to develop. Preferably, the composition is the composition according to any one of paragraphs 1 to 17. The terms "mucosa" and "mammal" and "treatment" have the meanings given in paragraph 18 hereof.

A method of treatment or prevention of allergy in a mammal comprising the step of administering to said mammal an effective amount of a composition comprising an isolated *H. pylori* cell, a cell lysate thereof or combination thereof and a pharmaceutically accepted carrier, wherein said *H. pylori* cell is either killed or incapable of colonizing the mucosa of said mammal, wherein said composition, upon administration, provides protective immunity against said allergy. Preferably, the composition is the composition according to any one of paragraphs 1 to 17. The terms "mucosa" and "mammal" and "treatment" have the meanings given in paragraph 18 hereof.

A method according to any one of paragraphs 18 to 20, wherein the mammal is a dog, a cat, a livestock animal, a primate or a horse.

A method according to paragraph 21, wherein the primate is a human. Adult and newborn and infant humans, are intended to be treated by this invention. In some embodiments, the mammal is a human child between 3 months and 7 years old, not less than 6 months old, more preferably not less than 9 months old. In some embodiments, the mammal is a human individual older than 7 years. Because in early childhood most individuals will not yet have been exposed to sensitisation by environmental allergens, it is considered that this period provides the optimum opportunity to predict the likely onset of allergy.

A method according to paragraph 22, wherein the human is below the age of about 5.

A method according to paragraph 23, wherein the human is below the age of 2 years.

A method according to any one of paragraphs 18 to 24, wherein the allergy is selected from the group consisting of contact dermatitis, chronic inflammatory disorders, allergic atopic disorders, allergic asthma, atopic dermatitis, hyper-IgE syndrome, Omenn's syndrome, psoriases, hay fever and allergic rhinitis.

A kit for treating and/or preventing allergy in a mammal comprising:
 i). a composition according to any one of paragraphs 1 to 17; and
 ii). instructions for use in a method according to any one of paragraphs 18 to 25.

A method of generating a *H. pylori* strain that is able to provide protective immunity against allergy comprising the steps of:
 (a) providing an isolated *H. pylori* cell that is;
  (i) incapable of colonizing the mucosa of a mammal and/or
  (ii) cagA minus (cagA) and optionally positive for the toxigenic s1 and m1 alleles of the VacA gene;
 (b) optionally passaging said *H. pylori* cell through an animal host; and
 (c) optionally inactivating or killing said *H. pylori* cell.

---

The claims defining the invention are as follows:

1. A method of interrupting or slowing or arresting or preventing an atopic march or progression of an atopic march in a human subject having or susceptible to atopic march, the method comprising, administering to the subject an effective amount of a composition comprising an inactivated or killed *H. pylori* cell or a cell lysate thereof.

2. A method for preventing an allergic immune response to an allergen or reducing severity or incidence of an allergic immune response to an allergen in a human subject having or susceptible to an allergic immune response to an allergen comprising administering to the subject a therapeutically effective amount of killed or inactivated *H. pylori* cells or a cell lysate thereof.

3. The method of claim 2, wherein said method comprises administering a daily dosage of the *H. pylori* cells or cell lysate wherein each dose comprises an amount of bacteria in a range corresponding to between about $10^6$ cells to about $10^{12}$ cells, or a lysate thereof.

4. The method of claim 2, wherein the *H. pylori* cells or cell lysate thereof is administered to a juvenile human subject to prevent eczema in the juvenile or a subsequent onset of allergy or asthma in later life.

5. The method of claim 2, wherein the *H. pylori* cells or cell lysate thereof is administered over a period of at least about 2 weeks.

6. The method of claim 2, wherein the *H. pylori* cells or cell lysate thereof is administered over a period of at least about 4 weeks.

7. The method of claim 2, wherein the *H. pylori* cells or cell lysate thereof is administered over a period of at least about 6 weeks.

8. The method of claim 2, wherein the *H. pylori* cells or cell lysate thereof is administered over a period of at least about 8 weeks.

9. The method of claim 2, wherein the *H. pylori* cells or cell lysate thereof is administered over a period of at least about 10 weeks.

10. The method of claim 2, wherein the *H. pylori* cells or cell lysate thereof is administered over a period of at least about 12 weeks.

11. The method of claim 2, wherein said method prevents or delays an increase in a serum level of allergen-specific IgE antibody and/or prevents or delays an increase in a level of one or more inflammatory cytokines in bronchioalveolar lavage (BAL) and/or prevents or delays an increase in a level of cell infiltrate in lung in a human subject exposed to an allergen.

12. The method of claim 2, wherein said method comprises administering *H. pylori* whole cell lysate.

* * * * *

UNITED STATES PATENT AND TRADEMARK OFFICE
CERTIFICATE OF CORRECTION

PATENT NO. : 9,555,104 B2
APPLICATION NO. : 14/897575
DATED : January 31, 2017
INVENTOR(S) : Mohammed J Benghezal et al.

It is certified that error appears in the above-identified patent and that said Letters Patent is hereby corrected as shown below:

In the Specification

Column 7, Line 51, change "petiussis" to –pertussis–

Column 30, Line 2, change "pylon" to –pylori–

Column 46, Line 43, change "SM" to –*Sty*I–

Column 46, Line 60, change "Styl" to –*Sty*I–

Signed and Sealed this
Twenty-seventh Day of June, 2017

Joseph Matal
*Performing the Functions and Duties of the*
*Under Secretary of Commerce for Intellectual Property and*
*Director of the United States Patent and Trademark Office*